(12) United States Patent
Daneshvar

(10) Patent No.: US 8,469,912 B2
(45) Date of Patent: Jun. 25, 2013

(54) DANESHVAR WOUND DRESSING, SUPPORT UNITS AND METHODS, MODEL DAPHNE

(76) Inventor: Yousef Daneshvar, West Bloomfield, MI (US)

( * ) Notice: Subject to any disclaimer, the term of this patent is extended or adjusted under 35 U.S.C. 154(b) by 2005 days.

(21) Appl. No.: 10/330,732

(22) Filed: Dec. 28, 2002

(65) Prior Publication Data

US 2003/0135146 A1  Jul. 17, 2003

Related U.S. Application Data

(60) Provisional application No. 60/345,551, filed on Jan. 7, 2002, provisional application No. 60/355,550, filed on Feb. 7, 2002.

(51) Int. Cl.
*A61F 13/00* (2006.01)

(52) U.S. Cl.
USPC .................................. 602/61; 602/75; 602/78

(58) Field of Classification Search
USPC ................. 602/41–59, 60–79, 112, 201–204, 602/19; 606/112, 201–204; 128/118.1, 98.1
See application file for complete search history.

(56) References Cited

U.S. PATENT DOCUMENTS

| | | | | |
|---|---|---|---|---|
| 3,529,601 A | * | 9/1970 | Kirkland | 604/312 |
| 4,665,909 A | * | 5/1987 | Trainor | 602/76 |
| 5,520,630 A | * | 5/1996 | Daneshvar | 602/60 |
| 5,779,657 A | * | 7/1998 | Daneshvar | 602/60 |
| 7,048,818 B2 | * | 5/2006 | Krantz et al. | 156/66 |

OTHER PUBLICATIONS

"Elastic Loop Tapes", XP-002091024, Velcro Fastening Systems, Product Information Guide, Aug. 1997, 2 pages.*
"Elastic Loop Tapes" Velcro Fastening Systems, Product Information Guide, Aug. 1997, 2 pages.*
PTO- 1449, from U.S. Appl. No. 09/808,395, filed Jul. 2005.*

* cited by examiner

*Primary Examiner* — Kim M Lewis

(57) ABSTRACT

A wrap for encircling a portion of a living body has a relatively non-stretchable support and a strap that has an attached zone attached to the support. The strap is relatively stretchable along its length as measured from that zone and long enough to encircle the portion of the living body and attach, with some stretching, back to an attachment means on the support for keeping the encircled portion of the body wrapped. The strap has relatively stretchable material that stretches with stretching of the strap and serves to attach the strap back to the attachment means on the support after having encircled the portion of the body.

25 Claims, 30 Drawing Sheets

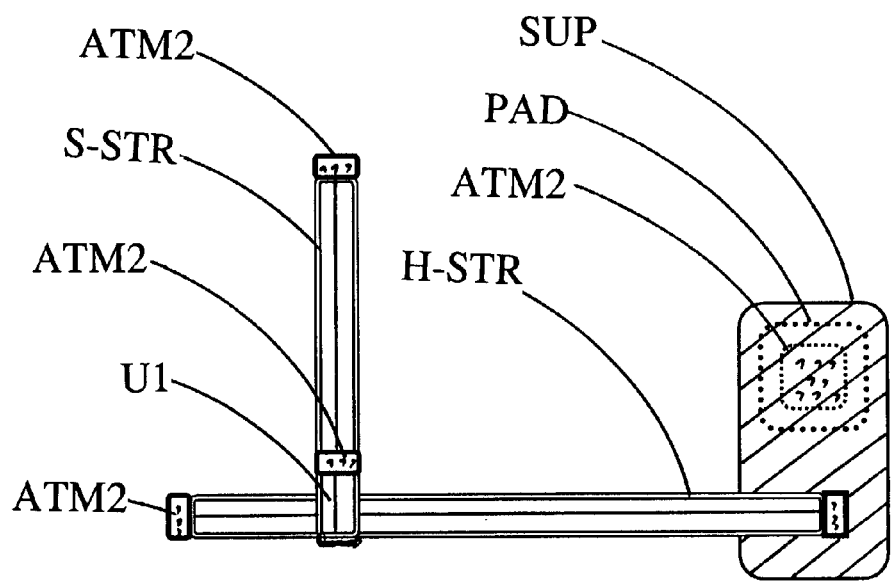
Figure 30
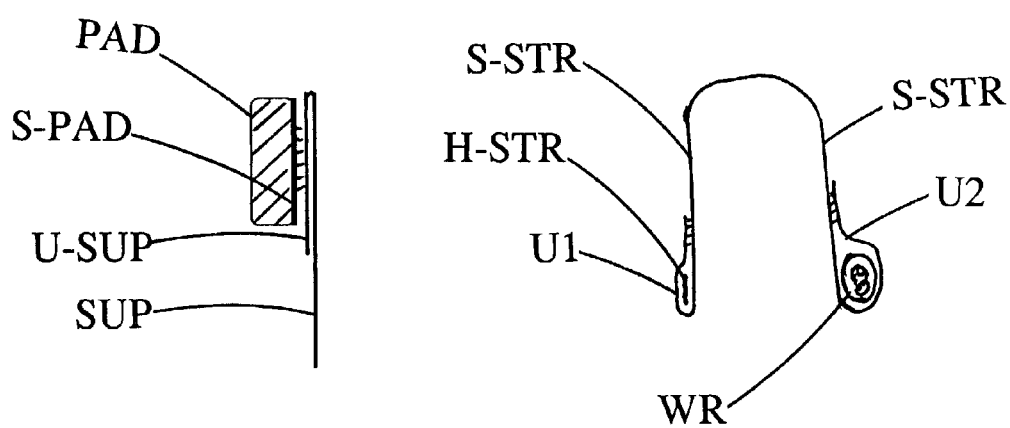
Figure 31
Figure 31A

DANESHVAR WOUND DRESSING, SUPPORT UNITS AND METHODS, MODEL DAPHNE

This is a regular application requesting the priority of the following provisional applications: Filing No. 60/345,551, filing date Jan. 7, 2002 and Filing No. 60/355,550, filing date Feb. 7, 2002.

I claim the benefit of the earlier U.S. Provisional application with filing No. 60/345,551, filing date Jan. 7, 2002 with the invention title: DANESHVAR'S WOUND DRESSING UNITS AND METHODS.

I also claim the benefit of the earlier U.S. Provisional application with filing No. 60/355,550, filing date Feb. 7, 2002 with the title of invention: DANESHVAR'S WOUND CARE DRESSING UNITS AND METHODS.

THE BACKGROUND OF THIS INVENTION

This invention is related to wound dressings and supports in humans and animals. At present, adhesives and wraps are used for this purpose. However, the use of adhesives has multiple problems: they are difficult to use with elastic gloves since adhesive tapes adhere to the gloves, they cause skin irritations and discomfort on removal, and do not adhere to the skin covered by hairs. Many times the hair has to be shaved which is a separate process of its own. Wound inspections or the exchange of dressing multiplies their problems and prohibits this process. Furthermore, wound wrapping cannot be done through use of adhesive tapes in an effective and convenient method. Then, there is the major issue of dressing a wound with one hand, which is crucial in certain circumstances. It thus becomes very important for a wound dressing system to allow a person to dress a wound with one hand only since the other one could be wounded or disfunctional. And lastly, at times wound dressing should be done as quickly as possible, and speed makes a big difference in manmade or natural disasters. The methods and means introduced in this application solve many of these problems.

THE BRIEF EXPLANATION OF THE INVENTION

This application introduces new methods and means of dressings that make the process of wound dressing faster and easier and applicable with one hand. It practically eliminates the use of adhesives tapes on skin and/or decreases their use significantly. In this model a support unit made from a non-stretchable material, commonly in rectangular- or trapezoid-shape, is used to cover the wound and hold the gauze pad or wound dressing in place. This unit uses at least one strap made of a particular stretchable material that allows the strap to attach to the support on a detachable, re-attachable basis. Very importantly, the attachment of the strap to a hook-fastener can be done in any part of the surface of this strap. Importantly also, this support system uses one or two narrow bands made from the same material as the strap, which allows them to wrap around the limb from the opposite side of the strap to attach to the support on a detachable, re-attachable basis. Then the main strap will attach to the support on detachable, re-attachable basis. In some models the support unit will function as the stabilizer of the system or to make the functions simpler and easier. This main idea, then, is used to make multiple models for use in different areas.

Please note that in this application the hook- and loop-fastener attachment means are utilized very frequently, and in general:
a. The loop-fastener attachment means is referred to as ATM1
b. The hook-fastener attachment means is referred to as ATM2

Please note that any other types of attachment means may be also used in these units if possible.

Also please note that each wound support unit in this application uses a support piece or means and that these support means are basically of two types:
a. Type I support means are made from a non-stretchable layer such as vinyl whose body has zones of attachment means on it.
b. Type II support means is made from a non-stretchable layer with a laminated body; an outer layer made from a layer of loop-fastener attachment means, ATM1, an inner layer which is a soft, fabric lining upon skin contact and a layer of foam in between.

Please note that the Type II support means may also have zones of hook-fastener attachment means, ATM2, on them. This makes a very particular unit that allows the attachment of a strap made from a loop-fastener attachment means, ATM1, with end pieces or zones of hook-fastener attachment means, ATM2, to occur on a double-function as follows:
1. The zones of the hook-fastener attachment means, ATM2, from the ends of the strap will attach to the outer surface of the Type II support on a detachable, re-attachable basis.
2. The body of the strap, made from a loop-fastener attachment means, ATM1, will also attach to the zones of the hook-fastener attachment means, ATM2, on the support on a detachable, re-attachable basis as well. This is the reason why a double-attachment occurs that is very useful in many models of these units.

The figures: Please notice that different parts of this invention are shown in different figures. This is to prevent a crowded picture. Importantly, all of the options are designed to be used in one model if applicable.

BRIEF EXPLANATION OF THE FIGURES

FIG. 5A shows a support piece that has a wall that attaches to the support to keep tubings and wires in between.

FIG. 30 shows a support unit for the Pacemaker-Defibrillator Wound.

FIG. 31 shows the side view of a support unit shown in previous FIG. 30.

FIG. 31A shows the side view of the arrangement of the straps for the unit shown at FIG. 31.

DETAILED EXPLANATION OF THE FIGURES

Figure 1:
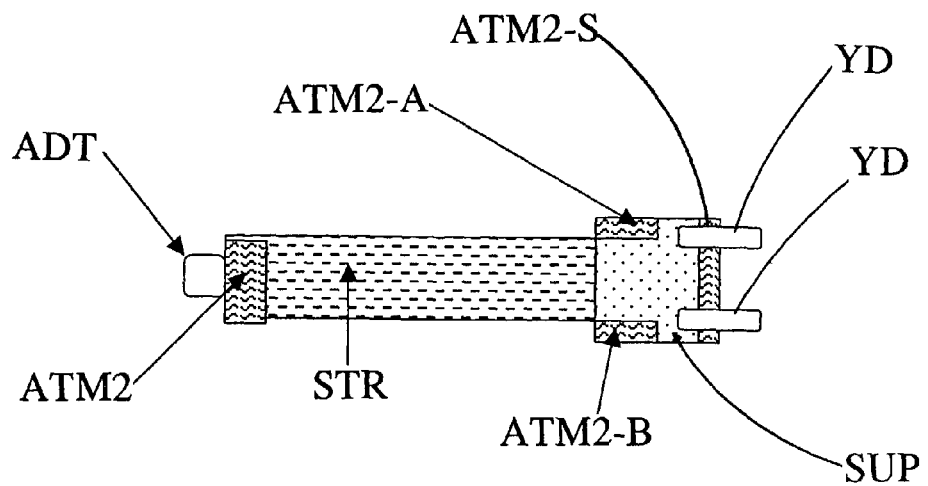
FIG. 1 shows the front view of a strap and support unit that uses adhesive pieces on its right side to allow this unit to be used with one hand only.
Figure 3:
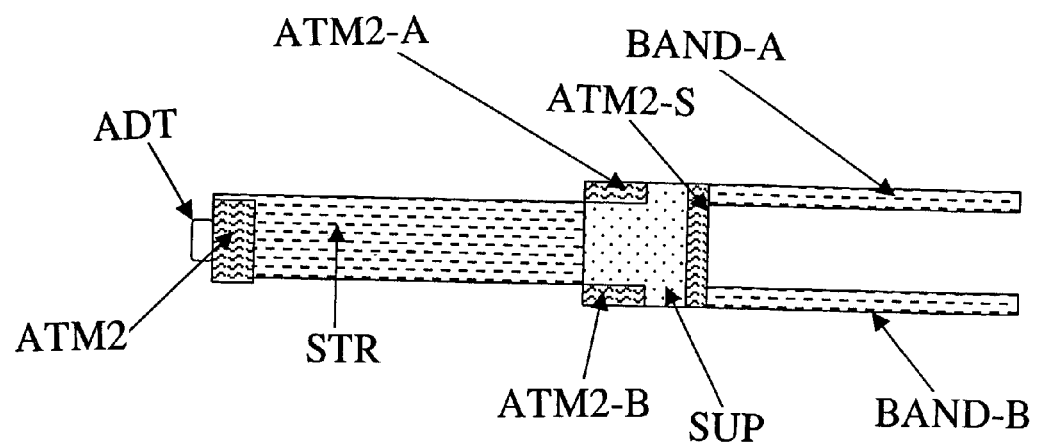
FIG. 3 shows a similar unit as shown at FIG. 1, except this unit uses bands shown on the right side to allow it to be used with one hand.
Figure 4:
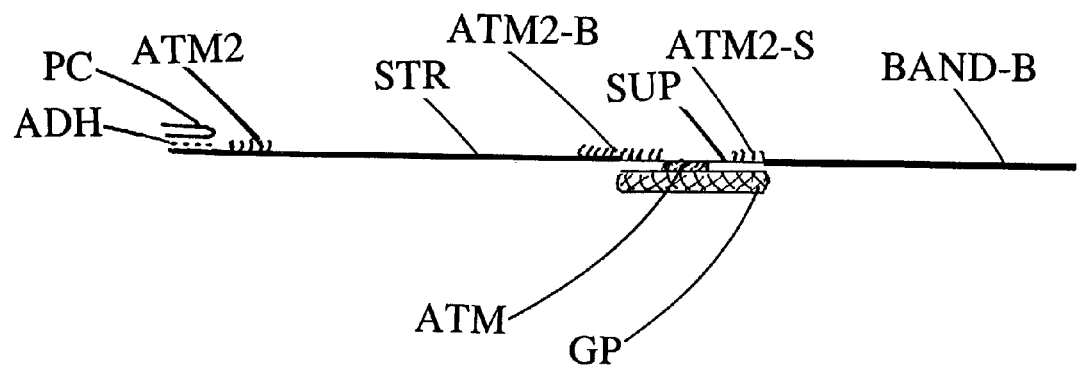
FIG. 4 shows the side view of the unit shown at FIG. 3.

FIG. 1 shows the front view of a wound dressing unit that consists of a clear front support, SUP, which has a strap, STR, attached to it on the left side of the support (when we view the Figure). In this model the support, SUP, is made from a layer of vinyl and has zones of attachment means shown at ATM2, made from hook type of hook-loop-fastener (VELCRO TM). These zones are further specified by ATM2-A, ATM2-B and ATM2-S. These hook-fastener patches allow complementary pieces such as the body of the strap, STR, which function as a loop type of attachment means. This property allows the strap, STR, to attach to the zones of the hook-fastener attachment means shown at ATM2-A, ATM2-B and ATM2-S, or any similar zones, on a detachable, re-attachable basis. Specifically the applicant has found in his study that when the strap is made from special material such as (LYCRA-TM), it allows the strap to attach to the hook type attachment means, categorically shown at ATM2, on a detachable, re-attachable basis. The free end of the strap, STR, also has a band made of hook-fastener attachment means ATM2 (this may be double-sided) that allows it to be attached to the rear surface of the body of the strap, STR, on a detachable, re-attachable basis. The zones of the attachment means, ATM2-A and ATM2-B, allow complementary bands made from similar material as the strap or similar units to be attached to them on a detachable, re-attachable basis. An example of this model is shown at FIGS. 3 and 4.

Figure 2:
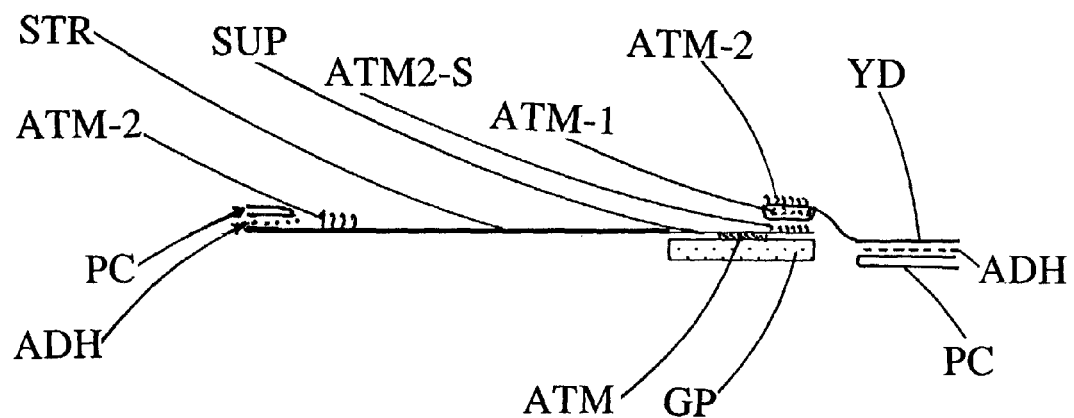
FIG. 2 shows the vertical cross-cut view of the unit shown in the previous figure.

The free end of the strap, STR, may have a piece of adhesive tape, (ADT), which allows it to be attached to the rear surface of the strap in order to keep the free end of the strap, STR stable should the zone, ATM2, not attach to it for some reason. Part ADT may be made from any other attachment means such as snaps or other possible means to allow the free end of the strap to be attached to the surface of the strap, STR, itself. The adhesive may be chosen to function on a detachable, reattachable basis. The adhesive tape ADT, has a layer of adhesive ADH protected by a removeable cover PC, as shown in FIG. 2. The protected cover, PC will be peeled off before use. The protective cover (PC) of the adhesive tape is folded to allow removal without allowing the gloves to touch the adhesive layer, which would stick.

This unit also allows the use of special pieces (previously introduced by this applicant and referred to as YD pieces), shown better at FIG. 2. YD pieces are made from a piece of medical adhesive tape with a zone of loop-fastener attachment means as shown at ATM1. This zone is placed on the surface where the adhesive material is located, as shown at FIG. 2. It allows the end of the YD piece to attach to the zone of ATM2-S from the support unit. The rear surface of this zone ATM-1 on the YD piece has a zone of hook-fastener, ATM2 of its own that allows a complementary piece, such as strap, to attach to it on a detachable, re-attachable basis.

The support, SUP, may also have a piece of gauze pad, GP, attached to it in order to be ready for use. This will eliminate preparation time of the gauze piece since time can be critical in many circumstances. The gauze pad, GP, is attached to the body of the support, SUP, by an attachment means shown at ATM that allows the gauze pad to be exchanged when needed.

Importantly, the body of the support may have a series of holes or openings that allow air, sweat and other gasses to go through. Also, it may have a series of tabs on its surface that will allow it to be held and moved on the wound site easily. Importantly, this basic unit can be modified for use in different places such as chest, hip, abdomen, knees, extremities, and so on.

The external end of the YD piece has a layer of adhesive (ADH) covered with a folded protective layer, PC, that allows it to stick the adhesive part onto the skin. This allows the person to use this unit with one hand and exchange the wound dressing without the need for another adhesive part each time since the YD piece can be separated from the support on a detachable, re-attachable basis.

Importantly, instead of the zones of the attachment means (ATM2-A) and (ATM2-B) the unit may have a second long zone of the hook-fastener attachment means such as the zone ATM2-S on the left border of the support, SUP. This will allow the strap, STR or the use of the bands BAND-A, BAND-B as shown in FIGS. 3-4 to occur.

FIG. 2 shows the side view of a wound dressing unit shown at FIG. 1. This figure shows the vertical cut view/side of the support, SUP, and the strap, STR, as shown in FIG. 1. The support, SUP, has patches of the attachment means which, in general, are shown at (ATM2) on its upper surface. These are further specified by the zones such as ATM2-B, ATM2-S, etc. In this figure the ATM2-S is shown, but the attachment means ATM2-B is not shown, since the cross-cut was in the middle of the unit. On the right side of this figure the YD piece is shown. The lower surface of the YD piece on its left side has a zone of loop-fastener attachment means ATM-1 that allows it to be attached to the zone of ATM2-S from the support on a detachable, re-attachable basis. The YD piece has a layer of adhesive, shown at ADH on a dotted-line, that allows this part to adhere to the skin and hold the end of the support, SUP, securely on the skin. The layer of adhesive has a folded protected cover (PC) that will be peeled off before use. Importantly, the folded protective cover PC allows it to be held and pulled off easily from the adhesive layer to expose the adhesive layer. This allows users with latex gloves to use these units easily, without touching the adhesive layer that sticks to the latex gloves. The YD piece has a patch of the attachment means: ATM2 on its upper surface, made from hook type of hook-loop-fastener (VELCRO TM). This patch allows a complementary piece such as the body of the strap STR or other units with loop-fastener properties to be attached to it on a detachable, re-attachable basis.

The gauze pad, GP, is attached to the lower surface of the support, SUP, by attachment means ATM.

The free end of the strap, STR, shown on the left side has a zone of attachment means: ATM2 made from hook type of hook-loop-fastener (VELCRO TM). This zone allows the free end of the strap, STR, to be attached to the outer surface of the body of the strap STR on a detachable, re-attachable basis. Please note that after the strap is attached to the support it will make a U-turn and then its free end will attach to the outer surface of the strap.

Importantly, in another version, the zone of attachment means, ATM2 may be placed on the lower side of the strap, STR as shown in this figure (instead of being on the upper surface of the strap as shown). In that case the strap, STR, will wrap over the front of the support and then the free end will to be attached to the outer surface of the body of the strap, STR, on a detachable, re-attachable basis.

The adhesive tape at the very end of the strap, STR, is shown by the layer of adhesive at ADH shown on the dotted line. The layer of adhesive has folded protected cover (PC).

Importantly, again in the second version, the layer of adhesive, ADH, can be in the lower side of the strap as shown in this figure (instead of being on the upper surface of the strap as shown). In that case the strap, STR, will wrap over the support and then the adhesive tape from the free end be adhered to the outer surface of the body on a detachable, re-attachable basis.

FIG. 3 shows the front/top view of a wound dressing unit similar to the unit shown at previous FIG. 1 except this unit has two bands made of a material similar to the strap, STR. These bands, shown at BAND-A and BAND-B, are designed to attach to the attachment patches, ATM2-A and ATM2-B of the support, SUP, on a detachable, re-attachable basis, so that they can be attached, detached and re-attached.

Importantly, instead of the zones of the attachment means (ATM2-A) and (ATM2-B) the unit may have a second, long zone of the hook-fastener attachment means such as the zone ATM2-S on the left border of the support, SUP. This allow the attachment of the strap, STR, or the bands BAND-A, BAND-B to support.

Importantly, in these models the strap, STR, and bands, BAND-A and BAND-B, are made from special material (LYCRA-TM) that allow these pieces to attach to the attachment means, ATM2, on a detachable, re-attachable basis. The free end of the strap, STR, shown in the left side of this figure has a piece of adhesive tape, ADT, which allows it to be attached to the rear surface of the strap, STR, after making a U-turn, and keep the end piece stable.

Instead of the adhesive tape, ADT, this part may be made from any other materials or means that will allow the end of the strap, STR, to be attached to the surface of the strap, STR, on a detachable, reattachable basis. The adhesive tape, ADT, has a removeable protective cover that will be peeled off before use. This is shown better in FIG. 4. The protective cover of the adhesive tape allows it to be removed without touching the gloves.

The significant importance of this unit is that it allows the subject to dress a wound with use of one hand only, which the applicant believes is very important. At the time of use the user:

First. Places the support piece, SUP, on the wound and places the strap, STR, under the limb so that by pressing on the strap, STR, it will temporarily prevent the support, SUP, from moving.

Second. He/she will wrap the proximal band, Band-A, around the limb in the opposite side of the strap, STR, and bring its free end to attach to the ATM2-A from the support on detachable, re-attachable basis.

Third. The user will wrap the distal band, Band-B, around the limb on the opposite side of the strap, STR, to bring its free end and attach it to the ATM2-B on the support on a detachable, re-attachable basis.

Fourth. In this move the user will wrap the strap, STR, around the limb for attachment to the ATM2-S on the side of the support, SUP, on a detachable, re-attachable basis. Then he/she can wrap the end of the strap around the outer surface of the strap to make a U-turn and adhere the adhesive tape ADT from the end of the strap to the rear surface of the strap, or by use of a connection means ATM2.

Importantly, in the model where the layer of adhesive, ADH, is placed on the lower side of the strap, STR, (instead of being on the upper surface of the strap as shown), the user will wrap the strap over the support. Then the adhesive tape from the free end of the strap will be adhered to the outer surface of the body of the strap, STR.

Based on the experiments of this applicant, this process takes only about 15-20 seconds of time and makes a very stable and easy method of wrapping a wound with the use of one hand only.

FIG. 4 shows the side view of a wound dressing unit shown at FIG. 3. This figure shows the cross-cut side view of the support, SUP, and the strap, STR, attached to it on left side. The support, SUP, has zones of the attachment means: ATM2, on its upper surface which is made from hook type of hook-loop-fastener (VELCRO TM). In this view the ATM2-B and ATM2-S are shown. These zones allow complementary pieces such as the body of the strap and Band-B to be attached to them on a detachable, re-attachable basis.

The piece of gauze pad, GP, is attached to the lower surface of the support, SUP, by a detachable, attachment means, ATM, which can be a layer of adhesive. This allows the pad to be removed and replaced by a similar or another piece. This allows a soiled gauze pad to be exchanged with a fresh one.

The free end of the strap, STR, shown on the left side has a patch attachment means: ATM2 made from hook type of hook-loop-fastener (VELCRO TM). This patch allows the free end of the strap, STR, to be attached to the outer surface of the body of the strap, STR on a detachable, re-attachable basis. The cross-cut of the adhesive tape, ADT, is shown in this figure and has a layer of adhesive, ADH, shown with a short, dotted-line. It has a protective cover, PC, that is folded to allow removal without being touched by the gloves.

Figure 5:
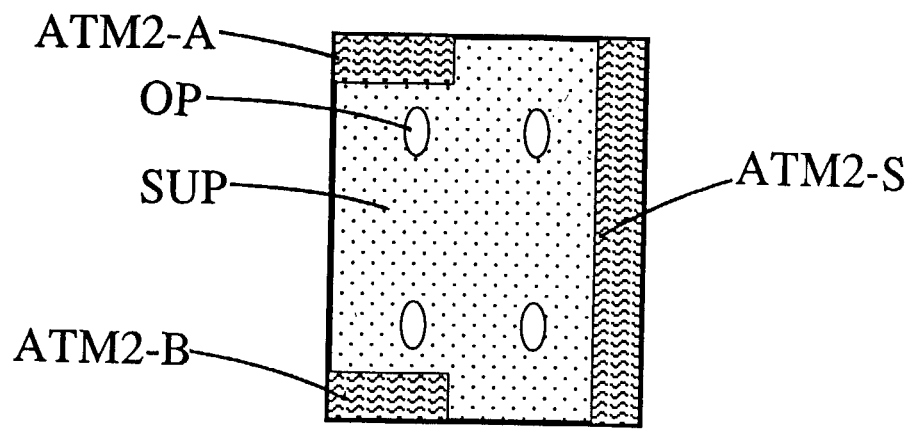
FIG. 5 shows the support piece from FIG. 1 in more detail.

FIG. 5 shows the front view of a support unit, SUP, which has a non-stretchable body (may in some cases be stretchable) and openings, OP, that allow air and gasses to pass through. It has the zones of the attachment means, ATM2 made from hook type of hook-loop-fastener and which are farther specified by ATM2-A, ATM2-B and ATM2-S. Importantly, many of the supports used for the units in this application use a material that is now commercially available and has an outer surface made from a layer of loop-fastener attachment means, ATM1, an inner surface made of a soft lining that stands on the skin and a thin layer of foam in between. The use of this material with zones of hook-fastener attachment means, ATM2, gives the option of attaching straps with both loop-fastener body and hook-fastener end pieces. Also importantly, the double-sided, hook-fastener pieces such as the one shown at FIGS. 18 and 18A may be used with these units with or without adhesive zones. Importantly, a double-sided ATM2 piece will allow a strap and support that have a body with loop-fastener to be attached to each other on a detachable, re-attachable basis.

Importantly, instead of the zones of the attachment means, ATM2-A and ATM2-B, the unit may have a second long zone of the hook-fastener attachment means, such as the zone ATM2-S, on the left border of the support. This allows the attachment of the strap, STR or the bands BAND-A and BAND-B to the support to occur.

Figure 5A:
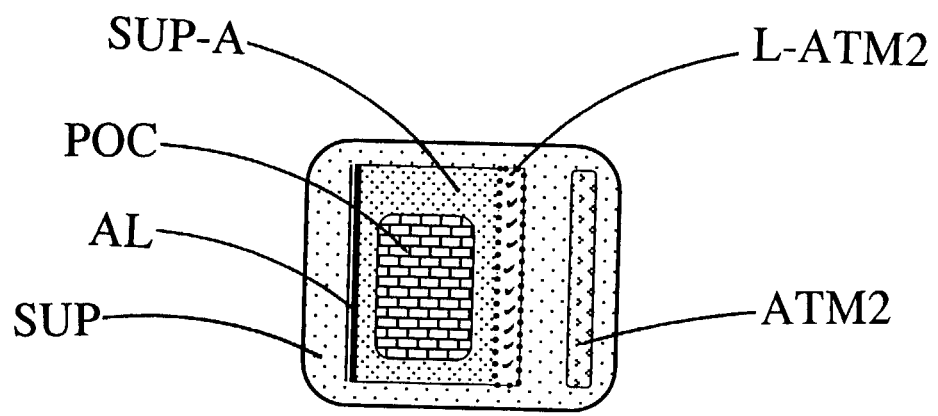

FIG. 5A shows the front view of a support unit which is similar to the model shown at FIG. 5, except the support is made from a body with an outer surface made from a layer of loop-fastener attachment means, ATM1. This support, SUP, has a second support piece, referred to as Support A, SUP-A, that is attached to the body of the first support along the Attachment Line, AL. The free end of the support A, SUP-A has a zone of hook-fastener attachment means, L-ATM2, that allows the Support A, SUP-A, to attach to the outer surface of the first support on a detachable, re-attachable basis. The advantage of the second support, SUP-A, is that it allows tubings, wires, suction bulbs, etc., to be kept between these two layers securely. The outer surface of the second support, SUP-A has a pocket, POC, of its own that allows a suction bulb to be placed inside it as well, if needed.

This unit will have a strap that will be attached to one side of support, SUP, and the free end of the strap will attach to the attachment means, ATM2, of this support as explained previously. These units may be placed in the arm, around the limb, chest, abdomen, etc.

Figure 6:
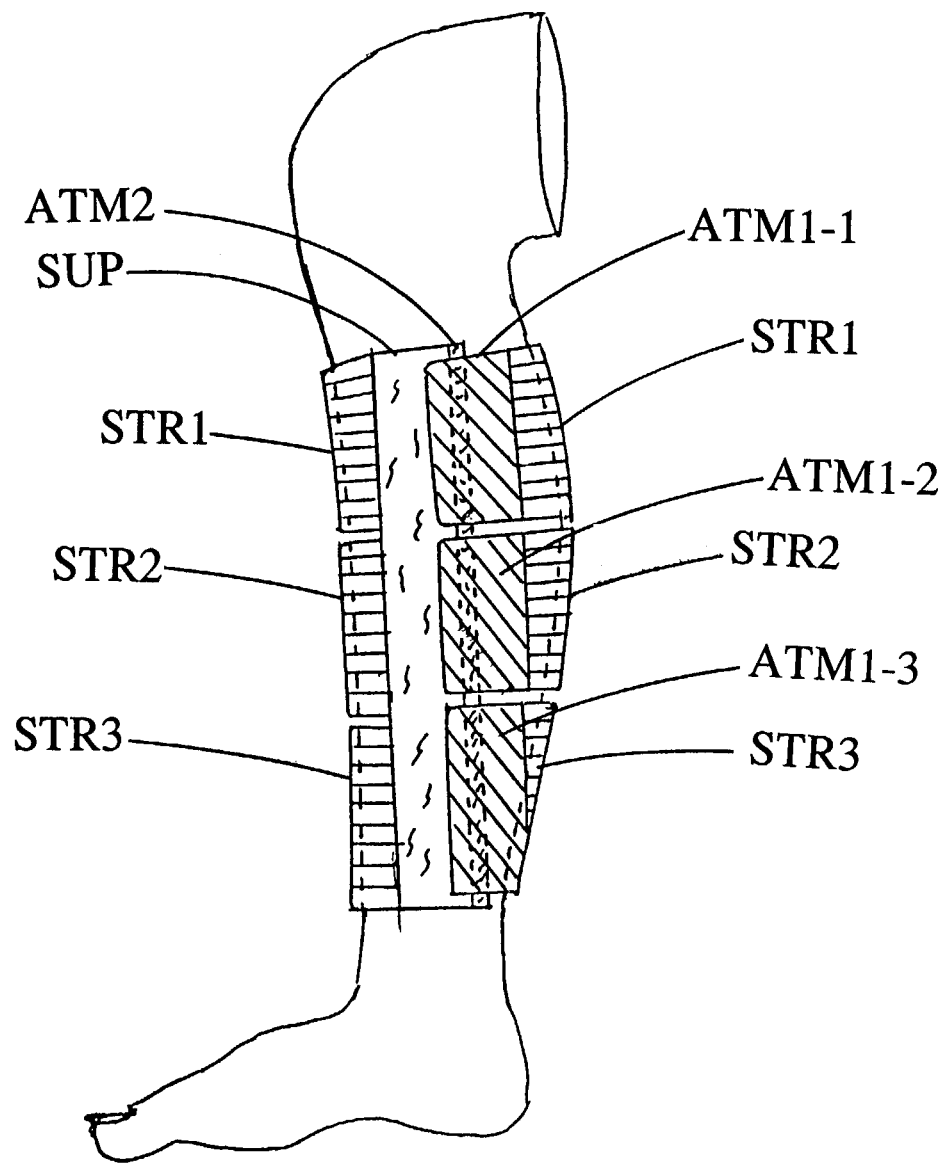
FIG. 6 shows a support unit for the leg, in which one end of the straps is fixed on the border of the support.

FIG. 6 shows the general view of a support unit similar to the unit shown at FIG. 1, except this unit is modified for use on the leg area and to support the legs as well. This unit allows secure and easy dressing of the leg without the need for adhesive tapes. In this model the support, SUP, has a long, rather rectangular shape and covers the front of the leg, or the wound site. The support, SUP, is shown in more detail at FIG. 6A. It has a long zone of hook-type, attachment means on its right border that allows pieces made of loop-fastener attachment means, ATM1 to be attached to it on a detachable, re-attachable basis. The left border of the support unit, SUP, is attached to three straps: STR1, STR2 and STR3. These straps are attached to the support unit on a permanent basis although importantly, they may be attached to the support on a detachable, re-attachable basis. These straps are sized to wrap around the leg on its upper, middle and lower part. These straps will wrap around the leg and their free ends, attach to the support, SUP, by use of loop-fastener attachment means, at their ends shown at ATM1-1, ATM1-2 AND ATM1-3 which are respectively attached to the end of the straps STR1, STR2 AND STR3. The applicant had made this method for dressing/supporting the legs and thighs in a very practical, adjustable fashion. In this model the straps are also made from one or two layers of (LYCRA TM) and the support means are made from vinyl, although they may be also made from any other materials such as fabrics or any other proper manmade materials. The support may have openings in it to allow sweat and air to pass through. The support also allows a gauze pad or a long, removeable layer of lining, shown at LIN, in FIG. 6A, or a pad, to be placed under it. The lining or pad prevents irritation, and also allows application of pressure and/or medication to be applied as well.

Importantly, this unit allows electrical leads/pads to be held in place for a programmed stimulation of the leg muscles and tissues. This will be done for various reasons such as prevention of muscle weakness or of phlebitis.

Importantly, these units are very valuable, since it allows the pressure in different segments of the leg to be adjusted by this unit. Also importantly, the unit can be removed and applied easily and can be placed over the regular stocking and pants as well.

The lining will be attached to the support, SUP, on a detachable, re-attachable basis, to allow washing or exchanging. This model can be made to extend to the thigh area as shown in this applicant's previous applications. In this model a couple of straps will attach the thigh piece to a waist strap in order to prevent it from sliding.

Importantly, the straps of this unit may be attached to the body of the support unit independently, by having one end of the straps be attached to one border of the support and the other end attached to the other border of the support both on a detachable, re-attachable basis. This was shown by the applicant in his previous models and applications to USPTO.

Figure 6A:
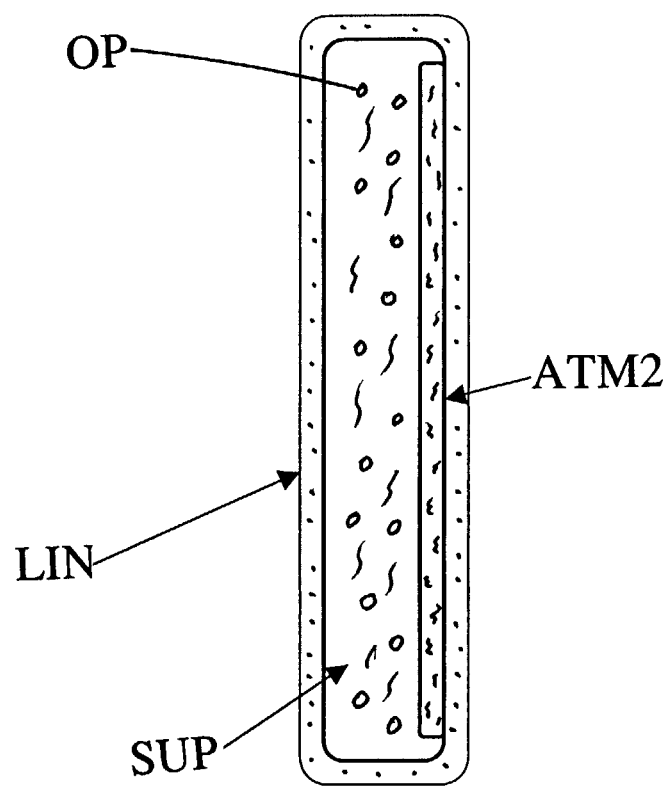
FIG. 6A shows the support piece from FIG. 6 in more detail.

FIG. 6A shows the general view of the support unit shown at FIG. 6. In this figure the body of the support is shown at SUP, and it has openings, OP, a long zone of hook-fastener attachment means, ATM2, which is shown in its right border. A layer of lining, LIN, is attached to the rear surface of the support, SUP, and extends from its borders. The lining, LIN, is attached to the body of the support on detachable, re-attachable basis to allow the exchange.

Figure 6B:
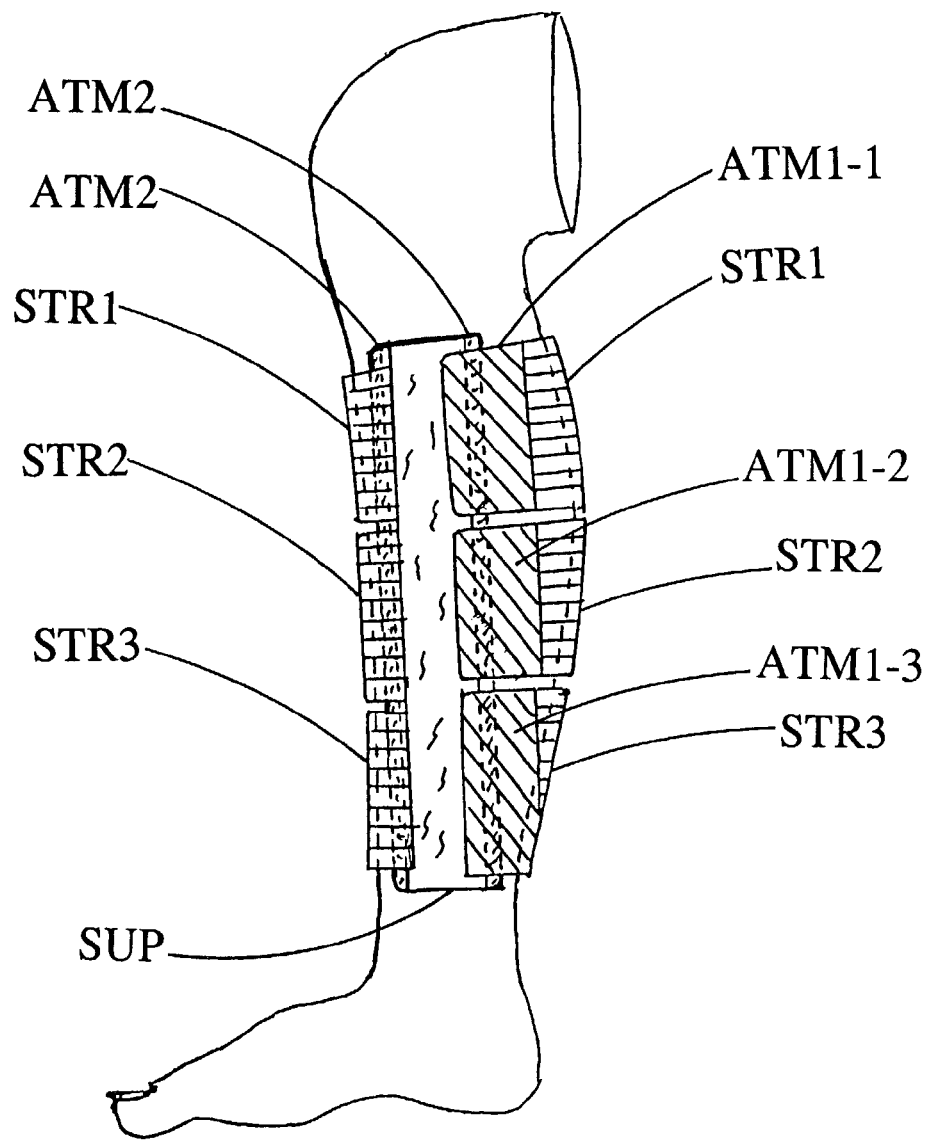
FIG. 6B shows a support unit for the leg, in which both ends of the straps are free and attach to the border of the support on a separable basis.

FIG. 6B shows schematically a support unit similar to the unit shown at FIG. 6 placed on a leg. This unit has three straps which each have straps with their own attachment means and that are attached to the support, SUP, on a detachable re-attachable basis. The support of this unit has one long zone of hook-fastener attachment means, ATM2, in the right and left border of its body. This model allows the effective length of the straps to be adjusted from both ends of the straps. The three straps are further marked as STR1, STR2 AND STR3, and are attached to the support unit by use of the loop-fastener attachment means, ATM1, which are part of the free ends of the straps. When the straps have the loop-fastener attachment property of their own, they will attach to the support themselves. These straps are properly-sized to wrap around the leg on its upper, middle and lower part. They can be attached to the support, SUP, by use of the pieces of loop-fastener attachment means at their ends shown at ATM1-1, ATM1-2 AND ATM1-3 which are respectively attached to the one end of the straps STR1, STR2 AND STR3. The other ends of the straps have similar attachment pieces as well, which are not marked in this figure to prevent a crowded picture. In this model the straps are also made from one or two layers of (LYCRA, TM) and the support means is made from clear vinyl, although it may also be made from any other materials such as fabric or any other manmade material.

Figure 6C:
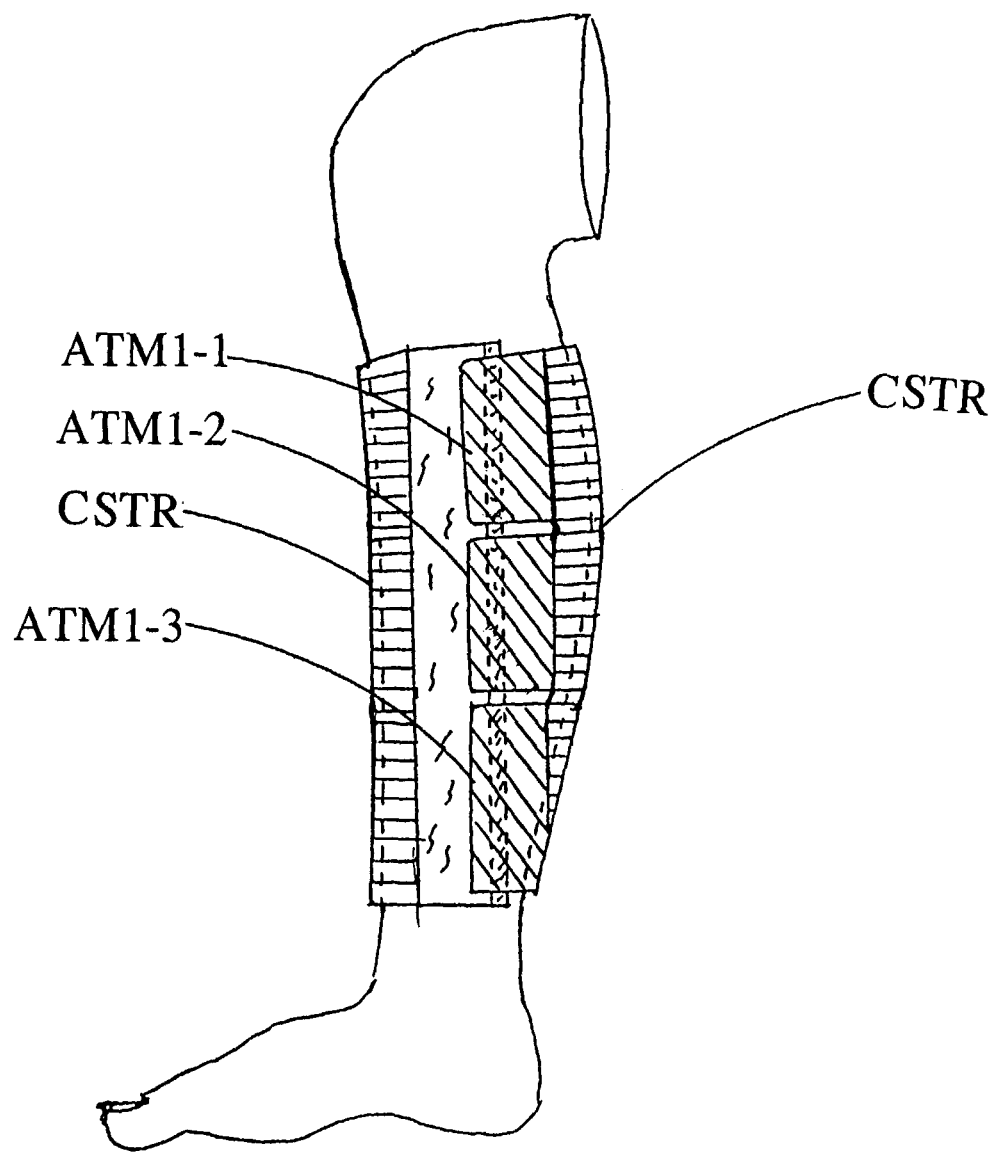
FIG. 6C shows a support unit for the leg which consists of a single wide strap that has multiple separate attachment means.

FIG. 6C shows schematically the general view of a support unit similar to the unit shown at FIG. 6, except in this unit the body of the strap is made from a non-segmented fabric, marked CSTR. This fabric is attached to the body of the support along one of its borders and continues to wrap around the leg, but ends with three separate loop-fastener attachment means, ATM1-1, ATM1-2 AND ATM1-3. The end pieces allow the end units to attach to the hook-fastener attachment means, ATM2 from the support, SUP, on a detachable, re-attachable basis. Importantly, the value of this model is that the continuous body of the strap does not leave an open area or a line of compression on the legs. Importantly, this unit is also chosen to show that a strap may have more than one ending.

Figure 7:
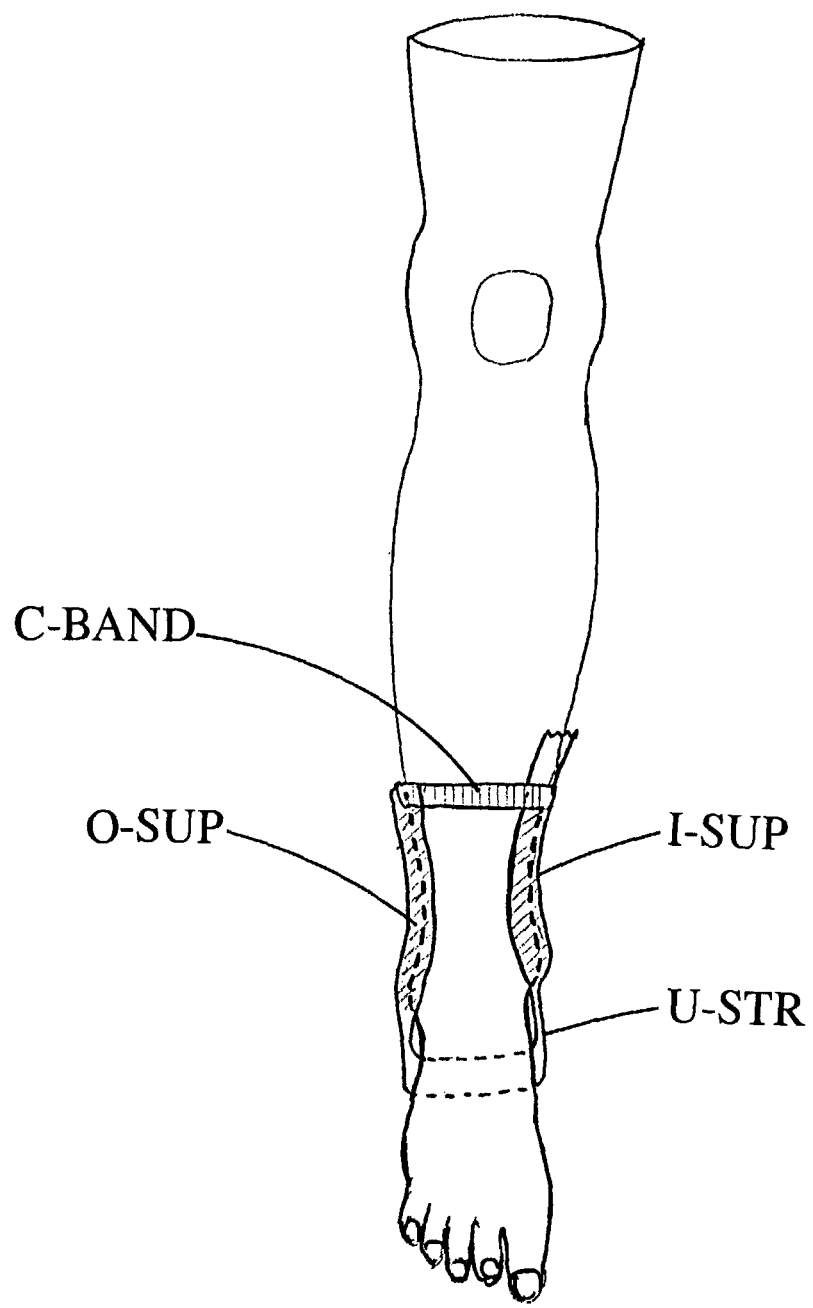
FIG. 7 shows a support unit for the lower leg/ankle area.

FIG. 7 shows the front and side views of a support unit similar to the unit shown at FIG. 5, which is modified by adding a U-shape extension to it. This unit is designed to support the middle and lower ankle area in both sides of the ankle, inside and out, and allows the compression of those areas. In this model a support piece similar to the support, SUP, shown at FIG. 5 or an extension of the support of the leg support is utilized and shown as the inner support, I-SUP, and functions to compress the inner part of the ankle. This support, I-SUP, moves down and covers the inner ankle and connects to a piece of an elastic strap shown at U-STR. This U-strap makes a U-turn under the foot and attaches to another non-stretchable support that functions as the outer support, O-SUP. This compresses and supports the outer ankle area and has a band, C-BAND, which is an elastic strap that wraps around the lower leg or ankle area and holds the O-SUP in place. The C-BAND allows a wider strap, such as STR3, shown at FIG. 6B to wrap around the I-SUP AND O-SUP keep these supports in place, squeezing the tissue in between them. The importance of this unit is:

A. The U-shaped support means supports the middle, lower and lateral part of the ankle and allows the compression of the tissues in these areas. The importance of this unit is that it allows dressing and compression of the tissue and vessels on the lower inner ankle-foot area to occur for a better result and in a measurable with placement of a balloon connected to a gauge and adjustable manner. The use of this unit is in vascular problems, particularly in venous insufficiencies of the legs, where compression of vessels for decreasing the inner pressure of the vessels and prevention of extravasation of fluid in this area is needed. Please note that in order to prevent confusion, the upper parts of the unit are not shown in this figure.

Importantly, in some cases there is a need for further compression of the lower leg to raise the amount of pressure on the tissue. In such cases the inner support, I-SUP and the outer support, O-SUP, are made from rather rigid pieces such as a shaped polymer or metal that are connected to each other in the lower side by a strap. The position of this strap on the supports is adjustable and allows the distance of these two inner support, I-SUP, and the outer support, O-SUP, to be adjusted. Importantly, the outer surfaces of the inner support, I-SUP, and the outer support, O-SUP, have attachment means, such as hook-fastener attachment means, ATM2. This allows a wider, horizontal strap or two straps similar to one shown at C-BAND to wrap around the lower leg and hold the I-SUP and the O-SUP in place to further compress the tissues in this area. This combination can be used as a separate unit, or in combination with the leg support. Importantly, the rigid supports can be a pre-shaped or alternatively made from a material which accepts the shape of the area after placement. Pieces of shaped foams or pads may also be placed between the wound dressing and these supports. A flat, fluid-filled balloon attached to a measurement unit may be placed between the support and lining to monitor the pressure in the wound.

Figure 7A:
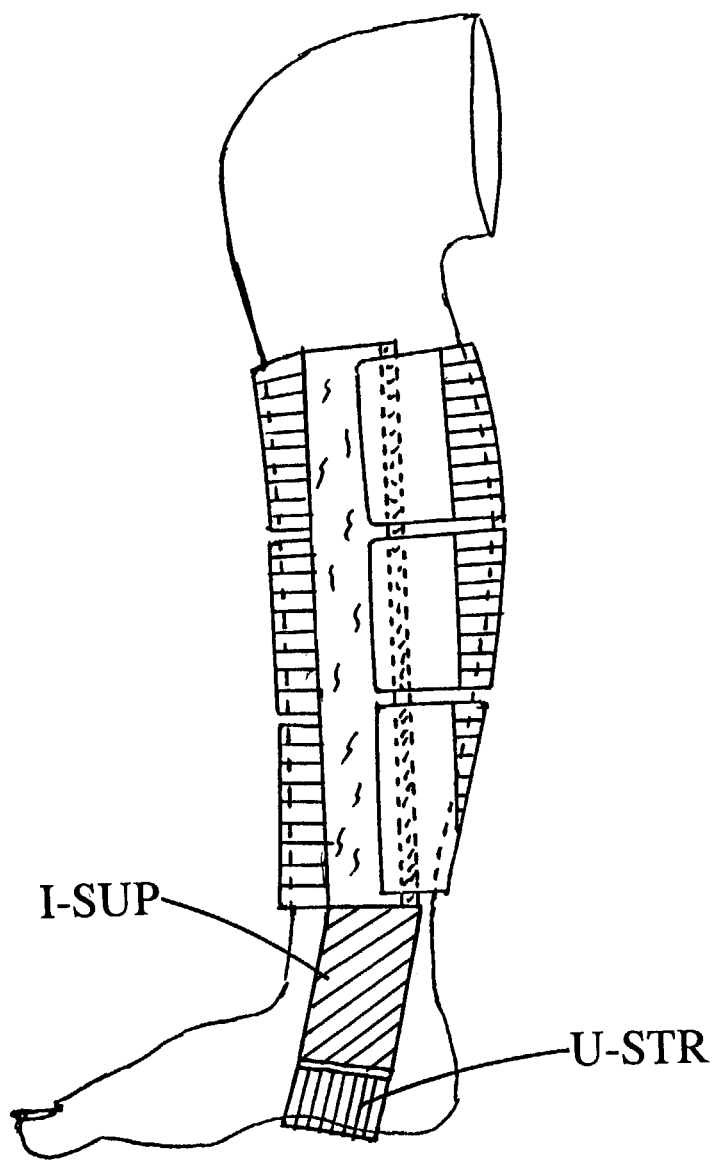
FIG. 7A shows a combination of the units from FIG. 6 with the unit shown at FIG. 7.

FIG. 7A shows a support unit for the leg as shown at FIG. 6C, except this figure shows a U-shaped extension attached to it. In this figure the support, shown at FIG. 6C, has an extension which will function as the inner support, I-SUP. This piece moves down and covers the inner ankle and then connects to a piece of strap shown at U-STR. This follows a model which was shown at FIG. 7.

Figure 8:
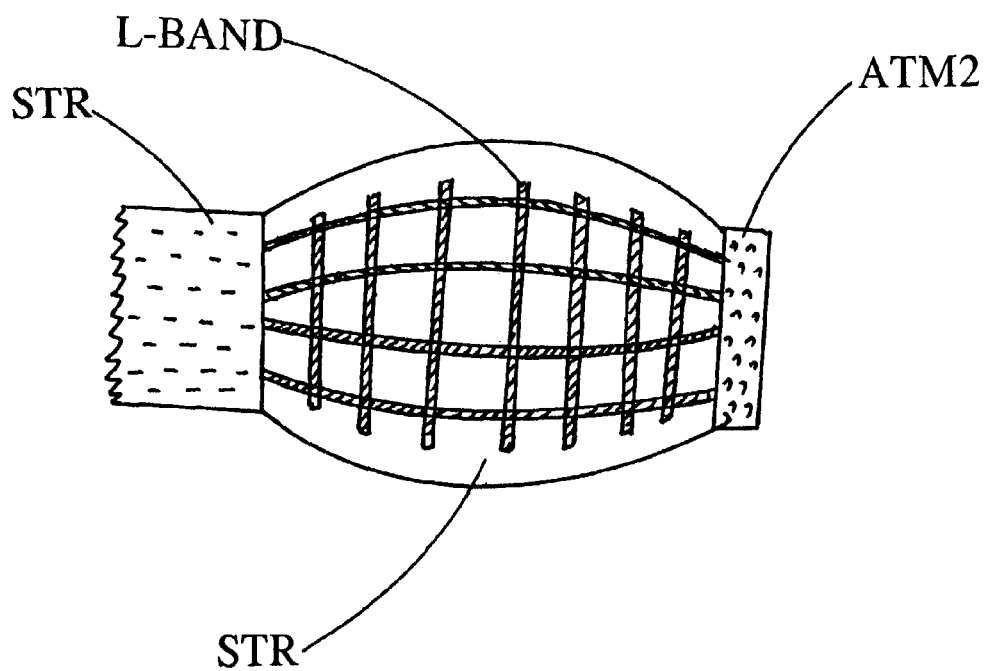
FIG. 8 shows a conformed strap for use in special places such as the knee.

FIG. 8 shows the front view of a special stretchable support unit made from shaping the same material used for the strap or the LYCRA (TM). Here, the Lycra is modified with use of bands made from materials such as latex as shown at L-BAND. The shaping of this stretchable material or the use of sewing techniques allow an elastic, shaped support to be made. Such a support is useful in areas with a particular shape and function, such as knees, ankles, elbows, toes, etc. This shaped, stretchable support allows better handling and placement of these units. Importantly, the following advantages are also available:

a. In this method the support has an elastic body that will be pulled to keep it in place with a comfortable tension. This mild, comfortable tension is an important property for use in these areas.

b. The support unit stretches and conforms to some degree and accepts the shape of the area. Also, such a body allows this body of the support to change with change of the wound areas such as over joints, knees, ankles, hips, elbows with extension and closure.

c. The inner part of the support is a soft, non-irritant fabric and does not cause skin reaction.

d. On the scalp it allows an easy dressing of the wound.

e. Importantly, the side where the strap is attached stretches in both direction and allows this unit to fit a shaped area, such as the scalp. A transverse strap allow this unit to be further stable on the scalp. This will make a cross-shaped unit.

In this figure the attachment means of the support is shown at ATM2 and the strap at STR. A D-Ring may also allow the strap to be adjusted.

Figure 9:
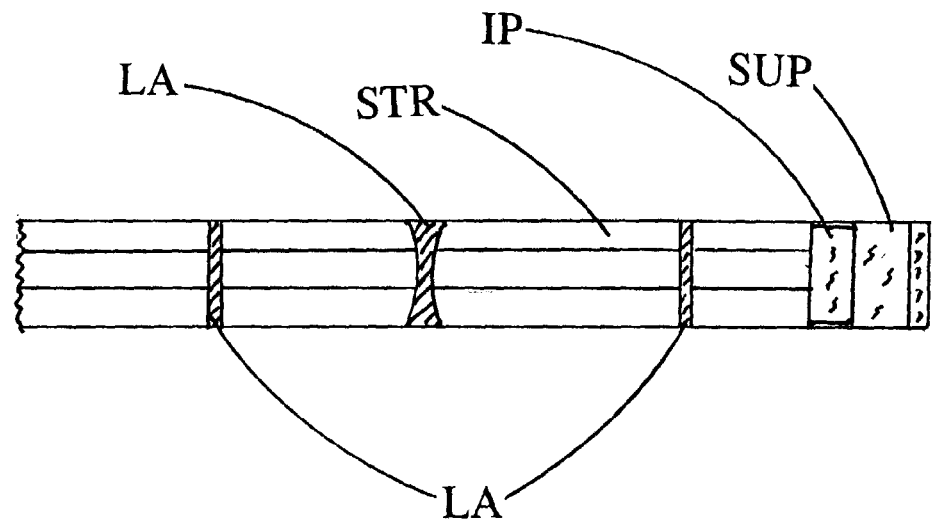
FIG. 9 shows a support unit and a strap where the body of the strap has materials such as latex or shaped means on it.

FIG. 9. Shows a long strap that is attached to a transparent support, SUP. This figure also illustrates two important parts:

1. a transparent pocket for placement of information, here referred to as the Information Pocket, IP which is on the support, SUP or on the strap. The Information Pocket, IP, allows a piece of paper, consisting information to be placed inside the pocket. This information may be, for example, time of the use of the dressing, medication underlying IV line, or other information about the person using the unit, etc., and can be exchanged as needed.

Importantly, the information pocket, IP, may be placed on the wall of the strap to be part of the wall or simply attached to it.

2. Importantly, the body of the straps, STR, may have zones of materials such as latex, LA, in or on it in order to allow the shape of the strap to be conformed or modified to a desired shape. It can be used to prevent curling of the strap, etc. The shape, width, thickness, materials utilized, and other characteristics of these zones may vary.

Figure 10:
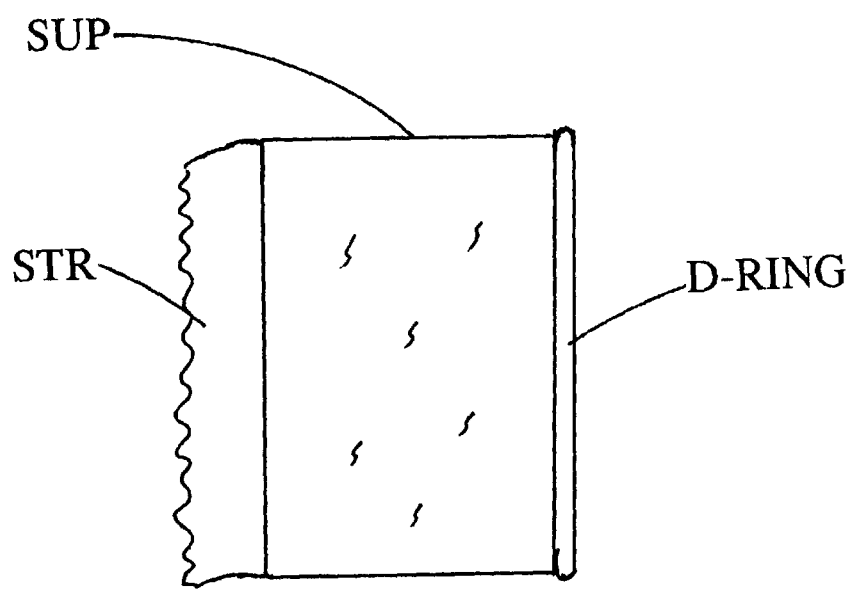
FIG. 10 shows a D-Ring on the side of the support to allow the strap to make a U-turn.

FIG. 10. Shows schematically the use of D-Rings with the support unit. In this figure a transparent support, SUP has a D ring, D-RING on its right side that allows the strap of the unit to go through, make a U-turn, and attach to its own surface. This is another method of adjusting the length of the strap as mentioned in the text.

Figure 11:
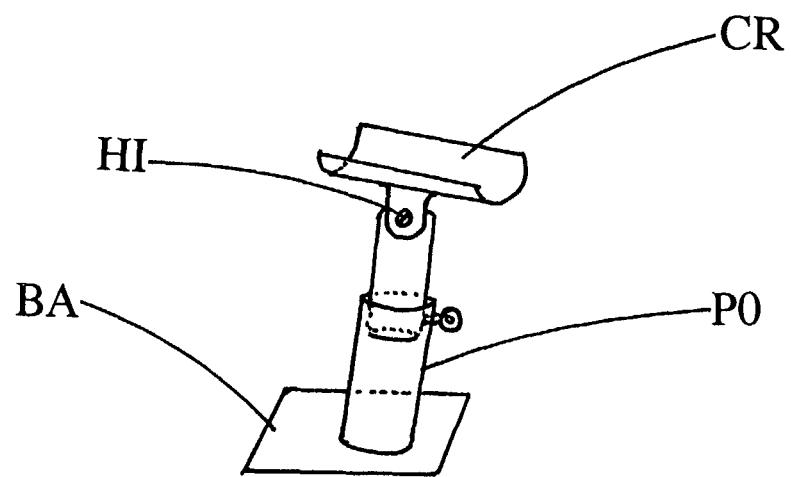
FIG. 11 shows a stand to allow the supports to be placed and used by one hand only.

FIG. 11. Shows schematically a cradle, CR, on a stand that allows a limb to be placed on it. The angle and height of the cradle can be adjusted by means connected to the base, BA. The height can be adjusted by control of the height of the pole, PO and the angulation by the hinge, HI. This unit allows a strap or the support part of the support unit, shown at FIGS. 3-4 to be placed on the cradle of this unit and be attached to it by use of a weak adhesive or by a detachable, re-attachable means. Thus, the combination allows the user to place the support on a limb with one hand and adjust its size and tension.

Figure 12:
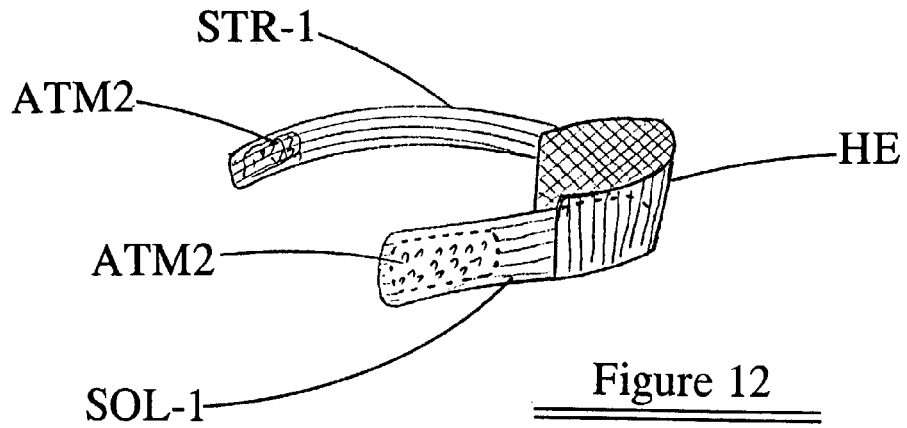
FIG. 12 shows a support for the heel.

FIG. 12 shows a general view of the rear piece of a support unit designed for use for the supporting of the wounds on the heels and toes. In this figure the piece that stands on the heel is shown at, HE and it has a lower sole, SOL-1 that has a hook-fastener attachment means, ATM2, on its surface. This piece also has a strap, STR-1 with a zone of hook-fastener, attachment means, ATM2, on its end this piece complements the piece shown at FIG. 13 to make a unit shown at FIG. 14.

Importantly, these heel and toe pieces which may be made from shaped lycra (TM) or similar fabric, with use of latex material as mentioned, so that this combination will:
a. Be soft, non-irritant and comfortable.
b. Allow the unit to be pulled to accept the form of the underlying area and fit well.
c. Allow one size to be used in many patients.
d. Allow the pieces to be placed inside one another and so that many of them, such as 15-20 at a time, may be placed inside one box, thus reducing storage size.
e. Allow the patients themselves to adjust the length of the unit as needed.
f. Importantly, both the heel and front pieces may have a cut with a strap on their lengths to allow their width to be adjusted as well. The strap will hold the open area in control.
g. Importantly, both the heel and front pieces themselves may be made from two pieces to allow the width to be adjusted as one piece can be attached to the other one along a zone of attachment of a detachable, re-attachable basis.
h, Importantly, these pieces may be made from other shaped materials.

Importantly, the attachment means will be complementary and one attachment means, ATM, will be faced with a complementary attachment means on the other side. Or, the body of the shaped areas will function as the complementary attachment means. This method allows, for example, the attachment means in the straps to be hook-fastener attachment means, ATM2, to be attached to the surface of the body of the heels made from loop-fastener attachment means.

Figure 13:
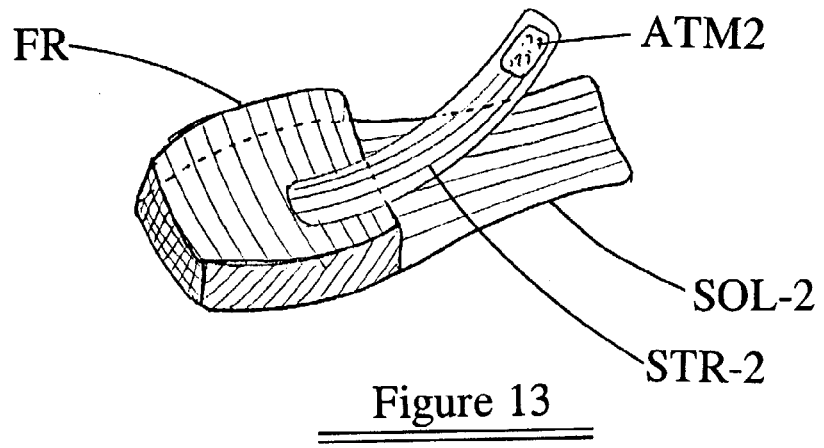
FIG. 13 shows a support piece for the front of the foot.

FIG. 13 shows the general view of the front piece of the support unit shown at FIG. 12. In this figure the front piece, FR, also has a sole, SOL-2, that allows the hook-fastener attachment means, ATM2, from the rear piece shown at FIG. 12 to attach to its surface on a detachable, re-attachable basis. This piece has a strap with a piece of hook-fastener attachment means on its end. The front and rear pieces of these units are made from shaped materials.

Figure 14:
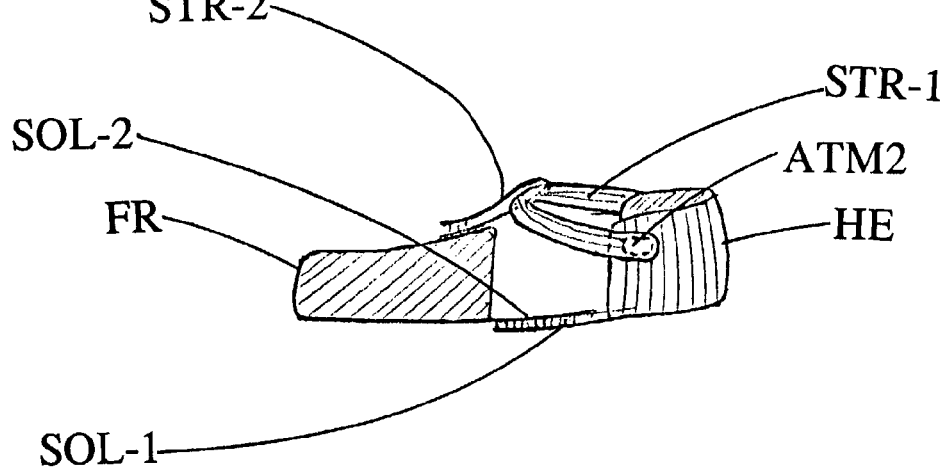
FIG. 14 shows a combination of the units shown at FIGS. 12 and 13.

FIG. 14 shows schematically the general view of the support unit for the heels and toes made from the combination of rear piece shown at FIG. 12, and front piece shown at FIG. 13. In this figure, sole, SOL-1, from the rear piece is attached to SOL-2 from the front piece on a detachable, re-attachable basis. Importantly, this allows the length of the unit to be adjusted. The strap STR-2 holds strap STR-1 from the rear piece and attaches to its own surface by the attachment means on a detachable, re-attachable basis. The strap STR-1 from the rear piece, HE, attaches to the body of the rear piece, HE, on a detachable, re-attachable basis.

Figure 15:
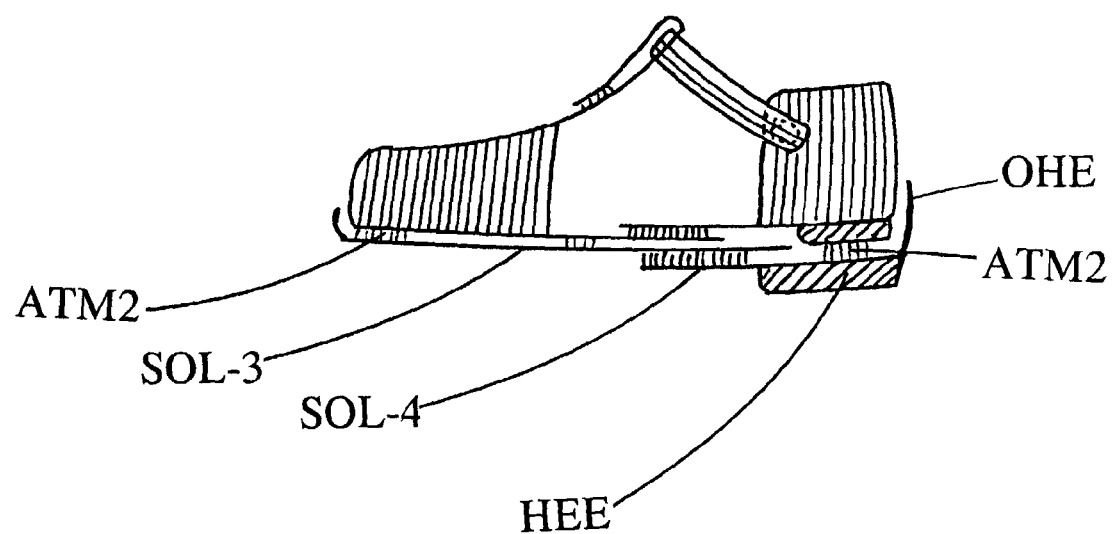
FIG. 15 shows a unit to be used as an adjustable outer cover for the unit shown at FIG. 14.

FIG. 15 shows schematically a support unit for the heels and toes, made from the combination of the unit shown at FIG. 14, which is placed inside an outer piece that functions as the body of a shoe. The outer piece is made from a front sole shown at SOL-3 that is attached to the SOL-4 from a rear piece, OHE on a detachable, re-attachable basis. The combination is attached to the piece shown at FIG. 14 by attachment means between them.

This combination has the advantage of allowing an adjustable piece be used for use both in and out of the house. The outer piece will be removed inside the house and used when leaving the house.

The use of heel and foot protector with these units:

Importantly, these units allow pieces of foam to be attached to their surfaces in order to prevent bed sores in these areas. For this purpose, shaped sponges will be attached to these pieces and prevent pressure sores. The shaped sponges may have open spaces in particular pressure areas to avoid pressure to those sensitive areas. It is important to note that the use of soles allow the sponges to be kept in place securely and not to rotate as commonly occurs.

Figure 15A:
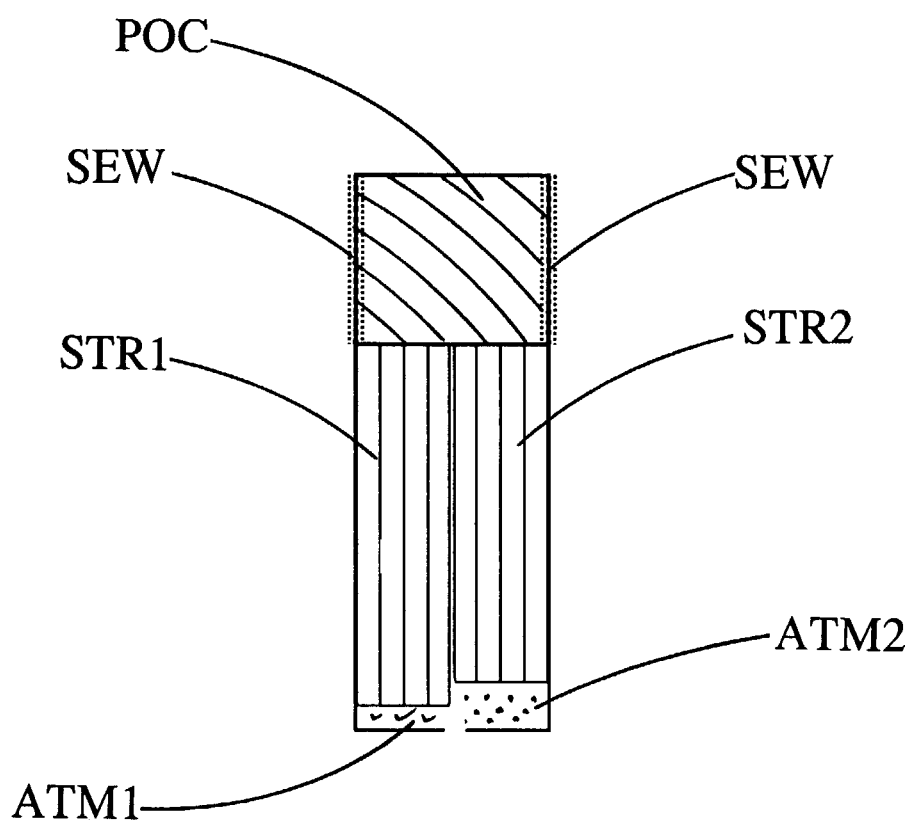
FIG. 15A shows a support unit for the front of the foot.

FIG. 15A shows schematically the general view of a simple support unit for the dressing of the toes. This unit has a pocket made from a combination of a front and rear wall that are attached to each other along their borders shown at lines, SEW. In this particular model the fabric is folded so the front border is closed as well. The rear wall of this unit has two elastic straps, STR-1 and STR-2, which are made from Lycra and are attached to the body of the rear wall. The free ends of these straps have a complementary attachment means made from loop-fastener attachment means shown at ATM1 and hook-fastener attachment means, ATM2 respectively. Please note that one of the attachment means will be in front of one of the straps and the other will be on the rear surface of the other strap. This method will allow the end of these straps to attach to each other on a detachable, re-attachable basis.

At the time of use:
a. The pocket of the support, POC, will be placed in front of the foot and will cover the toes and its dressings. In this position the straps will be under the sole.
b. The strap, STR1, will be pulled to wrap around the heel to move up and cover the front of the ankle. This will be kept in position to allow the end of the other strap to attach to it.
c. The second strap, STR2, will be pulled to wrap around the heel and move up from the other side of the ankle so that its free end will attach to the attachment means, ATM1, from the strap, STR1.

This method will make a secure and simple means of holding the dressing of the toes in its place which is commonly difficult.

The support may be made from:
1. Elastic fabric
2. A regular fabric
3. A thicker unit such as body of the supports as mentioned.

4. Various materials may be used.
5. The attachment of the straps to the body of the support may vary.

However, making this unit from the LYCRA (TM) makes a very nice comfortable unit that has many advantage such as:
  a. A support with an elastic body that will be pulled to keep it in place with a comfortable tension. This mild, comfortable, tension is an important property for keeping the dressing in place.
  b. The support unit stretches and conforms to some degree and accepts the shape of the area.
  c. The support is a soft, non-irritant fabric and does not cause skin reaction.

Figure 16:
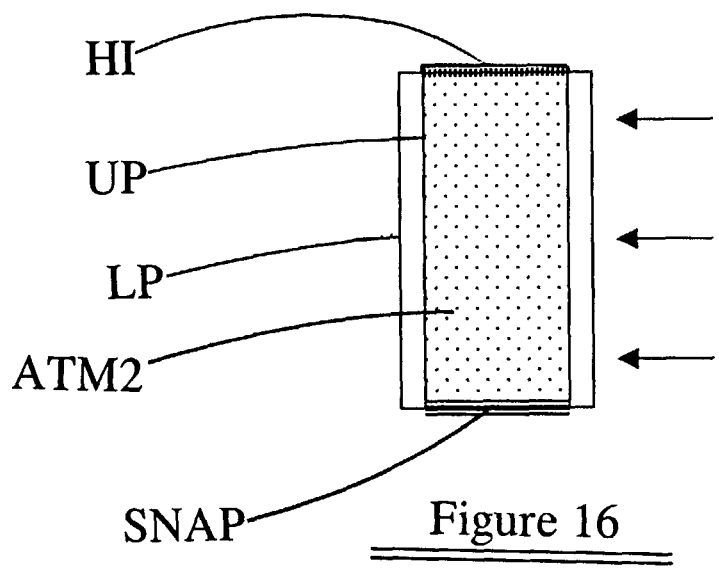
FIG. 16 shows the top view of a buckle system to allow the length of the strap to be adjusted.

FIG. 16 shows the top view of a buckle means designed to allow the length of the strap to be adjusted and a more durable, convenient unit for use with these units. This unit allows the length of the strap to be adjusted initially and yet allow some further adjustment after the initial placement of the strap on the support. This buckle consists of a lower flat piece, LP, and an upper flat piece, UP, that are hinged at hinge, HI. The other end of the upper piece, UP, will be snapped to the lower piece, LP, by the snap, SNAP. The snap allows the upper piece to be opened and closed along the hinge, HI. The upper piece, UP, has a series of spins, SPIN, on its lower surface that, when the buckle is closed, allow the strap to move in a one way direction as the arrows point and not be pulled back. The upper surface of the upper piece, UP consists of attachment means, ATM that allows the end of the strap to be attached to it on a detachable, re-attachable basis.

Importantly, the spins may be placed on the upper surface of the lower piece, LP.

The lower surface of the lower piece, LP, consists of a loop-fastener attachment means, ATM, that allows it to be attached to the hook-fastener attachment means of the surface of the support on a detachable, re-attachable basis.

At the time of use the strap will be pulled in the direction of the arrows and will be placed between the upper, UP, and lower pieces, LP. Then it will make a U-turn along the border of the upper piece, UP, and attach to the surface of the upper piece, UP, by itself or with the help of a matching attachment means or weak adhesive, with the extra length cut after length adjustment. The free end of the strap will finally be attached to this buckle and the buckle attached to the support, SUP, on a detachable, re-attachable basis. The extra length of the strap will allow its length to be adjusted and the position of the buckle on the support allows the effective length of the strap to be adjusted as well. The snap, SNAP, allows the upper piece, UP, to be opened and the strap be moved back and forth for the length adjustment.

Figure 17:
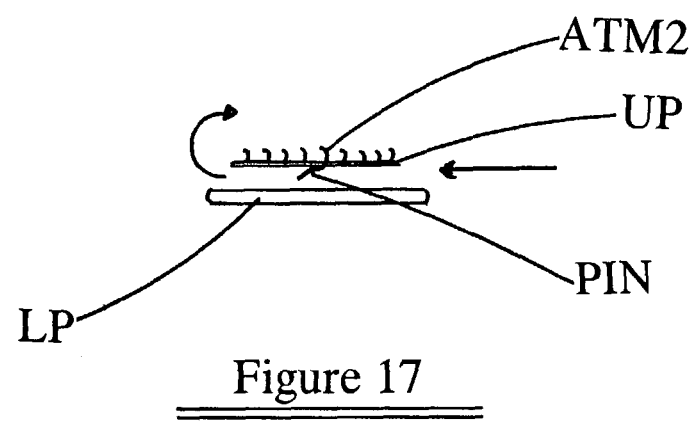
FIG. 17 shows a vertical, horizontal, cross-cut view of the unit shown at FIG. 16, that shows a lower wall, an upper wall and a space in between through which the strap goes.

FIG. 17 shows a vertical, horizontal, cross-cut view of a buckle piece shown at FIG. 16. In this figure the lower flat piece, LP, is shown and its lower surface consists of attachment means, ATM. The upper surface of the upper piece, UP, has hook-fastener attachment means, ATM2, that allow the end of the strap to be attached to it on a detachable, re-attachable basis.

The lower surface of the upper piece, UP, has the spin, SPIN. At the time of use the strap will be pulled in the direction of the straight arrow, and then the unit will be snapped and the rest of the strap will make a U-turn in the direction of the curved arrow to attach to the attachment means of the upper surface of the upper piece, UP.

Figure 17A:
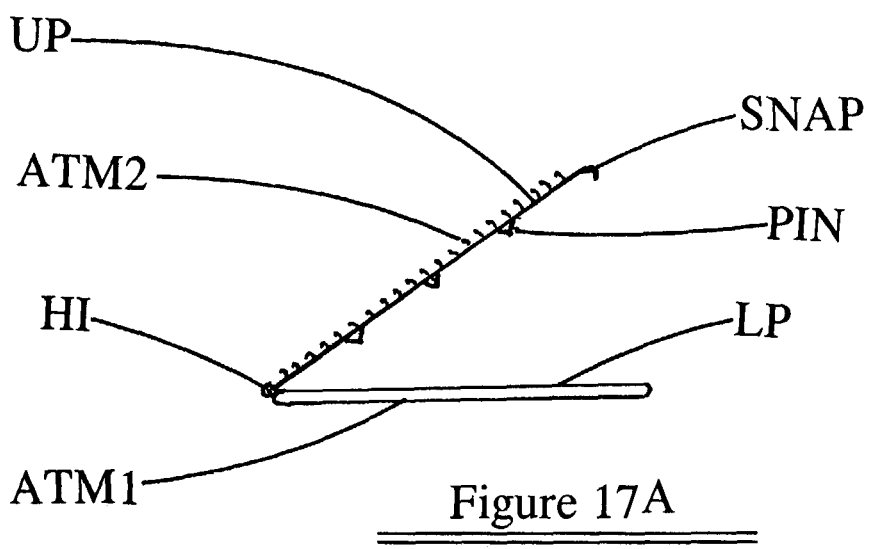
FIG. 17A shows a vertical, longitudinal, cross-cut view of the unit shown at FIG. 16. It shows a lower wall and an upper wall hinged together at HI.

FIG. 17A shows a vertical, longitudinal, cross-cut view of a buckle piece shown at FIG. 16. In this figure the lower flat piece, LP, is shown and its lower surface consists of attachment means, ATM. The upper piece, UP, is hinged to the lower piece, LP, at hinge, HI. The upper surface of the upper piece, UP, consists of attachment means, ATM2, the spin, SPIN, is shown at the lower surface of the upper piece, UP, and the snap, SNAP, is also shown.

Figure 18:
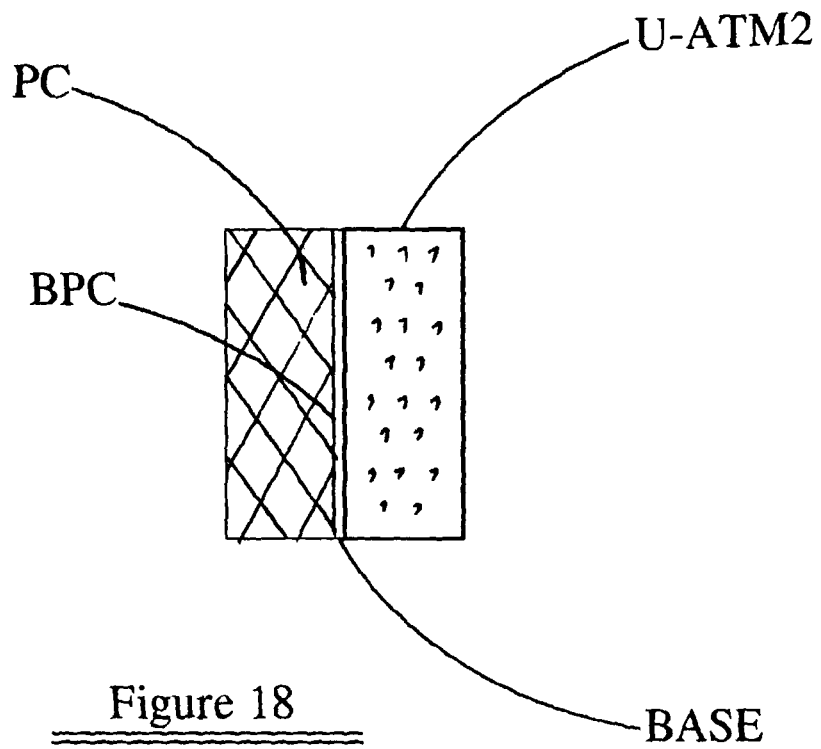
FIG. 18 shows an end piece unit with a double-sided attachment means that allows extra strap to be cut and to attach the remaining free end to this piece.

FIG. 18 shows the front view of an end unit, designed to allow the length of the strap to be adjusted. This unit has a rectangular, flat base, BASE, made from a layer of fabric with a zone of hook-fastener attachment means on its right side, ATM2, placed on its upper and lower surfaces. Here, the upper zone of attachment means, U-ATM2 is shown on the right side. A similar zone on the left side is made with a layer of adhesive on it, shown at ADH, at FIG. 18A, which is protected by a protective cover, PC. The inner edge of the protective cover is shown at BPC. The lower surface of the base in the right side also has attachment means, L-ATM2, best shown at FIG. 18A. This unit gives significant advantage and will allow the length of the strap to be adjusted for many units such as the heel and shoulder and other units.

At the time of use:
1. Initially this piece will be attached in a proper position to the body of the outer surface of the support, SUP.
2. Then the strap will be pulled to attach to the ATM2 zone of this piece, which will be possible due to the capability of the strap.
3. When the proper length of the strap is decided, then the extra piece of strap will be cut along the left border of the upper attachment means, ATM2 on the upper surface of this unit. Please note that at this point the strap is attached to hook-fastener attachment means, ATM2, from the upper surface of this piece.
4. Then the user will remove the protective cover, PC, and adhere the lower or base of this piece to the upper surface of the strap through use of the adhesive layer.

This combination will make:
  a. The free end of the strap have a neat cut.
  b. The combination make a zone of hook-fastener, attachment means, ATM2, in the lower surface of the free end of the strap that will be used to attach the free end of the strap to the outer surface of special supports that will accept this end. This will be very useful in units for use in various areas, such the heels and shoulder, etc.

The advantage of this unit is that allows a one-size unit to be used as a universal unit or will allow a better adjustment of the length of the straps.

Figure 18A:
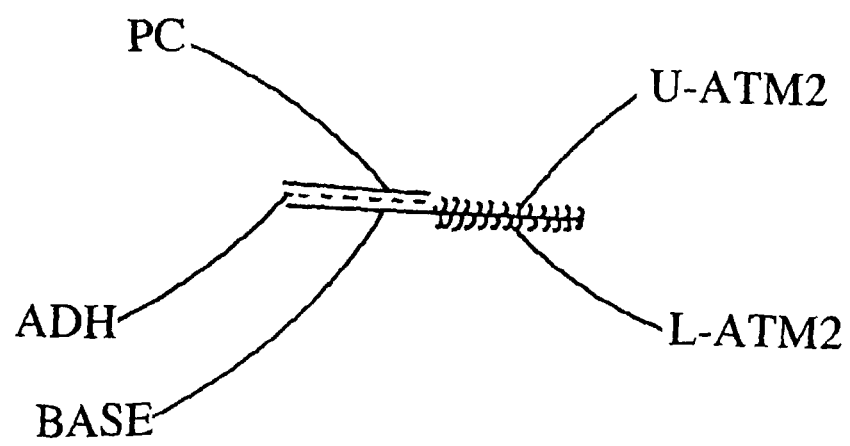
FIG. 18A shows a vertical, horizontal, cross-cut view of the unit shown at FIG. 18, that allows the free end of the strap to be attached to the adhesive ADH.

FIG. 18A shows the cross cut view of the unit shown at FIG. 18. In this picture the unit has base, BASE, made from a layer of fabric, with a zone of hook, fastener, attachment means, ATM2 on its upper and lower surfaces shown in the right side. On the upper surface of the left half of the base, the fabric has a layer of adhesive, ADH, that has a protective cover, PC, on it. At the time of use this piece will be attached to the top surface of a matching support by virtue of the lower attachment means, L-ATM2. The elastic strap will attach to the upper attachment mean, U-ATM2, of end unit and with adjustment, proper length of the strap will be known and then the extra piece will be cut along the left border of the upper attachment means which is on the border of the protective cover. Then the user will remove the protective cover, PC, and adhere the base to the upper surface of the strap. This will make a clean-cut side and the combination will make a zone of attachment means, ATM2, on the lower end of the strap that will be used to attach the end of the strap to the surface of the units for use in the heel and shoulder, etc.

Figure 18B:
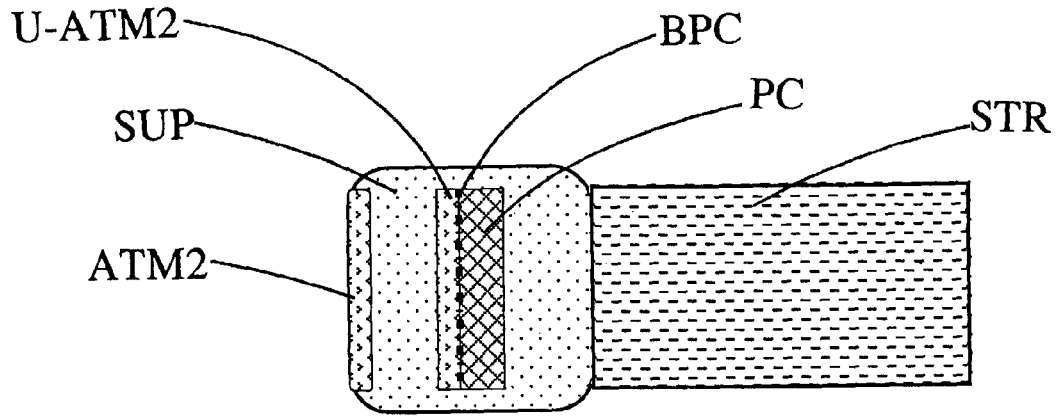
FIG. 18B shows the method of using the end piece unit on a support.

FIG. 18B (also note FIG. 18C) shows the front view of an end unit shown at FIG. 18 that is placed on a support, SUP. This support has a non-stretchable body with an outer surface made from a layer of loop-fastener, attachment means, ATM1, its inner surface being a soft lining that stands on the skin, and a thin layer of foam sandwiched in between. The strap, STR, is attached to the right border of the support. The outer surface of the left border of the support, SUP, has a long, narrow zone of hook-fastener attachment means, ATM2. The end unit piece is attached to the surface of the support, SUP, due to the attachment means, ATM2, in its lower surface, this part is shown better in FIG. 18C.

Figure 18C:
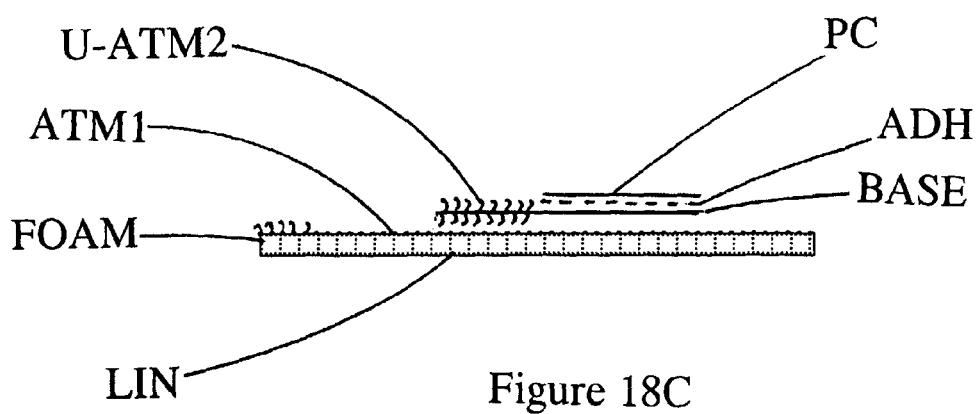
FIG. 18C shows a magnified vertical, cross-cut view of the support from FIG. 18B and its details.

FIG. 18C shows the vertical, cross-cut view of the support, SUP shown at FIG. 18B with an end piece close and parallel to it. The strap is not shown. The upper layer of the support is a loop-fastener attachment means, marked at ATM1, and its lower surface is a soft lining, LIN, the layer of foam, FOAM is in between. The end unit is shown on top of the surface of the support, SUP, and consists of a base, BASE, made from a layer of fabric or a polymer. A zone of hook-fastener attachment means, ATM2 is on its upper surface, U-ATM2, and another zone of hook-fastener attachment means is in the lower surface of this piece but is not marked. The other segment of the base, BASE has a layer of adhesive shown at ADH, that has a protective cover, PC, on it.

The method of use:
1. Initially the end unit will be attached to the body of the outer surface of the support, SUP, due to its loop, fastener attachment means, ATM2.
2. Then the strap will wrap around the limb and be pulled to attach to the zone of ATM2 shown on the left border of the support, SUP. This occurs due to the strap's own capability that functions as a loop-fastener attachment means. This step allows the length of the strap to be decided.
3. After the proper length of the strap is decided, it will be further to attach to the upper attachment means, U-ATM2, of the end piece.
4. The extra strap will be cut along the right border of the upper attachment means, U-ATM2, on the upper surface of this piece. Please note that at this point the strap is attached to the U-ATM2 from the outer surface of this piece.
5. Then the user will remove the protective cover, PC, and adhere the base, BASE to the upper surface of the strap by use of the adhesive layer.

At this point the lower surface of the end piece is attached to the upper surface of the support by virtue of the lower attachment means, ATM2 and importantly, its position may be further changed by moving it back and forth on the support.

Figure 18D:
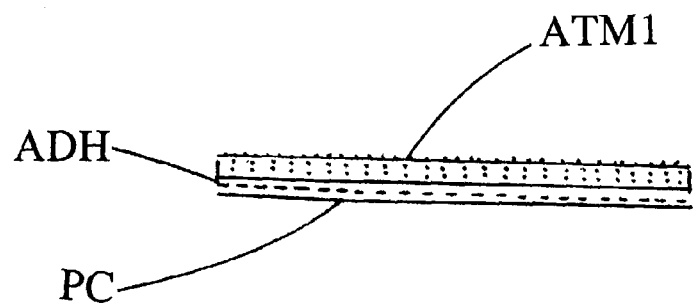
FIG. 18D shows a complementary unit to change the surface of a vinyl support unit for use with an end piece shown at FIG. 18.

FIG. 18D shows the vertical, cross-cut view of a mating piece that allows the unit shown at FIG. 18 to be used with a support that is made from a material, such as vinyl, that does not have the loop-fastener means on its own surface. This piece has an outer surface made from a loop-fastener attachment means, ATM1, and its lower surface has a layer of adhesive shown at ADH covered with a protective cover, PC, on it.

The method of use:
1. Initially the protective cover, PC, of this mating piece will be removed and the unit adhered to the outer surface of the support, SUP.

This will modify the vinyl or similar supports, and allow the end piece shown at FIG. 18 to be attached to the loop-fastener attachment means, ATM1, of this piece to function.

Figure 19:
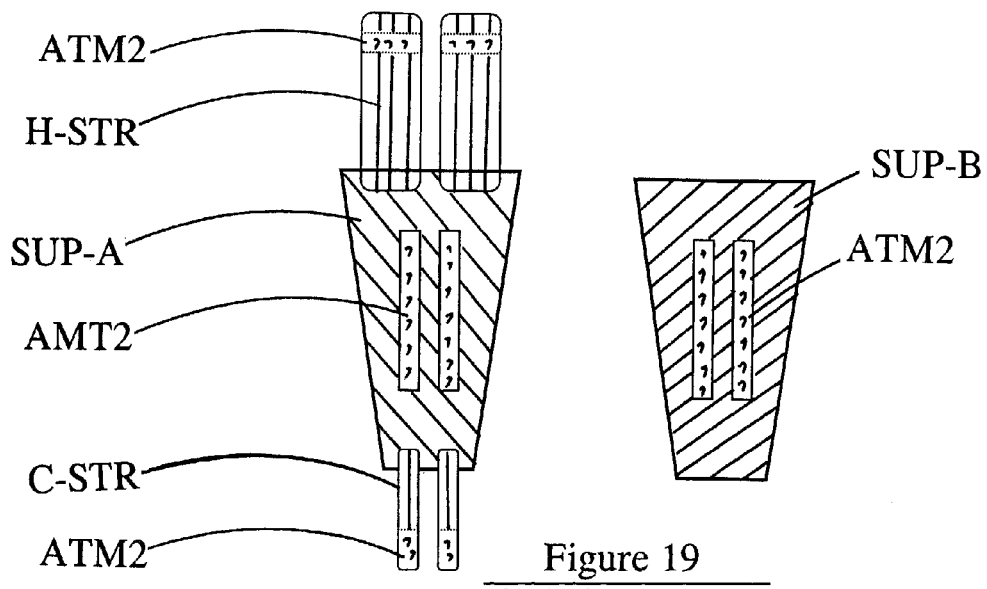
FIG. 19 shows support units for the head, in which each one will cover one side of the face and be held together by straps.

FIG. 19 shows the general view of a support unit designed for use in the head. This unit consists of two similar pieces of support units that will be attached to each other by use of straps. The supports have a trapezoid body as show at SUP, with a wider, upper area for the head area and a narrower, lower area for placement on the chin area. Importantly, this support has a laminated body with an outer layer made of loop-fastener attachment means, ATM, an inner layer which is a soft, fabric, lining to contact skin and a layer of foam in between. In the units shown here, the outer surface of the support, SUP, has two layers of long and narrow zones of hook-fastener attachment means, ATM2, that allow the body of another strap made from lycra with a smaller support on its end almost similar to the one shown at FIGS. 1-4 to be attached to it on a detachable, re-attachable basis. This strap, shown in more detail at FIG. 20, will attach to the unit shown at FIG. 19 on a detachable, re-attachable basis. This is important since the body of this particular strap allows such an attachment, which will keep the unit stable and prevent it from moving.

The upper border of the trapezoid support has two stretchable straps made from lycra, shown at HSTR.

These straps attach the head areas of these two support pieces together on a stretchable, detachable and re-attachable basis. The free ends of these two straps have a hook-fastener attachment means, ATM2, that allow the ends of these straps to be attached to the outer surface of the other support, SUP, on a detachable, re-attachable basis.

The lower border of the support unit that covers the chin area also has two stretchable, but narrower, straps made from lycra, shown at C-STR, that attach the chin areas of these two supports together on a stretchable, detachable and re-attachable basis. The free ends of these two chin straps, C-STR have small zones of hook-fastener attachment means, ATM2 that allow the ends of these straps to be attached to the outer surface of the second support, SUP, on a detachable re-attachable basis.

The second support piece has similar body, except it does not have the H-STR and C-STR straps, since the these straps will be attached to it on a detachable, re-attachable basis.

Figure 20:
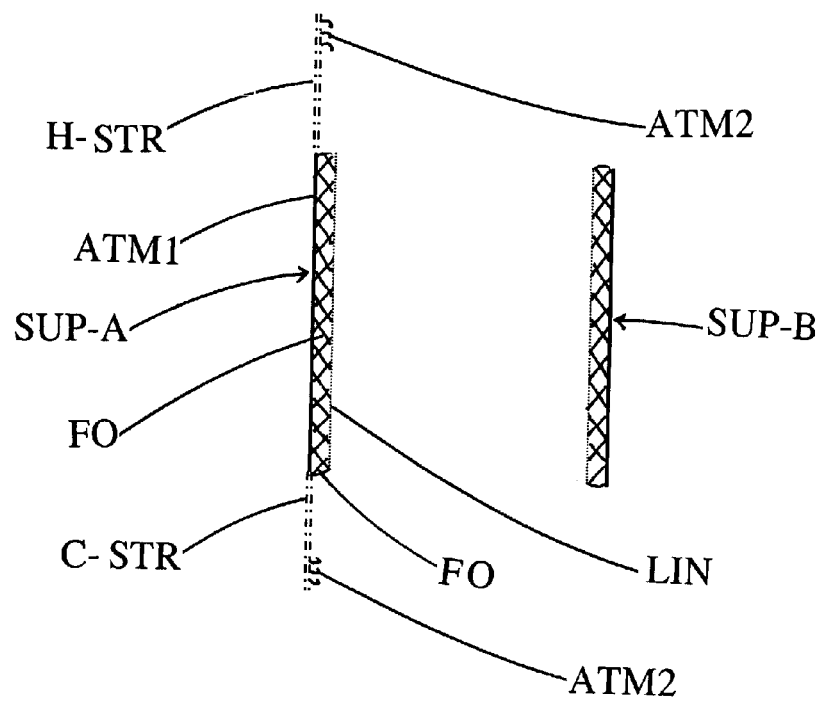
FIG. 20 shows the side view of the unit shown at FIG. 19.

FIG. 20 shows schematically the side view of the unit for the head shown at FIG. 19. In this figure the body of the support, SUP, is shown from a laminated piece with an outer surface made from a layer of loop, fastener attachment means, ATM1, and an inner layer made from a layer of soft fabric lining, LIN, that contacts the skin. A layer of foam, FO, is sandwiched between these two layers. The elastic strap for the head is shown at H-STR and the elastic strap for the chin is shown at C-STR both of these have zones of attachment means, ATM2.

Figure 21:
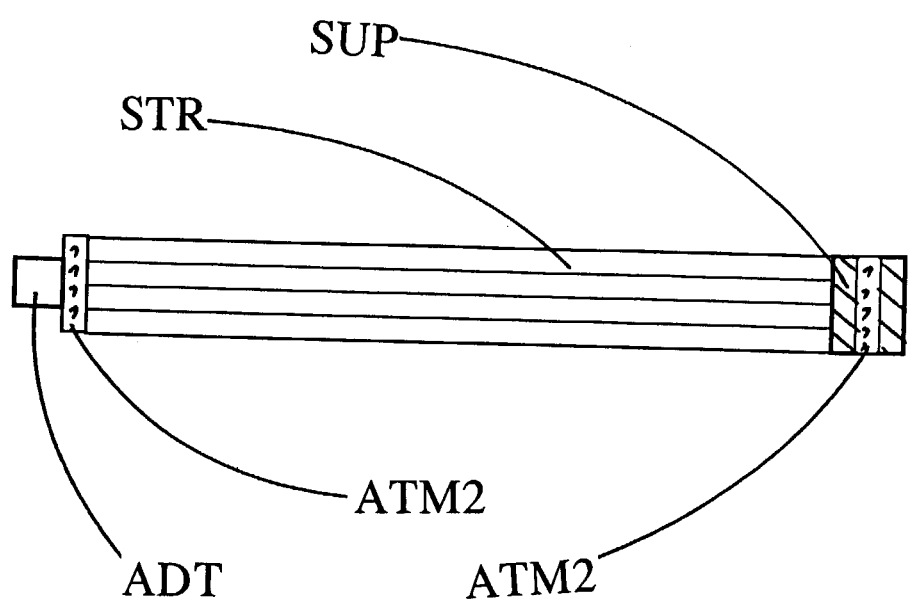
FIG. 21 shows a strap unit for use with the unit shown at FIG. 20. This strap goes around the head horizontally.

FIG. 21 shows schematically the general view of a complementary strap for use with the unit shown at FIG. 19. This strap is similar to the strap shown at FIGS. 1-4. Basically, this shows a long, stretchable strap, STR, that is attached to a support, SUP. The support has a zone of hook-fastener, attachment means, ATM2, on its front surface that allows the body of strap, STR, to attach to it on a detachable, re-attachable basis. The rear surface of this support, STR, may also have another zone of hook-fastener attachment means, ATM2, (which cannot be seen in this view) that allows the support, SUP, from this strap to attach to the outer surface of the support, SUP, for the head and chin on a detachable, re-attachable basis. Please note that the support for the head and chin, has a laminated body with an outer layer made from a layer of loop-fastener attachment means.

The free end of the strap, STR shown on the left side of this figure has an adhesive piece similar to one shown at FIGS. 1-4 that allows the end of this strap to be attached to the outer surface of the strap, STR. This can also have a zone of hook-fastener attachment means, ATM2.

This combination of strap and head and chin support makes a valuable unit, since it allows a very stable and versatile unit for use for the wounds of the head and face.

This unit allows the head straps, H-STR, for the head site to be opened for adjusting the size or the tension of unit or for the examination of the wound site. Also the chin straps, C-STR allow the size and the tension of the unit to be adjusted as well. The strap, STR, goes horizontally around the head and allows the size of the strap and thus, the horizontal tension, to be adjusted. Also, it allows the wounds in the occipital or the frontal part of the head to be checked.

Figure 22:
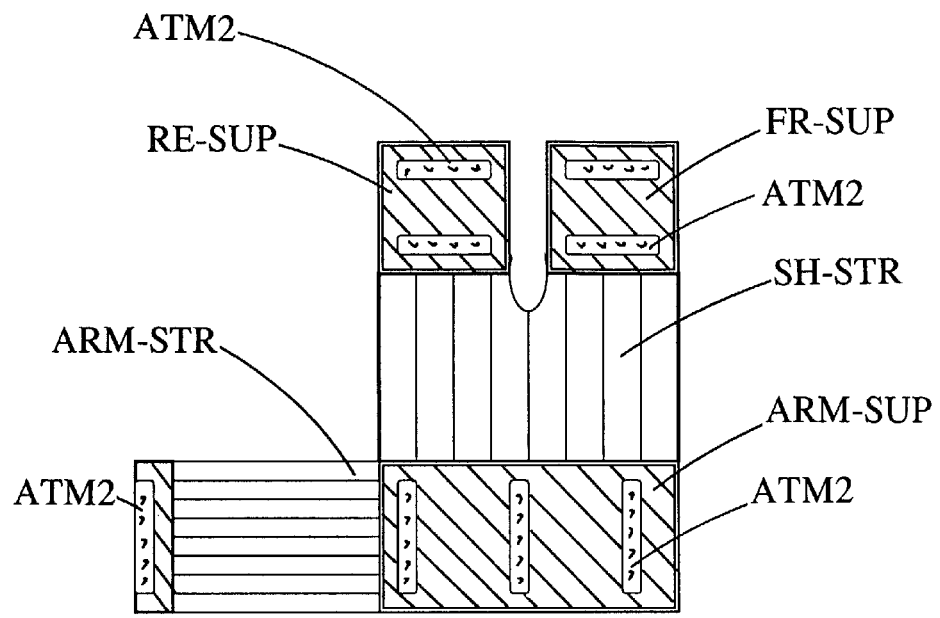
FIG. 22 shows a support for shoulder.

FIG. 22 shows schematically the general view of a support unit for the shoulder. This unit has a non-stretchable support unit shown as ARM-SUP, that covers the outer side of the arm. This support has laminated body with an outer layer made from a loop-fastener attachment means, ATM1, and an inner layer which is a soft fabric lining to contact skin and a layer of foam/sponge in between. In the units shown here, the outer surface of the support, SUP, will have at least two long and narrow zones of hook-fastener attachment means, ATM2. This allows the body of an arm strap, ARM-STR, made from LYCRA (TM), with a smaller support on its free end, almost similar to the one shown at FIGS. 1-4 to be attached to the ARM-SUP, the strap, ARM-STR, is designed to wrap around the upper arm and attach to the surface of the ARM-SUP on a detachable, re-attachable basis.

Another wider, elastic shoulder strap, SH-STR, is also made from LYCRA (TM) and is attached to the upper border of the ARM-SUP. The shoulder strap, SH-STR is designed to cover the shoulder and keep the dressing securely on it. Importantly, the stretchable body of this strap allows the shoulder to move easily. The shoulder strap, SH-STR, has two support pieces of its own that cover the front and rear (FR-SUP and RE-SUP) upper part of the chest. These two supports are made from the same material as the arm support, ARM-SUP, and also have zones of hook-fastener attachment means, ATM2, on their front surfaces.

At the time of use, the FR-SUP is placed on the front of the upper chest and the RE-SUP placed on the rear surface of the chest on the user's back. A strap shown at FIG. 23 goes in front of the chest and wraps in the armpit of the opposite arm, with one free end of the strap attaching to the outer surface of the FR-SUP and the other to the outer surface of the RE-SUP on a detachable, re-attachable basis.

Figure 23:
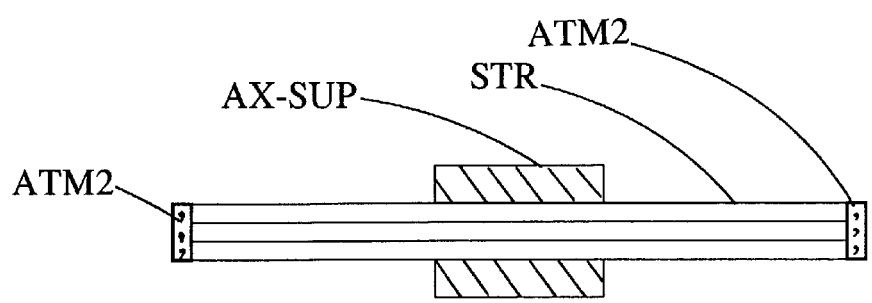
FIG. 23 shows a strap for use with the unit shown at FIG. 22.

A piece of support, shown as axillary sup, AX-SUP, in FIG. 23 and made from same laminated material will go under the armpit and function as a stabilizer, preventing the strap from curling.

Method of use:
1. The body of arm strap, ARM-STR, will wrap around the arm and first attach to the attachment zone, ATM2, from the arm-support, ARM-SUP, due to the special property of the strap that functions as the loop-attachment means. Then the hook-fastener attachment means, ATM2, of the free end of the arm strap, ARM-STR, will attach to the outer surface of the arm support, ARM SUP, on a detachable re-attachable basis. This will hold the arm support, ARM-SUP on the outer surface of the arm in a stable, comfortable fashion.
2. The shoulder straps will be next be wrapped on the shoulder area; its front support, FR-SUP, being placed on the front of the upper chest and its rear support, RE-SUP, placed on the rear surface of the chest behind the user.
3. One free end of strap STR shown at FIG. 23 will be placed on the front of the chest and be pulled to a comfortable tension, wrapped in the armpit of the opposite arm.
4. In the armpit area the strap, STR, will be attached to the outer surface of the axillary sup, AX-SUP shown in FIG. 23 on a detachable, re-attachable basis. Please note that the axillary sup, AX-SUP, is made from a laminated material and has a zone of hook-fastener attachment means on its own outer surface that allows the attachment of the strap, STR, to its body occur. This axillary sup, AXSUP functions as a stabilizer and prevents the strap from curling.
5. Then the free end of the strap, STR, will be pulled in the back of the chest, and be attached to the outer surface of the RE-SUP on a detachable, re-attachable basis.

This method and means makes a stable, comfortable unit for the shoulder joint. Importantly, one end of the strap for the chest will be attached first, and a buckle system as shown at FIGS. 16-18 (or similar units) may be used to adjust the length of this strap. FIG. 23 shows schematically the general view of the strap for the shoulder support unit shown at FIG. 22. In this figure the body of the axillary support, AX-SUP, is shown. The front/outer surface of this support has a zone of hook-fastener attachment means, ATM2, which is under the strap, STR, and cannot be seen in this view. Both free ends of the strap, STR, have zones of hook-fastener attachment means, ATM2. As mentioned above, one free end of this strap will be attached to the front of the front support, FR-SUP. The strap will then be wrapped around the chest, and go under the opposite armpit to have its other free end attach to the outer surface of the RE-SUP on a detachable, re-attachable basis. The body of the axillary support, AX-SUP, covers the axillary area and will keep the strap, STR, in proper position, simultaneously preventing it from curling.

Figure 24:
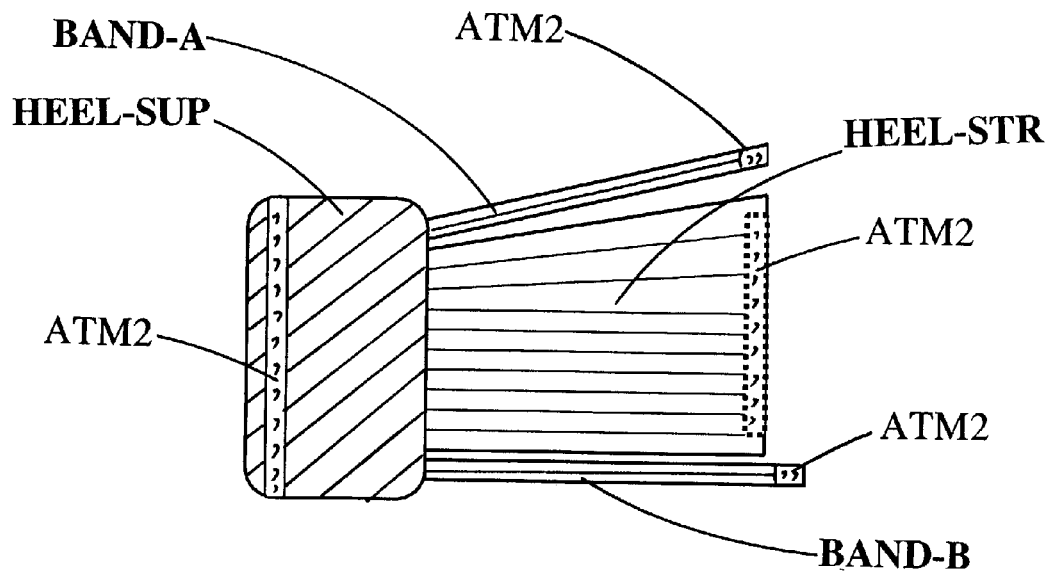
FIG. 24 is a unit for the ankle.

FIG. 24 shows schematically the general view of a support unit for the ankle. This unit also consists of a non-stretchable support unit shown at HEEL-SUP that stands on the front of the ankle joint. This support piece consists of a laminated body with an outer surface made from a layer of loop-fastener attachment means, ATM1, an inner, soft lining for contact skin, and a thin layer of foam in between. The outer surface of the heel support, HEEL-SUP has a long narrow zone of hook-fastener attachment means, ATM2. A wide elastic strap, made from LYCRA, (TM) shown at HEEL-STR is attached to the right border of the HEEL-SUP. The free end of this strap has a zone of hook-fastener attachment means, ATM2. This strap is designed to wrap around the heel and attach to the surface of the heel support, HEEL-SUP, on a detachable, re-attachable basis. The unit has two bands, BAND-A and BAND-B, which are made from Lycra and are similar to the bands shown at FIG. 3. These bands will go around the ankle on each side and attach to the ends of the zone of the hook-fastener attachment means, ATM2, from the support, HEEL-SUP, on a detachable, re-attachable basis. Or, they may have smaller zones of attachment means for their own as shown at ATM2 that allows these zones to be attached to the surface of the heel support, HEEL-SUP on a detachable, re-attachable basis. The strap, STR, and bands, BAND-A and BAND-B, are made from special material (LYCRA-TM) that allows these pieces to attach to the hook-fastener attachment means, ATM2, on a detachable, re-attachable basis.

1. The HEEL-SUP will be placed on the front of the ankle joint.
2. The band, BAND-A, will be pulled to go around the ankle and come forward to attach to the zone of the hook-fastener attachment means, ATM2, from the heel-support, HEEL-SUP, on a detachable, re-attachable basis.
3. The band, BAND-B, will be pulled to go around the ankle and come forward to attach to the zone of the hook-fastener attachment means, ATM2, from the heel-support, HEEL-SUP, on a detachable, re-attachable basis.
4. The heel strap, HEEL-STR, will be pulled to a comfortable tension and then wrapped around the heel and to attach to the zone of hook-fastener attachment means, ATM2, from the heel support, HEEL-SUP. Such an attachment is possible due to the special property of the strap that functions as the stretchable, loop-fastener attachment means.

5. Then the hook-fastener attachment means, ATM2, of the free end of the strap will be attached to the outer surface of the heel support, HEEL-SUP on a detachable, re-attachable basis.

This method makes a comfortable, sturdy unit for the heel joint. The elastic strap wraps well around the heel and allows it to move freely.

Please note that the method of use of the bands, BAND-A and BAND-B, are shown previously at FIGS. 3-4.

Importantly, it is possible to use this unit without the use of the bands, therefore, some models may not have BAND-A and BAND-B, or may have only one of these bands.

In these models the steps 2 and 3 from the method of use will be omitted

Figure 25:
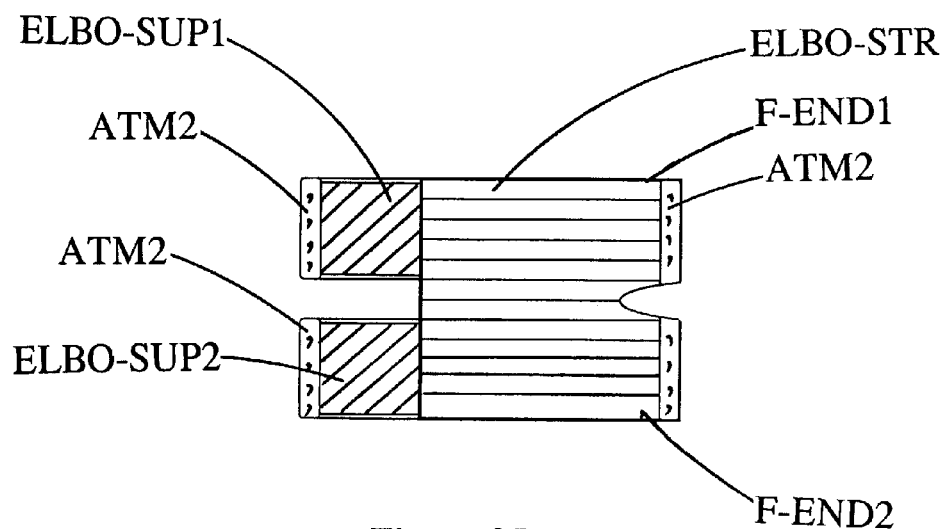
FIG. 25 shows a unit for the elbow.

FIG. 25 schematically shows the general view of a support unit for the elbow. This unit consists of two pieces of a non-stretchable, support shown at ELBO-SUP1 and ELBO-SUP2 that will stand on the front of the elbow, above and under the elbow crease. These supports are made from a laminated body with an outer surface made of a layer of loop-fastener attachment means, ATM1, an inner soft lining for contact skin and a thin layer of foam in between. The outer surface of the supports has a zone of hook-fastener attachment means shown at ATM2. A wide, elastic strap, made from LYCRA, (TM) shown at ELBO-STR, is attached to the right border of the ELBO-SUP. The strap, ELBO-STR, has two free ends, F-END1 and F-END2. The very end of these free ends has a zone of hook-fastener attachment means, ATM2. This strap is designed to wrap around the elbow and have its free ends, FEND1 and F-END2, attach to the outer surface of the elbow support, ELBO-SUP1 and ELBO-SUP2, on a detachable, re-attachable basis.

Importantly, the body of the strap, STR, will first attach to the attachment zone, ATM2, from the outer surface of the support units. This attachment is possible due to the special property of the strap that functions as the stretchable, loop-fastener attachment means. Then the attachment means, ATM2, of the free ends of the strap, F-END1 and F-END2 will attach to the outer surface of the supports, ELBO-SUP1 and ELBO-SUP2 on a detachable, re-attachable basis. This method makes a comfortable, sturdy unit for the elbow joint area. Importantly, this leaves the front of the elbow open to bend freely.

Method of use.
1. The ELBO-SUP1 will be placed on the front of lower arm above the elbow crease.
2. The upper part of the ELBO-STR, will be wrapped around the elbow joint in the lower arm area above the elbow crease and its upper end piece, F-END1, will be attached to the outer surface of the support, ELBO-SUP1 on a detachable, re-attachable basis.
3. The lower part of the ELBO-STR, along its main body, will be wrapped around the elbow joint in the elbow joint, upper forearm area under the elbow crease and its end piece, F-END2, will be attached to the outer surface of the support, ELBO-SUP2 on a detachable, re-attachable basis.
4. The tension of the strap may be changed by further adjustment of the free ends of the strap, F-END1 and F-END2 to make an effective, yet comfortable, unit. Importantly, the body of the strap, STR, will first attach to the attachment zone, ATM2 from the support unit. Such an attachment is possible due to the special property of the body of strap that functions as the stretchable, loop-fastener attachment means. Then the attachment means, ATM2, of the free ends, F-END1 and F-END2 will attach to the surface of the supports ELBO-SUP1 and ELBO-SUP2, on a detachable, re-attachable basis. This method makes a comfortable, sturdy unit for covering the elbow-joint area. Importantly, this leaves the front of the elbow open to bend freely.

Figure 26:
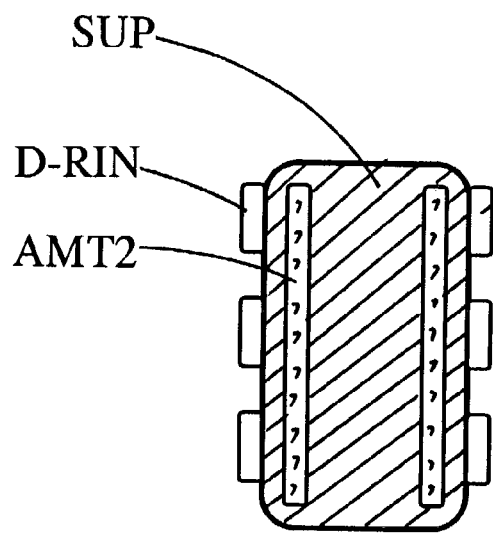
FIG. 26 shows a support unit for hip that also uses D-Rings. The straps are not shown in this Figure.

FIG. 26 schematically shows the general view of a support unit for the hip. This unit consists of one non-stretchable, support unit shown at SUP, that is placed on the hip/joint area. This support has zones of hook-fastener attachment means, ATM2, on its front/outer surface, that allow a strap with a loop-fastener attachment means, ATM1, to be attached to it on detachable, re-attachable basis. Alternatively, this support may have a series of D-Rings shown at D.RIN, on its sides in order to allow the free end of the straps to go through, make a U-turn, and attach to their own outer surface on a detachable, re-attachable basis. This method allows the length of the straps to be adjusted. In the models made, the applicant has used three straps with these units. This unit may have another support unit to be placed on the other hip joint in order to hold the straps in a stable position. A pad will be placed under the support for a better result.

Figure 26B:
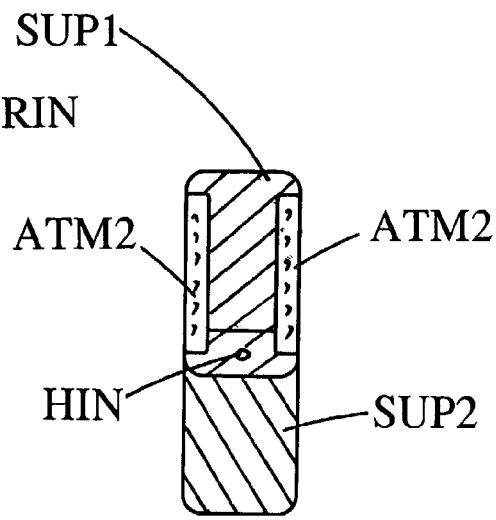
FIG. 26B shows a hinged-support unit for the hip that allows the support to angulate.

FIG. 26B schematically shows a support unit for the hip that consists of hinging two support pieces so that it allows the person to bend the hip joint. In this view the first support, made from a non-stretchable piece, is shown at SUP1, and hinges to the second support, SUP2, at hinge HIN. The outer surfaces of the support pieces have zones of hook-fastener attachment means, ATM2. These zones are not shown for the support 2, SUP2 to prevent a crowded Figure. This allows a series of the straps made from loop-fastener attachment means, ATM1, to be attached to the supports on a detachable, re-attachable basis. This support also may have a series of D-Rings on the sides. The supports shown at these two figures will hold a cushion pad made from a foam covered with fabric that will be attached to the support unit on a detachable, re-attachable basis. This allows the cushion to compress the wound area.

Figure 26C:
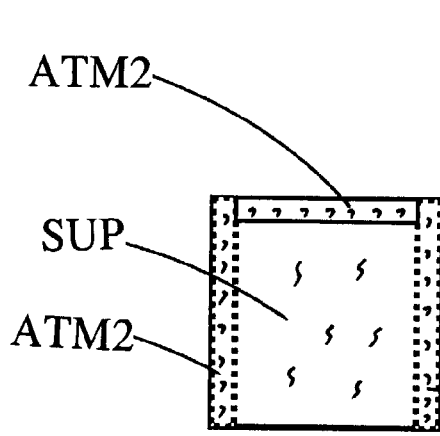
FIG. 26C shows a support unit for the chest that prevents clothing from touching the wound site.

FIG. 26C schematically shows a protective support unit for the chest. This is designed to keep clothing away from the wound site of various forms, particularly after open-heart surgeries. This unit prevents clothing from touching the chest wound, and has a rather rigid and clear support piece that will be held away from the chest wall by use of walls made of foam pads. The outer surface of the support, SUP, has zones of hook-fastener attachment means, ATM2, on its upper and side borders. That allows the straps made from loop-fastener attachment means, ATM1, to be attached to it on a detachable, re-attachable basis. These straps of this unit consists of following:

1. A vertical strap that hangs on each side of the neck, both end pieces attaching to the zone of the hook-fastener attachment means, ATM2, which is located on the upper border of the support.
2. One or two horizontal straps wrap around the chest. Their end pieces will attach to the zone of the hook-fastener attachment means, ATM2, which is located on the borders of the support on its sides. Commonly, one strap around the neck and two from the chest area are used with this unit.

Figure 26D:
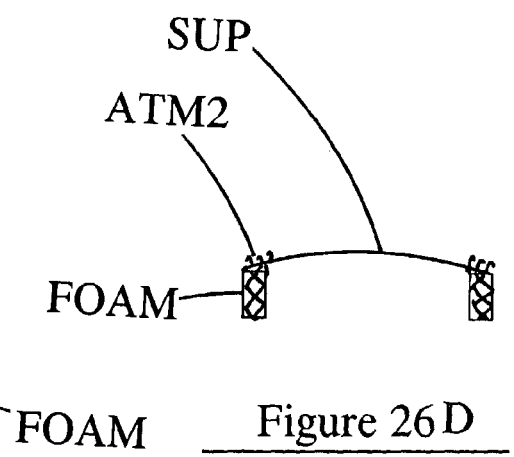
FIG. 26D shows the vertical, cross-cut view of the unit shown at FIG. 26D. It shows the foam that covers the sides of the wound and prevents the body of the support from touching the skin.

FIG. 26D shows schematically the vertical, cross-cut view of the unit shown at FIG. 26C. In this figure the body of the support, SUP, is shown and has a curve that keeps it away from the wound site. The upper/outer surface of the support has hook-fastener attachment means, ATM2, on its right and left borders. The lower surface of the support has two foam pads, FOAM, that will keep the chest support, SUP, away from the chest wall.

Figures 27, 28:
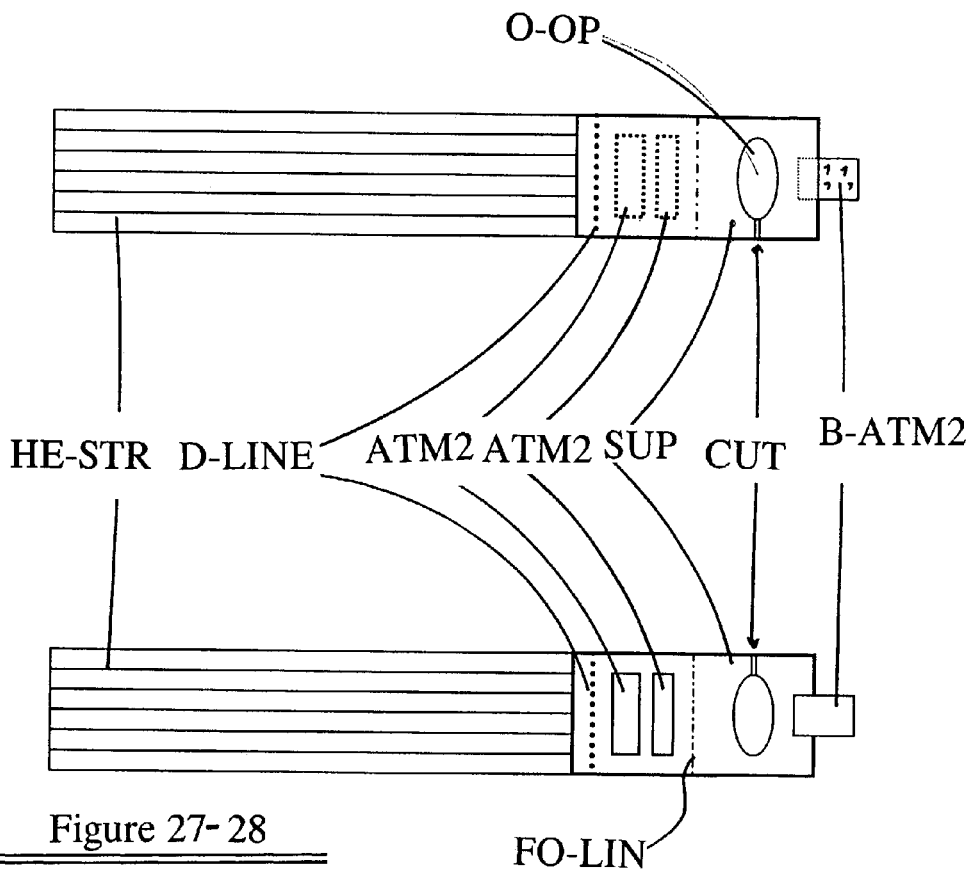
FIGS. 27-28 show the front and the rear view of a unit for the ear.

FIGS. 27-28 schematically shows the front and rear view of a support unit for the ear. The front view is shown at FIG. 27 and is rotated 180 degrees to show its rear image that looks somewhat similar to its mirror image at FIG. 28. This unit has a support, SUP, made from a laminated body, with an outer surface made of a layer of loop-fastener attachment means, ATM1, and an inner, soft lining for contacting skin with a thin layer of foam in between. In the process of use this support will fold along a line, FO-LIN. The body of the support, SUP, on the right side has an oval opening, O-OP, with a cut, CUT, on its lower pole. This opening allows the support to be placed around the base of the ear and prevent it from moving. The rear/outer surface of the support, SUP, on the left side has two zones of hook-fastener attachment means, shown at ATM2. A wide, elastic strap, made from LYCRA, (TM) and shown at HE-STR, is designed to wrap around the head. This strap is attached to the body of the support, SUP, along the dotted-line, D-LINE. Importantly, the attachment line, D-LINE, is intentionally away from the edge of the support. This allows the band of attachment means, B-ATM2, to attach to the rear surface of the support, SUP, near the D-LINE, so that the strap will finally wrap over this band.

At the time of use:

A. The oval opening, O-OP of the body of the support, SUP, will be placed around the base of the ear via the cut, CUT. This method will prevent the movement of the support after placement.
B. The rear half of the support, SUP, shown at the left side will fold along the folding line, FO-LIN, and cover the ear. The free borders of these two pieces will be held together by attaching the band of the attachment means, B-ATM2, to the rear surface of the support, SUP, adjacent to the D-LINE. The folded support holds the dressing of the ear on it securely.
C. Then the head strap, HE-STR, which is made from Lycra, will wrap around the head horizontally, on the front of the head, the temporal side and the occipital area respectively. So that ultimately, its free end will attach to the outer surface of the folded support, SUP, by use of the two zones of the attachment means, ATM2.

This method makes a secure and simple means of holding the dressing on the ear, which is commonly difficult.

The body of the support may be made to have more foam and be thicker, or also to have a more protective, non-compressible body to avoid compression of the ear. The strap may also have a piece to go vertically and use the method shown for the head support.

Importantly, a small envelope made from fabric may be used to go over the wound of the ear and be held in place by this unit.

Figure 29:
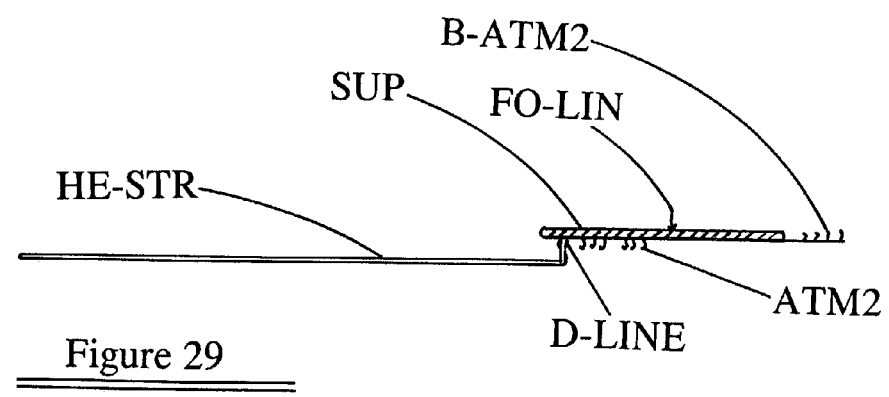
FIG. 29 shows the side view of the unit for the ear.

FIG. 29 schematically shows the side view of the unit shown at the previous two figures. This figure shows the support, SUP, the zones of the hook-fastener attachment means, ATM2, on its lower surface, (only one zone is marked), the folding line, FO-LIN and the head strap, HE-STR. Note the point of the attachment of the head strap, HE-STR to the body of the support, SUP, which is marked at D-LINE is intentionally away from the very edge of the support. This is to allow the band of attachment means, B-ATM2 to attach to the rear surface of the support, SUP, near the D-LINE. This special design allows the head strap, HE-STR, to wrap over this band.

FIG. 30 schematically shows the general view of a support unit for the Pacemaker-Defibrillator Wound. This unit consists of a non-stretchable support unit, SUP, that stands on the front of the upper chest in the subclavian area and holds a pad, PAD, on the wound site. The pad, PAD, is attached to the inner surface of the support, SUP, on the upper half area of the support, by a hook-fastener attachment means, ATM2. The body of this support is also made from a laminated body with an outer surface made from a layer of loop-fastener attachment means, ATM1, and an inner soft lining for contact skin, with a thin layer of foam in between. The body of the support on its upper half consists of a thicker part made from a segment of support that has made a U-turn and is attached to its own surface, shown best at U-SUP at FIG. 31. This method makes the upper half of this support have a body made of a layer of loop-fastener attachment means, ATM1, on both sides. The support and attached pad will be held in the upper shoulder area by use of two straps made from a laminated layers of loop-fastener attachment means, ATM1, both its outer and its inner surfaces with a thin layer of foam in between. The straps consist as follows:

a. A horizontal strap shown at H-STR that is designed to wrap around the chest and attach to the outer surface of the support, SUP, by use of a zone of hook-fastener attachment means, ATM2. This is located on both ends of the strap or by use of an extra piece of a double-sided ATM2.
b. A vertical shoulder strap, S-STR, that covers the shoulder. The rear end of this strap makes a U-turn around the horizontal strap, H-STR, shown at U1, to attach to the surface of its own body. This will in turn keep the horizontal strap H-STR and the shoulder strap, S-STR, attached to each other on an adjustable basis, and is shown best at FIG. 31A.
c. The front portion of the shoulder strap, S-STR, stands in front of the support, SUP, and may attach to it by use of pieces of double-sided hook-fastener attachment means, ATM2. It will then move down, the free end of it will making a U-turn around the patient's wrist and attaching to the rear surface of its own body as shown at U2 FIG. 31A.

This Unit:

1. Provides a mild compression to the wound site and prevents hematoma.
2. Will hold the wrist in position and prevents it from moving.
3. Will prevent other objects from reaching the wound site and causing pain.

Importantly, the size, shape and the make up of the pads may vary. Also the nature of the straps may vary; the straps may be made to be:

1. Non-stretchable
2. Stretchable, elastic material
3. Combination of non-stretchable and stretchable materials. The elastic materials may have their own attachment property or they may have pieces of attachment means attached to their body.

Importantly, in these units the body of the support is primarily made from a material that has an outer surface made from a layer of loop-fastener attachment means ATM1 and its inner surface is a soft lining that would stand on the skin, with a thin layer of foam in between. This allows the shoulder and horizontal straps to be attached to the surface of the support in any area that they touch when a double sided hook-fastener attachment means, ATM2, is used. This method makes these units more versatile.

FIG. 31 schematically shows the side view of the support unit shown in FIG. 30. In this figure the support, SUP is shown and the body of the support makes a U-turn and attaches to its own surface on its upper half as shown at U-SUP. The pad, PAD is attached to the front surface of the U-SUP. The rear surface of the pad is specified at S-PAD and may have a layer of loop-fastener attachment means, ATM1. The pad, PAD, is attached to the inner surface of the support, U-SUP, through use of attachment means, ATM2.

FIG. 31A schematically shows the side view of the arrangement of the straps. In this view the shoulder strap, S-STR, stands on the shoulder (not shown). The rear segment of the strap makes a U-turn, U1, around the horizontal strap, H-STR, and attaches to its own body by use of ATM2, on a detachable, re-attachable basis. This keeps the horizontal strap, H-STR, and the shoulder strap, S-STR, attached to each other on an adjustable basis.

The front segment of the shoulder strap, S-STR, stands in front of the support (not shown) and may attach to it by use of pieces of double-sided ATM2 patches. It moves down in front of the chest, the free end of the strap making a U-turn, U2, around the wrist, WR, of the patient and attaches to the front surface of its own body by the zone of the ATM2 at its end.

Figure 32:
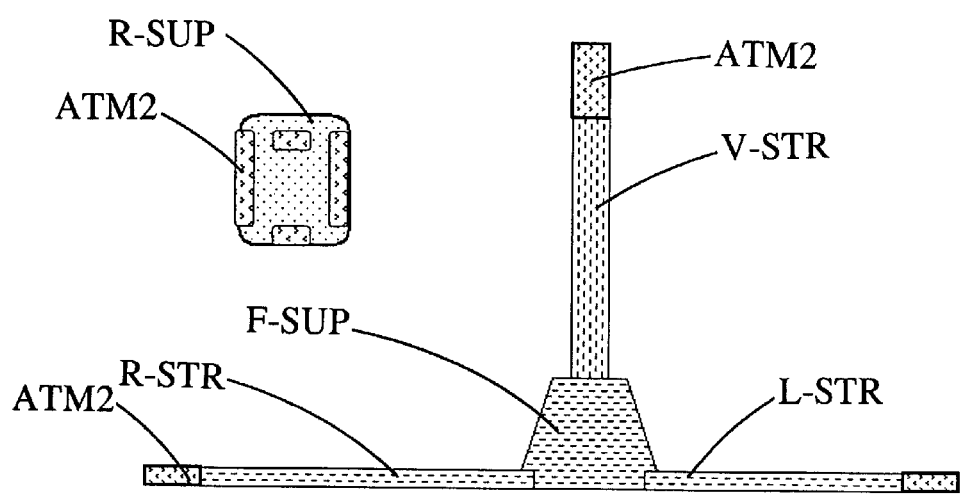
FIG. 32 shows a modified model of the unit shown in previous FIG. 30.

FIG. 32 shows a support unit similar to the unit shown in FIG. 30, except this unit has two complementary support pieces. The first support stands in the front of the chest and is referred to as the Front Support, F-SUP, and the second support stands on the back of the chest and is referred to as the Rear Support, R-SUP. The Front Support, F-SUP, stands on the wound site and will be kept in place through use of a strap in the right side, R-STR, another strap on the left side, L-STR and a vertical strap, V-STR that will come together and attach to the surface of the Rear Support, R-SUP. The free ends of these straps have pieces of hook-fastener attachment means shown at ATM2 that attach to the surface of the R-SUP, made from the laminated body with an outer surface made of a layer of loop-fastener attachment means, ATM1, with an inner soft lining and layer of foam in between. The outer surface (the side that does not come in contact with the body site) of the support also has zones of hook-fastener attachment means, ATM2. This allows the body of the strap to attach to these attachment means on a detachable, re-attachable basis. Thus, the rear support, R-SUP, will in fact act as a catalyzer, allowing the ends of the straps to attach to each other easily. Alternatively, the free ends of the attachment means may be attached to each other through use of double-sided loop or hook fasteners, ATM1 and ATM2. The dressings or pads may be placed under the front or rear support.

Importantly, this model makes the process of the dressing easier in some cases by preventing a crowded area in front.

Importantly, the front support may have a body made of stretchable or non-stretchable layers.

The advantage of this unit is that it allows:
1. The placement of this unit with ease and by one hand only.
2. The compression of each segment of the arm or forearms to be modified.
3. The function of the arm and elbow to be easy due to presence of the cut in the support.
4. The arm and elbow to be hung from a stand in order to facilitate the drainage of the tissue.

Figure 33:
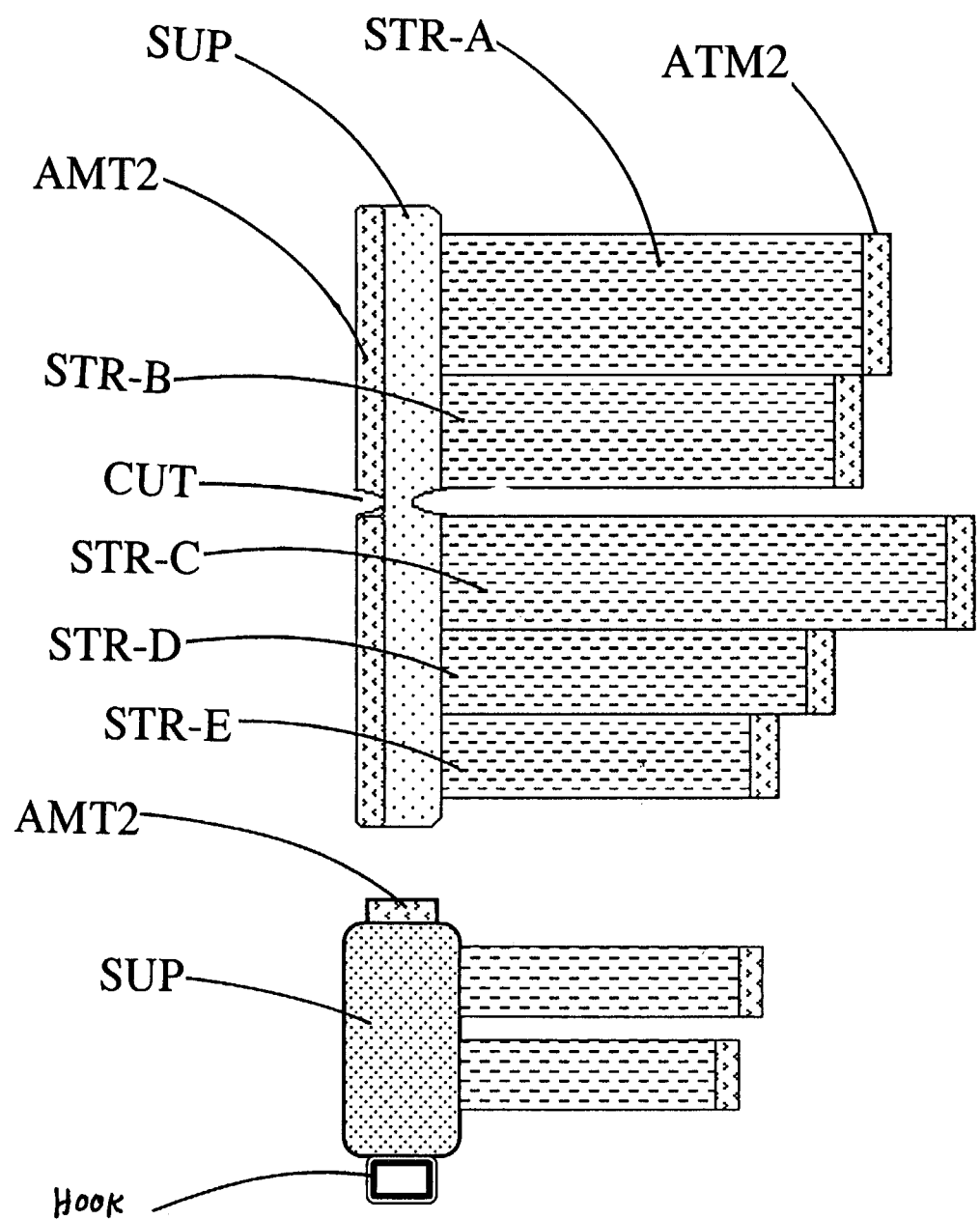
FIG. 33 shows a support unit for use in the arm and forearms.

FIG. 33 shows the general view of a support unit similar to the unit shown at FIG. 6, except this unit is modified for use in the arm and forearms to allow the wound dressing and/or compression of these areas. This unit allows a secure and easy dressing without the need for adhesive tapes. In this model the support, SUP, has a long, rather rectangular shape with cuts in its sides for composure on the elbow crease. The support of this unit stands on the front of the arm and forearm, or on its rear. The support, SUP, has a long zone of hook-fastener attachment means, ATM2, on its left border that allows pieces made of loop-fastener attachment means, ATM1, or a strap made from lycra to be attached to it on a detachable, re-attachable basis. The right border of the support unit, SUP, is attached to a series of straps: STR-A, STR-B that will wrap around the arm area and STR-C, STR-D and STR-E, which are designed to wrap around the forearm. These straps are attached to the border of the support, SUP, on a permanent basis, although importantly, they may be attached to the support on a detachable, re-attachable basis as shown for the leg support. These straps are properly sized to be wrapped around the arm from the axillary area to the elbow-joint area. Importantly, this unit may have three straps for the arm part as well or more.

The straps for the forearm will be placed in the upper, mid- and lower forearm.

These straps may be attached to the support, SUP, by use of pieces of loop-fastener attachment means, ATM2, at their ends. Similar to the leg straps, this method allows the unit to be used for dressing, supporting and compressing the arm and forearms in a very practical, adjustable manner. In this model the straps are also made from one or two layers of LYCRA (TM) and the support means, SUP, is made from a non-stretchable, clear vinyl, or from a laminated body with an outer surface made from a layer of loop-fastener attachment means, ATM1, and an inner layer made from a soft lining that stands on the skin with a thin layer of foam in between. It may also be made from any other materials such as fabric or any other man-made materials. The support may have openings to allow sweat and air to move and also allows a gauze pad or a long, removeable layer of lining shown at LIN, in FIG. 6A or a pad to be placed under it to prevent irritation, place pressure, and allow the application of medication, etc. This unit may allow electrical leads to be held in place as well in order to allow a programmed stimulation of the arm muscles and tissues for various reasons such as the prevention of muscle weakness or prevention of phlebitis.

Importantly, the cuts, CUT, on each side of the support function as hinges and allow the lower segment of the support to rotate in different directions (compared to the upper part) without being disconnected from the upper segment. The advantage of this unit is that it allows the pressure in every special part of the arm and forearms to be adjusted and can be removed and applied easily. When a lining is used, it may be attached to the support, SUP, of the unit on a detachable, re-attachable basis. This allows the lining to be washed or exchanged.

Figure 34:
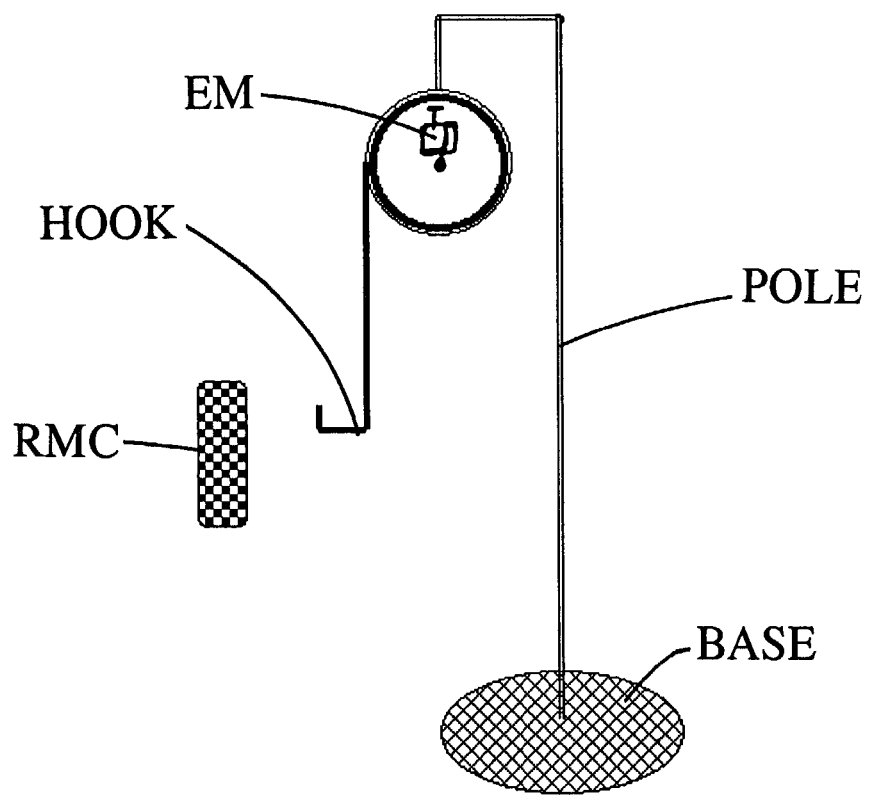
FIG. 34 shows a stand unit with a remote-controlled electrical motor to allow an extremity to be elevated.

The lower part of this figure shows a piece that allows this unit to be extended to the hand area and be attached to an automatic height elevator shown at FIG. 34. This part shows a support for hand, SUP, that stands on the rear of the hand, and will be attached to the lower extension of the support of the arm-elbow by the hook-fastener attachment means, ATM2, in the upper end of the hand support. The straps of this support will wrap around the palm and fingers and will attach to the rear surface of the body of the hand support. The hook in its lower end allows this support to be attached to the hook, HOOK, of the remote-controlled elevator from FIG. 34.

Please note that the straps shown in the upper part of the picture are not attached to each other and are separate.

Importantly, the straps of these units may be attached to the support unit independently by having both their ends attached to each side of the support on a detachable, re-attachable basis.

Importantly also, the straps may be made from a continuous layer of LYCRA, (TM), to allow a uniform coverage of the area. Although, their end pieces will be separate to allow easy placement. An example of this model is shown for the leg at FIG. 6C and is not repeated here to avoid a lengthy application.

FIG. 34 shows schematically an elevator unit that consists of a stand with a remote-controlled electrical motor, EM. This electrical motor moves an attached hook, HOOK, up and down by use of a remote controller, RMC. This unit allows the support, SUP, of the hand and forearm shown at FIG. 33, to be attached to the hook, HOOK, of this elevator to allow the user to elevate or lower the hand or a feet on a remote-controllable fashion. The elevation of a limb will reduce the stasis and allow swelling to decrease in cases such as post-op breast cancer surgery, or vascular problems of the arm and legs. The pole of this unit can be adjusted to allow the overall height of the unit to be controlled. At the time of use the patient adjusts the pole of the stand to match his/her bed or place of sitting, and places his/her support on his/her arm or leg, and then attaches them to the hook of the elevator. Then, with use of the controller the user will be able to choose a proper height on which the tip of the limb will stand. This will significantly and comfortably facilitate the control of swelling.

Figure 35:
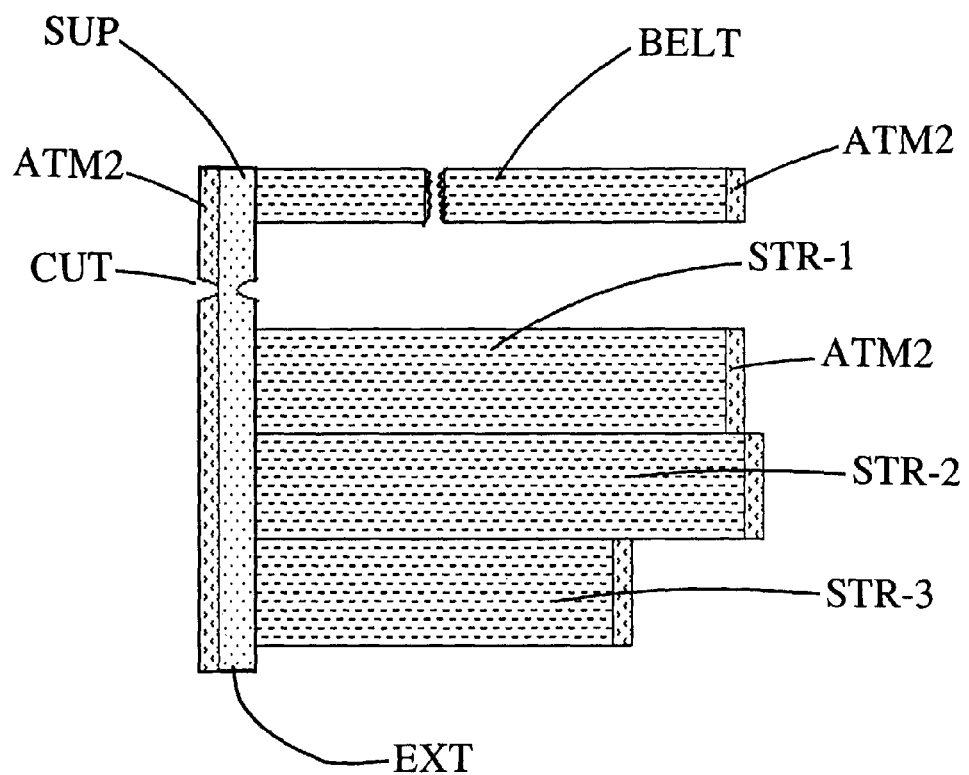
FIG. 35 shows a support unit for use in the thigh area.

FIG. 35 shows the general view of a support unit similar to the unit shown at FIGS. 6 and 33, except this unit is modified for use in the thigh area. This unit also uses a support, SUP, that has a long, rather rectangular shape with cuts, CUT in the sides to stand on the hip joint and functions as a hinge. The upper part of the support, SUP, is for placement on the waist and its lower part will be placed outside of the lateral side of the SUP, to rotate in the different directions without being disconnected from the upper part.

The support, SUP, has a series of straps attached to it. The first strap functions as the belt and is marked at BELT. This will hold the support and prevent if from falling. Other straps, STR-1, STRD-2, and STR-3, are attached to the support unit on a permanent basis in one side. These straps will wrap around the thigh and attach to the body of the strap with use of their own properties and the presence of the hook fastener attachment means, ATM2, at their ends on a detachable, re-attachable basis (as shown for the leg support). These straps are properly-sized to wrap around the thigh from the groin area to the upper knee. Importantly, the support, SUP, may have an extension to cover the knee area with a strap going around the knee.

Importantly, the extension, shown at EXT, will allow the attachment of this unit to the support of the unit for the leg.

Importantly, the effective length of these straps may be modified by use of the methods and means explained in different parts of this application. Similar to the leg straps, this method allows the support and straps to be used for dressing and supporting the thigh in a very practical, adjustable manner. In this model the straps are also made from one or two layers of LYCRA (TM) and the support means, SUP, is made from non-stretchable, clear vinyl or a laminated body with an outer surface made from a layer of loop attachment means, ATM1. It may also be made from any other materials such as fabrics or any other proper manmade materials. The support may have openings to allow sweat and air to pass through and also allows gauze pad or a long, removeable layer of lining shown at, LIN, in FIG. 6A or pad to be placed under it to prevent irritation, place pressure, and allow application of medication, etc. This unit may allow electrical leads to be held in place as well, in order to allow a programmed stimulation of the thigh muscles and tissues for various reasons such as prevention of muscle weakness or prevention of phlebitis.

The advantage of this unit is that it allows pressure in every special part of the thigh to be adjusted easily and the unit itself can be removed and placed with ease. When a lining is used it may be attached to the support, SUP, of the unit on a detachable, re-attachable basis. This allows the lining to be washed and used, or exchanged as needed.

Please note that these straps are not attached to each other and are separate.

Importantly, the straps may be attached to the support unit independently by having both ends attached to each side of the support on a detachable, re-attachable basis.

Importantly, the straps may be made from a continuous layer of lycra, or an elastic material, to allow a uniform coverage of the area although their end pieces will be separate to allow easy placement. An example of this model is shown for the leg and will not be repeated to avoid a lengthy application.

Method of use.
1. The user will place the support, SUP, on the side of the hip so that the cut, CUT, will be at the hip joint.
2. The user will wrap the belt, BELT, around the waist and attach its free end to the outer surface of the support, SUP, and then extend and attach the free end of the belt to the outer surface of its own. This is possible due to the presence of the attachment means.
3. The user will wrap the stretchable straps, STR-1, STR-2 and STR-3, around the thigh and attach their free end to the hook fastener attachment means of the support marked at H-ATM2, and will continue to attach the free ends of the straps to the outer surface of their own if the strap was longer.
4. Further adjustments allows the unit to be in its proper condition.

Figure 36:
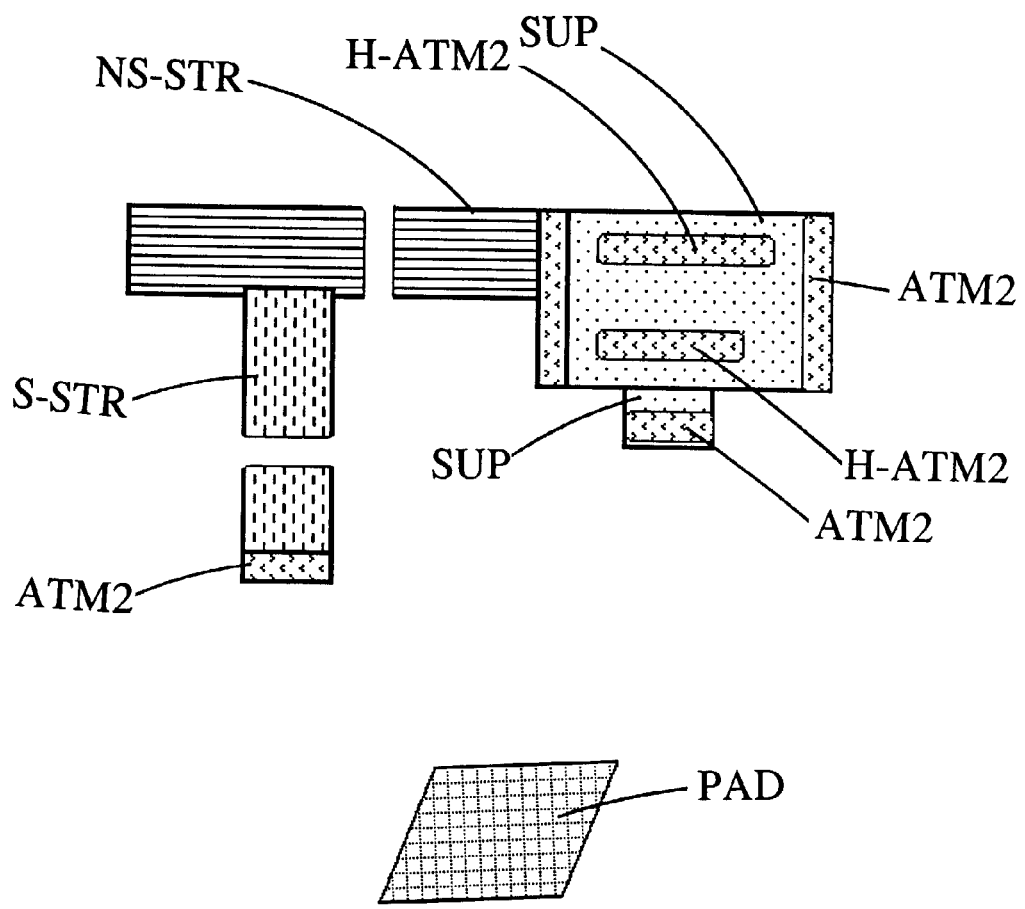
FIG. 36 shows a support unit modified for use in the groin area.

FIG. 36 shows the general view of a support unit that is similar to the unit shown at FIG. 35, except that it is modified for use in the groin area to hold a pad over the wound area in the inguinal region. A sample of such a pad is shown at, PAD, which has a trapezoid-shape and can be used after cases such as a hernia surgery in this region. This unit has a support, SUP, that extends and moves down to cover the inguinal area. The body of this support is made from a non-stretchable layer, such as a laminated body, with an outer surface made from a layer of loop fastener attachment means, ATM1, an inner soft lining for contact skin with a thin layer of foam in between. It may also be made from any other manmade materials. The support, SUP, will be held in place securely by a non-stretchable strap, NS-STR, that is attached to the support, SUP, on one side in a permanent, or detachable, re-attachable basis, and allows the other end of the strap to wrap around the waist and function as a sturdy belt. This strap will hold the support, SUP, in a stable position. Please note that due to the extra length of the strap, NS-STR it is schematically shown with a cut in its length. A second, but stretchable, strap, S-STR, is attached to the body of the NS-STR, on a detachable, re-attachable basis, in the posterior part of the NS-STR. This method allows the stretchable strap, S-STR, to move down the buttock area of the patient and pass the inner side of the groin, moving up and attaching to the horizontal hook fastener attachment means of the support marked at H-ATM2. This combination makes a secure unit for holding the support unit and compresses the pad, PAD, on the wound area in the groin.

Importantly, when the stretchable strap, S-STR, is made from LYCRA (TM) it will:
1. Expand in the back to function as a comfortable layer of fabric
2. Shrink and roll in the groin area to limit its presence and the pressure to the sides of the groin.
3. Expand like a wing and cover a wider area in the inguinal area, to hold the support means, SUP, in a stable condition. This combination will make a fine unit for this use.

Importantly, the stretchable strap, S-STR, attaches to the body of the NS-STR on a detachable, reattachable basis so that the position and location of such an attachment can be changed as needed.

Importantly, the straps may be attached to the support unit independently, by having both their ends attached to each side of the support on a detachable, re-attachable basis.

Method of use.
1. The user will place the combination of the pad, PAD and support, SUP on the inguinal wound site.

2. The user will wrap the non-stretchable strap, NS-STR around the waist and attach its free end to the outer surface of the support, SUP, due to the presence of the attachment means.
3. The user will move the stretchable, strap, S-STR, down from the buttock area and pass it from the inner side of the groin, moving it up and attaching it to the horizontal hook fastener attachment means of the support marked at H-ATM2.
4. Further adjustments allows the unit to be in its proper condition.

DETAILED EXPLANATION OF THE INVENTION

This invention is related to the problems with wound care and wound dressing in body of humans and animals. Commonly gauze pad/s or wound dressings are used and are held in place by use of adhesive tapes or wrapped around the limbs. However, the use of adhesives has multiple problems as follows:
1. It is difficult to use with elastic gloves, since the adhesive tapes stick to the gloves and makes this job hard.
2. The adhesive tapes cause skin irritations and create discomfort on removal. Also they simply do not adhere to the skin properly, when the wound area is covered with hair. Many times the hair has to be shaved which is a process of its own.
3. Some wounds need frequent inspections or exchange of the dressing. The removal and adhering adhesive tapes over and over, multiplying their problems.
4. There are many wounds in the limbs and body that need wrapping and this can not be done by use of adhesive tapes effectively and conveniently.
5. The issue of dressing with one hand is also an important issue that will be helped by use of these units.
6. The dressing of the ulcers in the toes and heels are difficult and time-consuming, and so better units will be helpful.
7. Also performing the wound dressing as quickly as possible is a vital issue, and may make a big difference in daily life and in manmade or natural disasters. Therefore, the methods and means used in this application are aimed to reduce the time needed for such an action to the least possible.
8. Another important issue is handling the wound swelling and edema in dependent areas of the body and after certain intervention such as removal of a breast that disrupts the normal fluid drainage.

This application introduces methods and means of dressings that not only will simplify the process, it will decrease the use of adhesives and makes this process easier for use with medical gloves. These goals are achieved by the following methods and means:
1. The use of support units and wound dressing as shown at FIGS. 3 and 4 and wrapping methods that use little adhesives and are held in place with use of straps and bands. Very importantly, the applicant has introduced a use of straps and wrapping means shown at FIGS. 1-6 that are made from special, elastic fabric that functions as a loop fastener attachment means. This applicant believes he is the first to introduce the use of this particular unit for this purpose.

The body of these straps, STR, is made from a woven fabric, comprising elastic threads providing stretchability of the fabric. The fabric also has a woven construction that provides the VELCRO (TM) hook material to separably hook onto the woven fabric. The applicant has used the combinations of swimwear fabric, LYCRA (TM), to function quite well for this purpose. The applicant considers this combination to be the very useful tool for making these units and many other similar units. Therefore, he reserves his right to ask for patent for this combination alone for use in construction of different materials for various uses.

This material has the following favorable properties and characteristics:
a. It has an elastic body which pulls the attached units, such as support units, and keeps them in place with a reasonable tension. This mild, comfortable, non-strangulating, and uniform tension is an important property for the use of this material in many of the wound dressings since it functions well with the skin. Importantly, it stretches when the underlying part of the body such as a joint moves.
b. The strap stretches, conforms and accepts the shape of the area, which is also very important since it makes this unit to be properly used in many areas of the body and stands on curved areas, such as the legs, arms etc., easily and comfortably.
c. Very importantly, it functions as an attachment means for the attachment of the hook fastener attachment means, VELCRO (TM). This makes a very unique property and allows the hook attachment means to attach to this strap on a detachable, re-attachable basis in any desired area, which is very convenient and important.
d. The above mentioned properties of this unit allows the effective length of this strap to be chosen and adjusted easily.
e. The material is soft and comfortable and does not irritate the skin.
f. The material is thin and allows it to be used without much difficulty.
g. The material is a thin fabric which allows heat and sweat to dissipate.
h. Structurally, this fabric is a thin woven fabric that allows it to be stretched in one direction more than the other, and has one face that is shiny and has properties that the hook fastening properties will engage with it on a detachable basis. It is reasonable to believe that the construction of this fabric to be modified to make new kinds with following properties.
1. To have loop fastener attachment means properties on both its front and rear surfaces.
2. To have different thicknesses and still function as the loop fastener attachment means. This is to allow a different degree of tension to be provided.
3. To alter the elasticity of these fabric in order to produce fabrics with different degree of tension in their body for different uses.
4. The applicant believes that modification of this fabric is possible to make a unit that its attachment function to a hook fastener will be enhanced and improved.
5. To stretch in both directions.

The applicant has previously discussed the properties of this fabric with his patent lawyer but still has not be able to define this material in any other way. Although, he claims that these units will be made with other fabrics, also, that have those properties.

This material which is commercially available with name of "Lycra" (TM) is a woven fabric, made from a polymer that has a rather shiny surface on one side that functions as the loop fastener attachment means. The other side is not as shiny and has a weaker loop fastener attachment means.

Importantly, the applicant has sewn, or attached, two layers of this fabric to make a thicker fabric that provides more elastic power with double the sides-loop-fastening attachment means function.

The applicant introduces these straps as one important part of this application. Furthermore, more modifications of these straps can be made as follows:

The body of these straps may be modified by adding bands of stretchable, non-stretchable or shaped pieces such as a layer of latex material, vinyl, a polymer, latex paints, elastic or rubber means or similar materials to them. These parts may be embedded inside their body during the manufacturing process or they may be applied, attached, adhered or fixed onto them at a later time. These bands function to prevent the thin body of these straps from changing, curling, etc. The elastic means will allow this unit to expand and retract as well. Importantly, this interaction allows the development of a particular shape for a special use, such as that of the elbows, knees, heels, etc. This construction, when stretchable, allows the unit to conform to accept the shape of the part of the body.

The straps may have different shapes or sizes, the reason for which being to provide a special configuration or body to some parts of these straps.

Importantly, an elastic strap with an adjustable end piece such as a buckle system may be used with these support units as well. The use of such units allows the effective length of the elastic strap to be modified. It is very important however, to note that the use of buckles and similar units that can modified the effective length of any elastic fabric is still different from the use of these straps due to its special property.

The applicant also has noticed that attaching this fabric to the surface of a sponge layer makes it stronger.

The supports and their functions.

The supports are mainly made from a non-stretchable materials, such as:

1. Clear PVCs that allow the underlying area such as wound site to be seen for bleeding, etc.
2. Use of a laminated material that is available and is a non-stretchable, material made with a layer fabric in its outer surface that functions as the loop fastener attachment means, ATM1, and an inner part which is a layer of soft lining for placement on skin, with a layer of foam sandwiched between them.
3. The support may be made from screens, different fabrics, or other manmade materials.
4. Particular supports may be made by modifying the elastic fabrics by adding bands of stretchable, non-stretchable or shaped pieces such as a layer of latex material, vinyl, a polymer, latex paints, elastic or rubber means, or similar materials. One model of such modifications is shown at FIG. 8, which shows the front view of a special, stretchable support unit made from shaping the same material used for the strap, STR or lycra (TM). Here the Lycra is modified with use of bands made from materials such as latex as shown at L-BAND. The shaping of this stretchable material by this method or the use of sewing techniques creates an elastic, shaped support. Such a support is useful in areas with a particular shape and function, such as the knees, ankles, elbows, toes, etc. This shaped, stretchable support, SUP, allows better handling and placement of these units.
5. In some cases the supports are made from stretchable materials or the stretchable part of the strap stands on the wound.

The function of the supports are very important in these units as following:
1. They stand on the wound site and keep the dressing in place.
2. In some cases they function as a vital piece that allows the straps to be handled easily, be placed to hold the unit together and prevent it from moving. Although the placement of the first strap may not be perfect, in practice it allows the second and third straps to be placed more precisely. Then, the user can go back and re-position the first strap and other straps to achieve the best result. This function will otherwise not be possible by one operator only, thus such function of the supports is extremely important and vital.
3. In many units the other vital roles of the supports is its function as the stabilizer, to make the units to stable and prevent the straps from moving. For example, in areas such as the leg and forearm, the limb has a wider body in proximal area, which varies in its shape and decreases gradually. These are areas that move, as well, and cause wrapped material to slide to the thinner distal area such as the ankle and wrist. This can be easily-controlled with use of a strap that matches the length of these limbs and uses multiple straps as shown in FIGS. 6, 7A, 33 and 35.

Please note that support may be made to be simple, narrow, to bend to rotate and from different materials and to have different shapes. It can be a very simple support with a narrow body but still to allow the strap to attach and function. It can be made to be complicated with having various forms and attachment means.

4. The use of supports with multiple straps allows the tension of the straps in one segment to be adjusted while the other straps stay stable in their place. This function is also very important in areas such as the legs, where adjustment of the tension in one segment may be needed.
5. Importantly, combinations of multiple supports and straps as specified in this application allow parts of the body that are commonly very difficult to be wound dressed or supported to be handled with ease. Examples of these models are shown for the head and chin at FIGS. 19-21, for the shoulder at FIGS. 22-23, for the elbow at Figure, 25, for the hip at FIGS. 26-26B, and for the arm/hands at FIG. 35.
6. In some other cases the support may function as a protective means that shields the wound from coming into contact with unwanted objects. An example of such a unit is shown at FIG. 26C-D. These figures show schematically a protective support unit for the chest, in which a rather rigid support is held away from the wound site by use of walls made from foams and is kept in place with use of straps. This particular unit is designed to keep the clothing away from the wound after open-heart surgeries. Importantly, although it can be modified to be used in any other wound that needed such a protection in head, neck, body or limbs. It is important to note that the use of multiple straps in different directions allows such a unit to be held in place with ease, which would otherwise be impossible.

By use of these basic ideas, methods, and means the applicant has designed multiple units that are useful in solving the problem wit wound dressing, compression and supports in various areas of the body. In the following parts he specifies how the basic units are modified for use in different areas.

FIGS. 1 and 2 shows the front and side view of a wound dressing unit that consists of a clear front support, SUP, with a strap (STR) attached to it on the left side of the support. In this model the support, SUP, is made from a layer of vinyl and has zones of hook fastener attachment means shown at ATM2, made from hook type of hook-loop fastener VELCRO (TM). These zones are further specified by ATM2-A, ATM2-B and ATM2-S. The hook fastener zones allow the body of the strap, STR, which has loop-type of attachment means, to attach to the hook fastener attachment means shown at ATM2, on a detachable, re-attachable basis. As mentioned in the text, this strap is made from special material such as lycra (TM) that allows it to attach to the hook fastener attachment means, ATM2, on a detachable, re-attachable basis. The free end piece of the strap, STR, has a band of hook fastener attachment means, ATM2, (this band may be double-sided) that allows it to be attached to the rear surface of the body of the strap, STR, on a detachable, re-attachable basis. The zones of the hook fastener attachment means, ATM2-A and ATM2-B, allow pieces which functions as loop fastener attachment means such as the body of the strap, STR, to be attached to them on a detachable, re-attachable basis. An example of this is shown at FIGS. 3 and 4.

The free end of the strap, STR, may have a piece of adhesive tape, ADT, which allows it to be attached to the rear surface of the strap in order to keep the free end of the strap, STR, stable should the ATM2 not attach to it. Instead of the adhesive tape, ADT, this attachment may be achieved through any other means or materials such as:
1. Snaps
2. Magnetic means.
3. Various attachment means that are available or that can be yet designed.

The main issue is to allow the free end of the strap to be attached to the surface of the strap, STR, on a detachable, re-attachable basis. The adhesive tape, ADT, has a layer of adhesive, ADH, protected by a removeable cover, PC, shown best at FIG. 2. The protected cover, PC, will be peeled off before use. The protective cover, PC, of the adhesive tape is folded to allow it to be removed without allowing the gloves to touch the adhesive layer.

This unit uses at least two means to allow the unit to be placed by one hand only.
1. Use of special pieces shown at YD, which are best shown at YD at FIG. 2.
2. Use of bands BAND-A, BAND-B as shown in FIGS. 3-4.

The YD pieces were previously introduced by this applicant to the patent office. As shown at FIGS. 2, these pieces are made from a rectangular-piece fabric or a polymer that has a layer of medical adhesive, ADH, on one side, protected with a piece of folded protected layer, PC, and a zone of loop fastener attachment means shown at, ATM1, on its lower surface. This construction allows the zone of, ATM1, to be attached to the zone of, ATM2, from the support unit, on a detachable, re-attachable basis. The rear surface of the piece, YD, may have a zone of hook fastener attachment means, ATM2, of its own that allows a piece of loop fastener attachment means such as the strap to attach to it on a detachable, re-attachable basis.

The advantage of the piece, YD, is that it allows the removal of the protective layer, PC, and adherence to the skin. In this way, the person can use this unit with one hand and then exchange the wound dressing without the need to use another adhesive part each time since the YD piece can be separated from the support, SUP, on a detachable, re-attachable basis.

The support, SUP, may also have a piece of gauze pad, GP, attached to for being ready for use, as shown in FIG. 2. This will eliminate the time for preparation of the gauze piece since time can be critical in many such circumstances. The gauze pad, GP, is attached to the body of the support, SUP, by an attachment means shown at, ATM, or an adhesive layer that allows the gauze pad, GP, to be exchanged when needed.

Importantly, the body of the support may have a series of holes or openings that allow air, sweat and other gasses to pass through, also it may have a series of tabs on its surface to allow it to be held and moved on the wound site easily. Importantly, this basic unit can be modified to be used in different places such as chest, hip, abdomen, knees, extremities, etc.

FIG. 2 shows the vertical, cross-cut view of the wound dressing unit shown at FIG. 1.

FIGS. 3 and 4 show the front and side view of a wound dressing unit similar to the unit shown at previous FIGS. 1 and 2 except this unit has two bands made of a material similar to the strap, STR. These bands, BAND-A and BAND-B, are designed to attach to the attachment zones, ATM2-A and ATM2-B of the support, SUP, on a detachable, re-attachable basis. In this model the strap, STR, and bands, BAND-A AND BAND-B, are made from lycra (TM) that allows these pieces to attach to the hook fastener attachment means, ATM2, on a detachable, re-attachable basis. The free end of the strap shown in left side is similar to the model shown at FIGS. 1 and 2.

The significant importance of this unit is that it allows the person to dress a wound with use of only one hand, which the applicant believes it is extremely important. At the time of use the person:

First. Places the support, SUP, on the wound and places the strap, STR, under the limb so that by pressing on the strap, STR, by the limb it will temporarily prevent the support, SUP, from moving.

Second. The person wraps the proximal band: Band-A around the limb on the opposite side of the strap, STR, and bring its free end to attach to the ATM2-A, from the support, SUP, on detachable, re-attachable basis.

Third. Then he/she wraps the distal band: Band-B around the limb in the opposite side of the strap, STR, and bring its free end and attach it to the ATM2-B on the support, SUP, on a detachable, re-attachable basis.

Fourth. The user wraps the strap, STR, around the limb for attachment to the ATM2-S on the side of the support, SUP, on a detachable, re-attachable basis. Then he/she can wrap the end of the strap, STR, around the outer surface of the strap, STR, to attach the adhesive tape, ADT, from the end of the strap to the rear surface of the strap. Alternatively, a hook fastener attachment means, ATM2, may be used for such a purpose. This process takes about 15-20 seconds of time or less, and makes a very stable and easy method of wrapping a wound by one hand only.

Importantly, the user may use a stand shown at FIG. 11 to facilitate this process.

FIG. 4 shows the vertical, cross-cut view of a wound dressing unit shown at FIG. 3.

Importantly, the method of the handling of the extra strap or free end of the strap can be different by:
1. The use of adhesives that allow the end of the strap to be attached to the rear surface of its own in any particular location. The applicant has used adhesives tapes that allows the adhesion to occur on a detachable, re-attachable basis and more than a few times.
2. The use of attachment means that allow the end of the strap to be attached to its own rear in any optional location. The applicant has used hook-loop fastener attachment means for this purpose. The free end of the strap has a hook fastener which allows the free end of the strap, STR, to attach to the rear surface of the strap, STR, in any location and on a detachable, re-attachable basis.
3. The applicant believes that other attachment means may be made to allow the free end of the strap to attached to the body or the surface of the strap or its free end. This attachment will be made on a detachable, re-attachable basis. This is to allow the free end of the strap to be attached to the rear surface of its own in any optional location. Mechanical means, buckle means or similar units may be also made to allow that piece to be attached to:

a. the body of the strap, STR.
b. to the free end of the strap, STR, or both, to allow this piece or means to be attached during initial use and allow the future attachments of the free end to the body of the strap on a detachable, re-attachable basis.

FIG. 5 shows the front view of a support unit, SUP, which has a non-stretchable body (or, in some cases, stretchable) it has openings, OP, that allows air and gasses to pass. It has the zones of the attachment means, ATM2, made from hook type of hook-loop-fastener and are further specified by ATM2-A, ATM2-B and ATM2-S. Importantly, many of the supports used for the units in this application use a material that is now commercially available and has an outer surface made from a layer of loop-fastener attachment means, ATM1. The use of this material with zones of hook-fastener attachment means, ATM2, gives the option of attaching straps with both loop-fastener body and hook-fastener end pieces. Also importantly, the double-sided, hook-fastener pieces such as the one shown at FIGS. 18 and 18A may be used with these units, with or without adhesive zones. Importantly, a double-sided, ATM2, piece will allow a strap and a support with loop-fasteners to be attached to each other on a detachable, re-attachable basis.

Importantly, instead of the zones of the attachment means (ATM2-A) and (ATM2-B), the unit may have a second long zone of the hook-fastener attachment means, such as the zone, ATM2-S, on the left border of the support, SUP. This will allow the strap, STR or the bands BAND-A, BAND-B to occur. The support may have cuts on its borders to allow the support to bend and shape in places such as over the joints, as shown at CUT in FIG. 35.

FIG. 5A shows the front view of a support unit, SUP, which is similar to the model shown at FIG. 5, except here the support is made from a body with an outer surface made of a layer of loop-fastener attachment means, ATM1. This support, SUP, has a second support piece, referred to as Support A, SUP-A, that is attached to the body of the first support along the Attachment Line, AL. The free end of Support A, SUP-A, has a zone of hook-fastener attachment means, L-ATM2, that allows it to attach to the outer surface of the first support, SUP on a detachable, re-attachable basis. The advantage of the second support, SUP-A is that it allows tubings, wires, suction bulbs, etc., to be kept securely between these two layers. The outer surface of the second support, SUP-A has a pocket, POC, of its own that allows a suction bulb to be placed inside it as well, if needed.

This unit will have a strap that will be attached to one side of support, SUP, and the free end of the strap will attach to the attachment means, ATM2, of this support as explained previously. These units may be placed in the arm, around the limb, chest, abdomen, etc.

FIG. 6 shows the general view of a support unit similar to the unit shown at FIG. 1 except this unit is modified for use on the leg area and to support the legs as well. This unit allows a secure and easy dressing of the leg without the need for adhesive tapes. In this model the support, SUP, has a long, rather rectangular-shape and is placed on the front of the leg, or onto the wound site. The support, SUP, is shown in more detail at FIG. 6A. It has a long zone of hook-type attachment means, ATM2, on its right border that allows pieces made of loop-fastener attachment means, ATM1 to be attached to it on a detachable, re-attachable basis. The left border of the support unit, SUP, is attached to three straps: STR1, STR2 and STR3. These straps are attached to the support unit on a permanent basis, although importantly, they may be attached to the support on a detachable, re-attachable basis. These straps are sized to wrap around the leg on its upper, middle and lower part, and will attach to the support, SUP, by use of pieces of loop-fastener attachment means. Their ends, shown at ATM1-1, ATM1-2 AND ATM1-3, are respectively attached to the end of the straps STR1, STR2 AND STR3 on a detachable, re-attachable basis. The applicant made this method for dressing/supporting the legs and thighs in a very practical, adjustable fashion. In this model the straps are also made from one or two layers of lycra (TM) and the support means are made from vinyl, though it may be also made from any other materials such as fabrics, or other manmade materials. The support may have openings in it to allow the sweat and air to pass through. The support also allows a gauze pad or a long, removeable layer of lining, shown at LIN, in FIG. 6A or a pad to be placed under it. The lining of the pad prevents irritation, and also allows application of pressure in the area, or medication, to be applied as well.

Importantly, this unit allows electrical leads/pads to be held in place for a programmed stimulation of the leg muscles and tissues. This will be done for various reasons such as prevention of muscle weakness or of phlebitis.

Importantly, these units are very valuable, since they allow the pressure in different segments of the leg to be adjusted. Also importantly, the unit can be removed and applied easily and can be placed over the regular stocking and pants as well.

The lining will be attached to the support, SUP, on a detachable, re-attachable basis, to allow washing or exchanging. This model can be made to extend to the thigh area as was shown in this applicants previous applications. In this model a couple of straps will attach the thigh piece to a waist strap in order to prevent it from falling. Importantly, the straps of this unit may be attached to the body of the support unit independently, by having the one end of the straps to be attached to one border of the support and the other end of the strap to be attached to the other border of the support both on a detachable, re-attachable basis. This was shown by this applicant in his previous models and applications to USPTO.

FIG. 6A shows the general view of the support unit shown at FIG. 6. In this figure the body of the support is shown at SUP, and it has openings, OP, a long zone of hook-fastener attachment means, ATM2, which is shown on its right border. A layer of lining, LIN, is attached to the rear surface of the support, SUP, and extends from its borders. The lining, LIN, is attached to the body of the support on detachable, re-attachable basis to allow the exchange.

FIG. 6B shows schematically a support unit similar to the unit shown at FIG. 6 placed on a leg.

Besides, this unit has three straps which each have their own attachment means and are attached to the support, SUP on a detachable, re-attachable basis. The support, SUP, of this unit has one long zone of hook-fastener attachment means, ATM2, on the right and left border of its body. This model allows the effective length of the straps to be adjusted from the both ends of the straps. The three straps are further marked as: STR1, STR2 AND STR3, and they are attached to the support unit by use of the loop-fastener attachment means, ATM1, which are part of the free ends of the straps. When the straps have the loop-fastener attachment property of their own they will attach to the support themselves. These straps are properly sized to wrap around the leg on its upper, middle and lower part. They can be attached to the support, SUP, by use of the pieces of loop-fastener attachment means at their ends shown at ATM1-1, ATM1-2 AND ATM1-3 which are respectively attached to the one end of the straps STR1, STR2, AND STR3. The other ends of the straps have similar attachment pieces as well, which are not marked in this figure to prevent a crowded picture. In this model the straps are also made from one or two layers of Lycra (TM) and the support means are made from clear vinyl, though they may also be made from any other materials such as fabric or other manmade materials.

FIG. 6C shows schematically, the general view of a support unit similar to the unit shown at FIG. 6, except in this unit the body of the strap is made from a non-segmented fabric, marked CSTR. This fabric is attached to the body of the support along one of its border in one side and continues to wrap around the leg but ends with three separate loop-fastener attachment means, ATM1-1, ATM1-2 AND ATM1-3. The end pieces allow the end units to attach to the hook-fastener attachment means, ATM2 from the support, SUP, on a detachable, re-attachable basis. Importantly, the value of this model lies in the fact that the continuous body of the strap does not leave an open area or a line of compression on the legs. Importantly, this unit also chosen to show that one strap may have more than one ending.

FIGS. 7 and 7A show the front and side views of a support unit similar to the unit shown at FIGS. 5 and 6 which were modified by adding a U shape extension to its lower end. FIG. 7 shows the front and side views of a support unit similar to the unit shown at FIG. 5, which is modified by adding a U-shape extension to it. This unit is designed to support the middle and lower ankle area in both sides of the ankle, inside and out, and allows the compression of those areas. In this model a support piece similar to the support, SUP, shown at FIG. 5 or an extension of the support of the leg support is utilized and shown as the inner support, I-SUP, and functions to compress the inner part of the ankle. This support, I-SUP, moves down and covers the inner ankle and connects to a piece of an elastic strap shown at U-STR. This U-strap makes a U-turn under the foot and attaches to another non-stretchable support that functions as the outer support, O-SUP. This compresses and supports the outer ankle area and has a band, C-BAND, which is an elastic strap that wraps around the lower leg or ankle area and holds the O-SUP in place. The C-BAND allows a wider strap, such as STR3, shown at FIG. 6B to wrap around the I-SUP AND O-SUP keep these supports in place, squeezing the tissue in between them. The importance of this unit is:

A. The U-shaped support means supports the middle, lower and lateral part of the ankle and allows the compression of the tissues in these areas. The importance of this unit is that it allows dressing and compression of the tissue and vessels on the lower inner ankle-foot area to occur for a better result and in a measurable with placement of a balloon connected to a gauge and adjustable manner. The use of this unit is in vascular problems, particularly in venous insufficiencies of the legs, where compression of vessels for decreasing the inner pressure of the vessels and prevention of extravasation of fluid in this area is needed. Please note that in order to prevent confusion, the upper parts of the unit are not shown in this figure.

Importantly, in some cases there is a need for further compression of the lower leg to raise the amount of pressure on the tissue. In such cases the inner support, I-SUP and the outer support, O-SUP, are made from rather rigid pieces such as a shaped polymer or metal that are connected to each other in the lower side by a strap. The position of this strap on the supports is adjustable and allows the distance of these two inner support, I-SUP, and the outer support, O-SUP, to be adjusted. Importantly, the outer surfaces of the inner support, I-SUP, and the outer support, O-SUP, have attachment means, such as hook-fastener attachment means, ATM2. This allows a wider, horizontal strap or two straps similar to one shown at C-BAND to wrap around the lower leg and hold the I-SUP and the O-SUP in place to further compress the tissues in this area. This combination can be used as a separate unit, or in combination with the leg support. Importantly, the rigid supports can be a pre-shaped or alternatively made from a material which accepts the shape of the area after placement. Pieces of shaped foams or pads may also be placed between the wound dressing and these supports. A flat, fluid-filled balloon attached to a measurement unit may be placed between the support and lining to monitor the pressure in the wound.

FIG. 7A shows a support unit for the leg as shown at FIG. 6C, except this figure shows a U-shaped extension attached to it. In this figure the support, shown at FIG. 6C, has an extension which will function as the inner support, I-SUP. This piece moves down and covers the inner ankle and then connects to a piece of strap shown at U-STR. This follows a model which was shown at FIG. 7.

FIG. 8 shows the front view of a special stretchable support unit made from shaping the same material used for the strap or the LYCRA (TM). Here, the Lycra is modified with use of bands made from materials such as latex as shown at L-BAND. The shaping of this stretchable material or the use of sewing techniques allow an elastic, shaped support to be made. Such a support is useful in areas with a particular shape and function, such as knees, ankles, elbows, toes, etc. This shaped, stretchable support allows better handling and placement of these units. Importantly, the following advantages are also available:

a. In this method the support has an elastic body that will be pulled to keep it in place with a comfortable tension. This mild, comfortable tension is an important property for use in these areas.
b. The support unit stretches and conforms to some degree and accepts the shape of the area. Also, such a body allows this body of the support to change with change of the wound areas such as over joints, knees, ankles, hips, elbows with extension and closure.
c. The inner part of the support is a soft, non-irritant fabric and does not cause skin reaction.
d. On the scalp it allows an easy dressing of the wound.
e. Importantly, the side where the strap is attached stretches in both direction and allows this unit to fit a shaped area, such as the scalp. A transverse strap allow this unit to be further stable on the scalp. This will make a cross-shaped unit.

In this figure the attachment means of the support is shown at ATM2 and the strap at STR. A D-Ring may also allow the strap to be adjusted.

FIG. 9. Shows a long strap that is attached to a transparent support, SUP. This figure also illustrates two important parts:
1. a transparent pocket for placement of information, here referred to as the Information Pocket, IP which is on the support, SUP or on the strap. The Information Pocket, IP, allows a piece of paper, consisting information to be placed inside the pocket. This information may be, for example, time of the use of the dressing, medication underlying IV line, or other information about the person using the unit, etc., and can be exchanged as needed.
  Importantly, the information pocket, IP, may be placed on the wall of the strap to be part of the wall or simply attached to it.
2. Importantly, the body of the straps, STR, may have zones of materials such as latex, LA, in or on it in order to allow the shape of the strap to be conformed or modified to a desired shape. It can be used to prevent curling of the strap, etc. The shape, width, thickness, materials utilized, and other characteristics of these zones may vary.

FIG. 10. Shows schematically the use of D-Rings with the support unit. In this figure a transparent support, SUP has a D ring, D-RING on its right side that allows the strap of the unit to go through, make a U-turn, and attach to its own surface. This is another method of adjusting the length of the strap as mentioned in the text.

FIG. 11. Shows schematically a cradle, CR, on a stand that allows a limb to be placed on it. The angle and height of the cradle can be adjusted by means connected to the base, BA. The height can be adjusted by control of the height of the pole, PO and the angulation by the hinge, HI. This unit allows a strap or the support part of the support unit, shown at FIGS. 3-4 to be placed on the cradle of this unit and be attached to it by use of a weak adhesive or by a detachable, re-attachable means. Thus, the combination allows the user to place the support on a limb with one hand and adjust its size and tension.

FIG. 12 shows a general view of the rear piece of a support unit designed for use for the supporting of the wounds on the heels and toes. In this figure the piece that stands on the heel is shown at, HE and it has a lower sole, SOL-1 that has a hook-fastener attachment means, ATM2, on its surface. This piece also has a strap, STR-1 with a zone of hook-fastener, attachment means, ATM2, on its end this piece complements the piece shown at FIG. 13 to make a unit shown at FIG. 14.

Importantly, these heel and toe pieces which may be made from shaped lycra (TM) or similar fabric, with use of latex material as mentioned, so that this combination will:
a. Be soft, non-irritant and comfortable.
b. Allow the unit to be pulled to accept the form of the underlying area and fit well.
c. Allow one size to be used in many patients.
d. Allow the pieces to be placed inside one another and so that many of them, such as 15-20 at a time, may be placed inside one box, thus reducing storage size.
e. Allow the patients themselves to adjust the length of the unit as needed.
f. Importantly, both the heel and front pieces may have a cut with a strap on their lengths to allow their width to be adjusted as well. The strap will hold the open area in control.
g. Importantly, both the heel and front pieces themselves may be made from two pieces to allow the width to be adjusted as one piece can be attached to the other one along a zone of attachment of a detachable, re-attachable basis.
h, Importantly, these pieces may be made from other shaped materials.

Importantly, the attachment means will be complementary and one attachment means, ATM, will be faced with a complementary attachment means on the other side. Or, the body of the shaped areas will function as the complementary attachment means. This method allows, for example, the attachment means in the straps to be hook-fastener attachment means, ATM2, to be attached to the surface of the body of the heels made from loop-fastener attachment means.

FIG. 13 shows the general view of the front piece of the support unit shown at FIG. 12. In this figure the front piece, FR, also has a sole, SOL-2, that allows the hook-fastener attachment means, ATM2, from the rear piece shown at FIG. 12 to attach to its surface on a detachable, re-attachable basis. This piece has a strap with a piece of hook-fastener attachment means on its end. The front and rear pieces of these units are made from shaped materials.

FIG. 14 shows schematically the general view of the support unit for the heels and toes made from the combination of rear piece shown at FIG. 12, and front piece shown at FIG. 13. In this figure, sole, SOL-1, from the rear piece is attached to SOL-2 from the front piece on a detachable, re-attachable basis. Importantly, this allows the length of the unit to be adjusted. The strap STR-2 holds strap STR-1 from the rear piece and attaches to its own surface by the attachment means on a detachable, re-attachable basis. The strap STR-1 from the rear piece, HE, attaches to the body of the rear piece, HE, on a detachable, re-attachable basis.

FIG. 15 shows schematically a support unit for the heels and toes, made from the combination of the unit shown at FIG. 14, which is placed inside an outer piece that functions as the body of a shoe. The outer piece is made from a front sole shown at SOL-3 that is attached to the SOL-4 from a rear piece, OHE on a detachable, re-attachable basis. The combination is attached to the piece shown at FIG. 14 by attachment means between them.

This combination has the advantage of allowing an adjustable piece be used for use both in and out of the house. The outer piece will be removed inside the house and used when leaving the house.

The use of heel and foot protector with these units:
Importantly, these units allow pieces of foam to be attached to their surfaces in order to prevent bed sores in these areas. For this purpose, shaped sponges will be attached to these pieces and prevent the ankle so that its free end will attach to the attachment means, ATM1, from the strap, STR1.

This method will make a secure and simple means of holding the dressing of the toes in its place which is commonly difficult.

The support may be made from:
1. Elastic fabric
2. A regular fabric
3. A thicker unit such as body of the supports as mentioned.
4. Various materials may be used.
5. The attachment of the straps to the body of the support may vary.

However, making this unit from the LYCRA (TM) makes a very nice comfortable unit that has many advantage such as:
a. A support with an elastic body that will be pulled to keep it in place with a comfortable tension. This mild, comfortable, tension is an important property for keeping the dressing in place.
b. The support unit stretches and conforms to some degree and accepts the shape of the area.
c. The support is a soft, non-irritant fabric and does not cause skin reaction.

FIGS. 16-17A show a buckle means designed to allow the length of the strap to be adjusted and be a more durable and convenient, end piece for use with these units. This buckle initially allows the length of the strap to be adjusted and the strap to be fixed on it. Then it allows further adjustment of the position of the end of the strap on the support to be possible, since the buckle can be attached to the zone of the attachment means of the supports closer or further, depending on the width of the zone of the attachment means on the lower surface of the buckle.

In this figure, pieces of this buckle are shown. The extra length of the strap on the buckle allows its length to be adjusted. The snap, SNAP, allows the upper piece, UP, to be opened and the strap to be moved back and forth for the length adjustment. The details of these pieces are explained in the figures.

FIG. 18 shows the front view of an end unit, designed to allow the length of the strap to be adjusted. This unit has a rectangular, flat base, BASE, made from a layer of fabric with a zone of hook-fastener attachment means on its right side, ATM2, placed on its upper and lower surfaces. Here, the upper zone of attachment means, U-ATM2 is shown on the right side. A similar zone on the left side is made with a layer of adhesive on it, shown at ADH, at FIG. 18A, which is protected by a protective cover, PC. The inner edge of the protective cover is shown at BPC. The lower surface of the base in the right side also has attachment means, L-ATM2, best shown at FIG. 18A. This unit gives significant advantage and will allow the length of the strap to be adjusted for many units such as the heel and shoulder and other units.

At the time of use:
1. Initially this piece will be attached in a proper position to the body of the outer surface of the support, SUP.
2. Then the strap will be pulled to attach to the ATM2 zone of this piece, which will be possible due to the capability of the strap.
3. When the proper length of the strap is decided, then the extra piece of strap will be cut along the left border of the upper attachment means, ATM2 on the upper surface of this unit. Please note that at this point the strap is attached to hook-fastener attachment means, ATM2, from the upper surface of this piece.
4. Then the user will remove the protective cover, PC, and adhere the lower or base of this piece to the upper surface of the strap through use of the adhesive layer.

This combination will make:
a. The free end of the strap have a neat cut.
b. The combination make a zone of hook-fastener, attachment means, ATM2, in the lower surface of the free end of the strap that will be used to attach the free end of the strap to the outer surface of special supports that will accept this end. This will be very useful in units for use in various areas, such the heels and shoulder, etc.

The advantage of this unit is that allows a one-size unit to be used as a universal unit or will allow a better adjustment of the length of the straps.

FIG. 18A shows the cross cut view of the unit shown at FIG. 18. In this picture the unit has base, BASE, made from a layer of fabric, with a zone of hook, fastener, attachment means, ATM2 on its upper and lower surfaces shown in the right side. On the upper surface of the left half of the base, the fabric has a layer of adhesive, ADH, that has a protective cover, PC, on it. At the time of use this piece will be attached to the top surface of a matching support by virtue of the lower attachment means, L-ATM2. The elastic strap will attach to the upper attachment mean, U-ATM2, of end unit and with adjustment, proper length of the strap will be known and then the extra piece will be cut along the left border of the upper attachment means which is on the border of the protective cover. Then the user will remove the protective cover, PC, and adhere the base to the upper surface of the strap. This will make a clean-cut side and the combination will make a zone of attachment means, ATM2, on the lower end of the strap that will be used to attach the end of the strap to the surface of the units for use in the heel and shoulder, etc.

FIG. 18B (also note FIG. 18C) shows the front view of an end unit shown at FIG. 18 that is placed on a support, SUP. This support has a non-stretchable body with an outer surface made from a layer of loop-fastener, attachment means, ATM1, its inner surface being a soft lining that stands on the skin, and a thin layer of foam sandwiched in between. The strap, STR, is attached to the right border of the support. The outer surface of the left border of the support, SUP, has a long, narrow zone of hook-fastener attachment means, ATM2. The end unit piece is attached to the surface of the support, SUP, due to the attachment means, ATM2, in its lower surface, this part is shown better in FIG. 18C.

FIG. 18C shows the vertical, cross-cut view of the support, SUP shown at FIG. 18B with an end piece close and parallel to it. The strap is not shown. The upper layer of the support is a loop-fastener attachment means, marked at ATM1, and its lower surface is a soft lining, LIN, the layer of foam, FOAM is in between. The end unit is shown on top of the surface of the support, SUP, and consists of a base, BASE, made from a layer of fabric or a polymer. A zone of hook-fastener attachment means, ATM2 is on its upper surface, U-ATM2, and another zone of hook-fastener attachment means is in the lower surface of this piece but is not marked. The other segment of the base, BASE has a layer of adhesive shown at ADH, that has a protective cover, PC, on it.

The method of use:
1. Initially the end unit will be attached to the body of the outer surface of the support, SUP, due to its loop, fastener attachment means, ATM2.
2. Then the strap will wrap around the limb and be pulled to attach to the zone of ATM2 shown on the left border of the support, SUP. This occurs due to the strap's own capability that functions as a loop-fastener attachment means. This step allows the length of the strap to be decided.
3. After the proper length of the strap is decided, it will be further to attach to the upper attachment means, U-ATM2, of the end piece.
4. The extra strap will be cut along the right border of the upper attachment means, U-ATM2, on the upper surface of this piece. Please note that at this point the strap is attached to the U-ATM2 from the outer surface of this piece.
5. Then the user will remove the protective cover, PC, and adhere the base, BASE to the upper surface of the strap by use of the adhesive layer.

At this point the lower surface of the end piece is attached to the upper surface of the support by virtue of the lower attachment means, ATM2 and importantly, its position may be further changed by moving it back and forth on the support.

FIG. 18D shows the vertical, cross-cut view of a mating piece that allows the unit shown at FIG. 18 to be used with a support that is made from a material, such as vinyl, that does not have the loop-fastener means on its own surface. This piece has an outer surface made from a loop-fastener attachment means, ATM1, and its lower surface has a layer of adhesive shown at ADH covered with a protective cover, PC, on it.

The method of use:
1. Initially the protective cover, PC, of this mating piece will be removed and the unit adhered to the outer surface of the support, SUP.

This will modify the vinyl or similar supports, and allow the end piece shown at FIG. 18 to be attached to the loop-fastener attachment means, ATM1, of this piece to function.

FIG. 19 shows the general view of a support unit designed for use in the head. This unit consists of two similar pieces of support units that will be attached to each other by use of straps. The supports have a trapezoid body as show at SUP, with a wider, upper area for the head area and a narrower, lower area for placement on the chin area. Importantly, this support has a laminated body with an outer layer made of loop-fastener attachment means, ATM, an inner layer which is a soft, fabric, lining to contact skin and a layer of foam in between. In the units shown here, the outer surface of the support, SUP, has two layers of long and narrow zones of hook-fastener attachment means, ATM2, that allow the body of another strap made from lycra with a smaller support on its end almost similar to the one shown at FIGS. 1-4 to be attached to it on a detachable, re-attachable basis. This strap, shown in more detail at FIG. 20, will attach to the unit shown at FIG. 19 on a detachable, re-attachable basis. This is important since the body of this particular strap allows such an attachment, which will keep the unit stable and prevent it from moving.

The upper border of the trapezoid support has two stretchable straps made from lycra, shown at HSTR. These straps attach the head areas of these two support pieces together on a stretchable, detachable and re-attachable basis. The free ends of these two straps have a hook-fastener attachment means, ATM2, that allow the ends of these straps to be attached to the outer surface of the other support, SUP, on a detachable, re-attachable basis.

The lower border of the support unit that covers the chin area also has two stretchable, but narrower, straps made from lycra, shown at C-STR, that attach the chin areas of these two supports together on a stretchable, detachable and re-attachable basis. The free ends of these two chin straps, C-STR have small zones of hook-fastener attachment means, ATM2 that allow the ends of these straps to be attached to the outer surface of the second support, SUP, on a detachable re-attachable basis.

The second support piece has similar body, except it does not have the H-STR and C-STR straps, since the these straps will be attached to it on a detachable, re-attachable basis.

FIG. 20 shows schematically the side view of the unit for the head shown at FIG. 19. In this figure the body of the support, SUP, is shown from a laminated piece with an outer surface made from a layer of loop, fastener attachment means, ATM1, and an inner layer made from a layer of soft fabric lining, LIN, that contacts the skin. A layer of foam, FO, is sandwiched between these two layers. The elastic strap for the head is shown at H-STR and the elastic strap for the chin is shown at C-STR both of these have zones of attachment means, ATM2.

FIG. 21 shows schematically the general view of a complementary strap for use with the unit shown at FIG. 19. This strap is similar to the strap shown at FIGS. 1-4. Basically, this shows a long, stretchable strap, STR, that is attached to a support, SUP. The support has a zone of hook-fastener, attachment means, ATM2, on its front surface that allows the body of strap, STR, to attach to it on a detachable, re-attachable basis. The rear surface of this support, STR, may also have another zone of hook-fastener attachment means, ATM2, (which cannot be seen in this view) that allows the support, SUP, from this strap to attach to the outer surface of the support, SUP, for the head and chin on a detachable, re-attachable basis. Please note that the support for the head and chin, has a laminated body with an outer layer made from a layer of loop-fastener attachment means.

The free end of the strap, STR shown on the left side of this figure has an adhesive piece similar to one shown at FIGS. 1-4 that allows the end of this strap to be attached to the outer surface of the strap, STR. This can also have a zone of hook-fastener attachment means, ATM2.

This combination of strap and head and chin support makes a valuable unit, since it allows a very stable and versatile unit for use for the wounds of the head and face.

This unit allows the head straps, H-STR, for the head site to be opened for adjusting the size or the tension of unit or for the examination of the wound site. Also the chin straps, C-STR allow the size and the tension of the unit to be adjusted as well. The strap, STR, goes horizontally around the head and allows the size of the strap and thus, the horizontal tension, to be adjusted. Also, it allows the wounds in the occipital or the frontal part of the head to be checked.

FIG. 22 shows schematically the general view of a support unit for the shoulder. This unit has a non-stretchable support unit shown as ARM-SUP, that covers the outer side of the arm. This support has laminated body with an outer layer made from a loop-fastener attachment means, ATM1, and an inner layer which is a soft fabric lining to contact skin and a layer of foam/sponge in between. In the units shown here, the outer surface of the support, SUP, will have at least two long and narrow zones of hook-fastener attachment means, ATM2. This allows the body of an arm strap, ARM-STR, made from LYCRA (TM), with a smaller support on its free end, almost similar to the one shown at FIGS. 1-4 to be attached to the ARM-SUP, the strap, ARM-STR, is designed to wrap around the upper arm and attach to the surface of the ARM-SUP on a detachable, re-attachable basis.

Another wider, elastic shoulder strap, SH-STR, is also made from LYCRA (TM) and is attached to the upper border of the ARM-SUP. The shoulder strap, SH-STR is designed to cover the shoulder and keep the dressing securely on it. Importantly, the stretchable body of this strap allows the shoulder to move easily. The shoulder strap, SH-STR, has two support pieces of its own that cover the front and rear (FR-SUP and RE-SUP) upper part of the chest. These two supports are made from the same material as the arm support, ARM-SUP, and also have zones of hook-fastener attachment means, ATM2, on their front surfaces.

At the time of use, the FR-SUP is placed on the front of the upper chest and the RE-SUP placed on the rear surface of the chest on the user's back. A strap shown at FIG. 23 goes in front of the chest and wraps in the armpit of the opposite arm, with one free end of the strap attaching to the outer surface of the FR-SUP and the other to the outer surface of the RE-SUP on a detachable, re-attachable basis.

A piece of support, shown as auxiliary sup, AX-SUP, in FIG. 23 and made from same laminated material will go under the armpit and function as a stabilizer, preventing the strap from curling.

Method of use:
1. The body of arm strap, ARM-STR, will wrap around the arm and first attach to the attachment zone, ATM2, from the arm-support, ARM-SUP, due to the special property of the strap that functions as the loop-attachment means. Then the hook-fastener attachment means, ATM2, of the free end of the arm strap, ARM-STR, will attach to the outer surface of the arm support, ARM SUP, on a detachable re-attachable basis. This will hold the arm support, ARM-SUP on the outer surface of the arm in a stable, comfortable fashion.
2. The shoulder straps will be next be wrapped on the shoulder area; its front support, FR-SUP, being placed on the front of the upper chest and its rear support, RE-SUP, placed on the rear surface of the chest behind the user.
3. One free end of strap STR shown at FIG. 23 will be placed on the front of the chest and be pulled to a comfortable tension, wrapped in the armpit of the opposite arm.
4. In the armpit area the strap, STR, will be attached to the outer surface of the axillary sup, AX-SUP shown in FIG. 23 on a detachable, re-attachable basis. Please note that the axillary sup, AX-SUP, is made from a laminated material and has a zone of hook-fastener attachment means on its own outer surface that allows the attachment of the strap, STR, to its body occur. This axillary sup, AXSUP functions as a stabilizer and prevents the strap from curling.
5. Then the free end of the strap, STR, will be pulled in the back of the chest, and be attached to the outer surface of the RE-SUP on a detachable, re-attachable basis.

This method and means makes a stable, comfortable unit for the shoulder joint. Importantly, one end of the strap for the chest will be attached first, and a buckle system as shown at FIGS. 16-18 (or similar units) may be used to adjust the length of this strap. FIG. 23 shows schematically the general view of the strap for the shoulder support unit shown at FIG. 22. In this figure the body of the axillary support, AX-SUP, is shown. The front/outer surface of this support has a zone of hook-fastener attachment means, ATM2, which is under the strap, STR, and cannot be seen in this view. Both free ends of the strap, STR, have zones of hook-fastener attachment means, ATM2. As mentioned above, one free end of this strap will be attached to the front of the front support, FR-SUP. The strap will then be wrapped around the chest, and go under the opposite armpit to have its other free end attach to the outer surface of the RE-SUP on a detachable, re-attachable basis. The body of the axillary support, AX-SUP, covers the axillary area and will keep the strap, STR, in proper position, simultaneously preventing it from curling.

FIG. 24 shows schematically the general view of a support unit for the ankle. This unit also consists of a non-stretchable support unit shown at HEEL-SUP that stands on the front of the ankle joint. This support piece consists of a laminated body with an outer surface made from a layer of loop-fastener attachment means, ATM1, an inner, soft lining for contact skin, and a thin layer of foam in between. The outer surface of the heel support, HEEL-SUP has a long narrow zone of hook-fastener attachment means, ATM2. A wide elastic strap, made from LYCRA, (TM) shown at HEEL-STR is attached to the right border of the HEEL-SUP. The free end of this strap has a zone of hook-fastener attachment means, ATM2. This strap is designed to wrap around the heel and attach to the surface of the heel support, HEEL-SUP, on a detachable, re-attachable basis. The unit has two bands, BAND-A and BAND-B, which are made from Lycra and are similar to the bands shown at FIG. 3. These bands will go around the ankle on each side and attach to the ends of the zone of the hook-fastener attachment means, ATM2, from the support, HEEL-SUP, on a detachable, re-attachable basis. Or, they may have smaller zones of attachment means for their own as shown at ATM2 that allows these zones to be attached to the surface of the heel support, HEEL-SUP on a detachable, re-attachable basis. The strap, STR, and bands, BAND-A and BAND-B, are made from special material (LYCRA-TM) that allows these pieces to attach to the hook-fastener attachment means, ATM2, on a detachable, re-attachable basis.

1. The HEEL-SUP will be placed on the front of the ankle joint.
2. The band, BAND-A, will be pulled to go around the ankle and come forward to attach to the zone of the hook-fastener attachment means, ATM2, from the heel-support, HEEL-SUP, on a detachable, re-attachable basis.
3. The band, BAND-B, will be pulled to go around the ankle and come forward to attach to the zone of the hook-fastener attachment means, ATM2, from the heel-support, HEEL-SUP, on a detachable, re-attachable basis.
4. The heel strap, HEEL-STR, will be pulled to a comfortable tension and then wrapped around the heel and to attach to the zone of hook-fastener attachment means, ATM2, from the heel support, HEEL-SUP. Such an attachment is possible due to the special property of the strap that functions as the stretchable, loop-fastener attachment means.
5. Then the hook-fastener attachment means, ATM2, of the free end of the strap will be attached to the outer surface of the heel support, HEEL-SUP on a detachable, re-attachable basis.
    This method makes a comfortable, sturdy unit for the heel joint. The elastic strap wraps well around the heel and allows it to move freely.

Please note that the method of use of the bands, BAND-A and BAND-B, are shown previously at FIGS. 3-4.

Importantly, it is possible to use this unit without the use of the bands, therefore, some models may not have BAND-A and BAND-B, or may have only one of these bands.

In these models the steps 2 and 3 from the method of use will be omitted

FIG. 25 schematically shows the general view of a support unit for the elbow. This unit consists of two pieces of a non-stretchable, support shown at ELBO-SUP1 and ELBO-SUP2 that will stand on the front of the elbow, above and under the elbow crease. These supports are made from a laminated body with an outer surface made of a layer of loop-fastener attachment means, ATM1, an inner soft lining for contact skin and a thin layer of foam in between. The outer surface of the supports has a zone of hook-fastener attachment means shown at ATM2. A wide, elastic strap, made from LYCRA, (TM) shown at ELBO-STR, is attached to the right border of the ELBO-SUP. The strap, ELBO-STR, has two free ends, F-END1 and F-END2. The very end of these free ends has a zone of hook-fastener attachment means, ATM2. This strap is designed to wrap around the elbow and have its free ends, FEND1 and F-END2, attach to the outer surface of the elbow support, ELBO-SUP1 and ELBO-SUP2, on a detachable, re-attachable basis.

Importantly, the body of the strap, STR, will first attach to the attachment zone, ATM2, from the outer surface of the support units. This attachment is possible due to the special property of the strap that functions as the stretchable, loop-fastener attachment means. Then the attachment means, ATM2, of the free ends of the strap, F-EN)1 and F-END2 will attach to the outer surface of the supports, ELBO-SUP1 and ELBO-SUP2 on a detachable, re-attachable basis. This method makes a comfortable, sturdy unit for the elbow joint area. Importantly, this leaves the front of the elbow open to bend freely.

Method of use.
1. The ELBO-SUP1 will be placed on the front of lower arm above the elbow crease.
2. The upper part of the ELBO-STR, will be wrapped around the elbow joint in the lower arm area above the elbow crease and its upper end piece, F-END1, will be attached to the outer surface of the support, ELBO-SUP1 on a detachable, re-attachable basis.
3. The lower part of the ELBO-STR, along its main body, will be wrapped around the elbow joint in the elbow joint, upper forearm area under the elbow crease and its end piece, F-END2, will be attached to the outer surface of the support, ELBO-SUP2 on a detachable, re-attachable basis.
4. The tension of the strap may be changed by further adjustment of the free ends of the strap, F-END1 and F-END2 to make an effective, yet comfortable, unit. Importantly, the body of the strap, STR, will first attach to the attachment zone, ATM2 from the support unit. Such an attachment is possible due to the special property of the body of strap that functions as the stretchable, loop-fastener attachment means. Then the attachment means, ATM2, of the free ends, F-END1 and F-END2 will attach to the surface of the supports ELBO-SUP1 and ELBO-SUP2, on a detachable, re-attachable basis. This method makes a comfortable, sturdy unit for covering the elbow-joint area. Importantly, this leaves the front of the elbow open to bend freely.

FIG. 26 schematically shows the general view of a support unit for the hip. This unit consists of one non-stretchable, support unit shown at SUP, that is placed on the hip/joint area. This support has zones of hook-fastener attachment means, ATM2, on its front/outer surface, that allow a strap with a loop-fastener attachment means, ATM1, to be attached to it on detachable, re-attachable basis. Alternatively, this support may have a series of D-Rings shown at D.RIN, on its sides in order to allow the free end of the straps to go through, make a U-turn, and attach to their own outer surface on a detachable, re-attachable basis. This method allows the length of the straps to be adjusted. In the models made, the applicant has used three straps with these units. This unit may have another support unit to be placed on the other hip joint in order to hold the straps in a stable position. A pad will be placed under the support for a better result.

FIG. 26B schematically shows a support unit for the hip that consists of hinging two support pieces so that it allows the person to bend the hip joint. In this view the first support, made from a non-stretchable piece, is shown at SUP1, and hinges to the second support, SUP2, at hinge HIN. The outer surfaces of the support pieces have zones of hook-fastener attachment means, ATM2. These zones are not shown for the support 2, SUP2 to prevent a crowded Figure. This allows a series of the straps made from loop-fastener attachment means, ATM1, to be attached to the supports on a detachable, re-attachable basis. This support also may have a series of D-Rings on the sides. The supports shown at these two figures will hold a cushion pad made from a foam covered with fabric that will be attached to the support unit on a detachable, re-attachable basis. This allows the cushion to compress the wound area.

FIG. 26C schematically shows a protective support unit for the chest. This is designed to keep clothing away from the wound site of various forms, particularly after open-heart surgeries. This unit prevents clothing from touching the chest wound, and has a rather rigid and clear support piece that will be held away from the chest wall by use of walls made of foam pads. The outer surface of the support, SUP, has zones of hook-fastener attachment means, ATM2, on its upper and side borders. That allows the straps made from loop-fastener attachment means, ATM1, to be attached to it on a detachable, re-attachable basis. These straps of this unit consists of following:

1. A vertical strap that hangs on each side of the neck, both end pieces attaching to the zone of the hook-fastener attachment means, ATM2, which is located on the upper border of the support.
2. One or two horizontal straps wrap around the chest. Their end pieces will attach to the zone of the hook-fastener attachment means, ATM2, which is located on the borders of the support on its sides. Commonly, one strap around the neck and two from the chest area are used with this unit.

FIG. 26D shows schematically the vertical, cross-cut view of the unit shown at FIG. 26C. In this figure the body of the support, SUP, is shown and has a curve that keeps it away from the wound site. The upper/outer surface of the support has hook-fastener attachment means, ATM2, on its right and left borders. The lower surface of the support has two foam pads, FOAM, that will keep the chest support, SUP, away from the chest wall.

FIGS. 27-28 schematically shows the front and rear view of a support unit for the ear. The front view is shown at FIG. 27 and is rotated 180 degrees to show its rear image that looks somewhat similar to its mirror image at FIG. 28. This unit has a support, SUP, made from a laminated body, with an outer surface made of a layer of loop-fastener attachment means, ATM1, and an inner, soft lining for contacting skin with a thin layer of foam in between. In the process of use this support will fold along a line, FO-LIN. The body of the support, SUP, on the right side has an oval opening, O-OP, with a cut, CUT, on its lower pole. This opening allows the support to be placed around the base of the ear and prevent it from moving. The rear/outer surface of the support, SUP, on the left side has two zones of hook-fastener attachment means, shown at ATM2. A wide, elastic strap, made from LYCRA, (TM) and shown at HE-STR, is designed to wrap around the head. This strap is attached to the body of the support, SUP, along the dotted-line, D-LINE. Importantly, the attachment line, D-LINE, is intentionally away from the edge of the support. This allows the band of attachment means, B-ATM2, to attach to the rear surface of the support, SUP, near the D-LINE, so that the strap will finally wrap over this band.

At the time of use:

A. The oval opening, O-OP of the body of the support, SUP, will be placed around the base of the ear via the cut, CUT. This method will prevent the movement of the support after placement.
B. The rear half of the support, SUP, shown at the left side will fold along the folding line, FO-LIN, and cover the ear. The free borders of these two pieces will be held together by attaching the band of the attachment means, B-ATM2, to the rear surface of the support, SUP, adjacent to the D-LINE. The folded support holds the dressing of the ear on it securely.
C. Then the head strap, HE-STR, which is made from Lycra, will wrap around the head horizontally, on the front of the head, the temporal side and the occipital area respectively. So that ultimately, its free end will attach to the outer surface of the folded support, SUP, by use of the two zones of the attachment means, ATM2.

This method makes a secure and simple means of holding the dressing on the ear, which is commonly difficult.

The body of the support may be made to have more foam and be thicker, or also to have a more protective, non-compressible body to avoid compression of the ear. The strap may also have a piece to go vertically and use the method shown for the head support.

Importantly, a small envelope made from fabric may be used to go over the wound of the ear and be held in place by this unit.

FIG. 29 schematically shows the side view of the unit shown at the previous two figures. This figure shows the support, SUP, the zones of the hook-fastener attachment means, ATM2, on its lower surface, (only one zone is marked), the folding line, FO-LIN and the head strap, HE-STR. Note the point of the attachment of the head strap, HE-STR to the body of the support, SUP, which is marked at D-LINE is intentionally away from the very edge of the support. This is to allow the band of attachment means, B-ATM2 to attach to the rear surface of the support, SUP, near the D-LINE. This special design allows the head strap, HE-STR, to wrap over this band.

FIG. 30 schematically shows the general view of a support unit for the Pacemaker-Defibrillator Wound. This unit consists of a non-stretchable support unit, SUP, that stands on the front of the upper chest in the subclavian area and holds a pad, PAD, on the wound site. The pad, PAD, is attached to the inner surface of the support, SUP, on the upper half area of the support, by a hook-fastener attachment means, ATM2. The body of this support is also made from a laminated body with an outer surface made from a layer of loop-fastener attachment means, ATM1, and an inner soft lining for contact skin, with a thin layer of foam in between. The body of the support on its upper half consists of a thicker part made from a segment of support that has made a U-turn and is attached to its own surface, shown best at U-SUP at FIG. 31. This method makes the upper half of this support have a body made of a layer of loop-fastener attachment means, ATM1, on both sides. The support and attached pad will be held in the upper shoulder area by use of two straps made from a laminated layers of loop-fastener attachment means, ATM1, both its outer and its inner surfaces with a thin layer of foam in between. The straps consist as follows:

a. A horizontal strap shown at H-STR that is designed to wrap around the chest and attach to the outer surface of the support, SUP, by use of a zone of hook-fastener attachment means, ATM2. This is located on both ends of the strap or by use of an extra piece of a double-sided ATM2.
b. A vertical shoulder strap, S-STR, that covers the shoulder. The rear end of this strap makes a U-turn around the horizontal strap, H-STR, shown at U1, to attach to the surface of its own body. This will in turn keep the horizontal strap H-STR and the shoulder strap, S-STR, attached to each other on an adjustable basis, and is shown best at FIG. 31A.
c. The front portion of the shoulder strap, S-STR, stands in front of the support, SUP, and may attach to it by use of pieces of double-sided hook-fastener attachment means, ATM2. It will then move down, the free end of it will making a U-turn around the patient's wrist and attaching to the rear surface of its own body as shown at U2 FIG. 31A. This unit:
1. Provides a mild compression to the wound site and prevents hematoma.
2. Will hold the wrist in position and prevents it from moving.
3. Will prevent other objects from reaching the wound site and causing pain.

Importantly, the size, shape and the make up of the pads may vary. Also the nature of the straps may vary; the straps may be made to be:
1. Non-stretchable
2. Stretchable, elastic material
3. Combination of non-stretchable and stretchable materials. The elastic materials may have their own attachment property or they may have pieces of attachment means attached to their body.

Importantly, in these units the body of the support is primarily made from a material that has an outer surface made from a layer of loop-fastener attachment means ATM1 and its inner surface is a soft lining that would stand on the skin, with a thin layer of foam in between. This allows the shoulder and horizontal straps to be attached to the surface of the support in any area that they touch when a double sided hook-fastener attachment means, ATM2, is used. This method makes these units more versatile.

FIG. 31 schematically shows the side view of the support unit shown in FIG. 30. In this figure the support, SUP is shown and the body of the support makes a U-turn and attaches to its own surface on its upper half as shown at U-SUP. The pad, PAD is attached to the front surface of the U-SUP. The rear surface of the pad is specified at S-PAD and may have a layer of loop-fastener attachment means, ATM1. The pad, PAD, is attached to the inner surface of the support, U-SUP, through use of attachment means, ATM2.

FIG. 31A schematically shows the side view of the arrangement of the straps. In this view the shoulder strap, S-STR, stands on the shoulder (not shown). The rear segment of the strap makes a U-turn, U1, around the horizontal strap, H-STR, and attaches to its own body by use of ATM2, on a detachable, re-attachable basis. This keeps the horizontal strap, H-STR, and the shoulder strap, S-STR, attached to each other on an adjustable basis.

The front segment of the shoulder strap, S-STR, stands in front of the support (not shown) and may attach to it by use of pieces of double-sided ATM2 patches. It moves down in front of the chest, the free end of the strap making a U-turn, U2, around the wrist, WR, of the patient and attaches to the front surface of its own body by the zone of the ATM2 at its end.

FIG. 32 shows a support unit similar to the unit shown in FIG. 30, except this unit has two complementary support pieces. The first support stands in the front of the chest and is referred to as the Front Support, F-SUP, and the second support stands on the back of the chest and is referred to as the Rear Support, R-SUP. The Front Support, F-SUP, stands on the wound site and will be kept in place through use of a strap in the right side, R-STR, another strap on the left side, L-STR and a vertical strap, V-STR that will come together and attach to the surface of the Rear Support, R-SUP. The free ends of these straps have pieces of hook-fastener attachment means shown at ATM2 that attach to the surface of the R-SUP, made from the laminated body with an outer surface made of a layer of loop-fastener attachment means, ATM1, with an inner soft lining and layer of foam in between. The outer surface (the side that does not come in contact with the body site) of the support also has zones of hook-fastener attachment means, ATM2. This allows the body of the strap to attach to these attachment means on a detachable, re-attachable basis. Thus, the rear support, R-SUP, will in fact act as a catalyzer, allowing the ends of the straps to attach to each other easily. Alternatively, the free ends of the attachment means may be attached to each other through use of double-sided loop or hook fasteners, ATM1 and ATM2. The dressings or pads may be placed under the front or rear support.

Importantly, this model makes the process of the dressing easier in some cases by preventing a crowded area in front.

Importantly, the front support may have a body made of stretchable or non-stretchable layers.

The advantage of this unit is that it allows:
1. The placement of this unit with ease and by one hand only.
2. The compression of each segment of the arm or forearms to be modified.
3. The function of the arm and elbow to be easy due to presence of the cut in the support.
4. The arm and elbow to be hung from a stand in order to facilitate the drainage of the tissue.

FIG. 33 shows the general view of a support unit similar to the unit shown at FIG. 6, except this unit is modified for use in the arm and forearms to allow the wound dressing and/or compression of these areas. This unit allows a secure and easy dressing without the need for adhesive tapes. In this model the support, SUP, has a long, rather rectangular shape with cuts in its sides for composure on the elbow crease. The support of this unit stands on the front of the arm and forearm, or on its rear. The support, SUP, has a long zone of hook-fastener attachment means, ATM2, on its left border that allows pieces made of loop-fastener attachment means, ATM1, or a strap made from lycra to be attached to it on a detachable, re-attachable basis. The right border of the support unit, SUP, is attached to a series of straps: STR-A, STR-B that will wrap around the arm area and STR-C, STR-D and STR-E, which are designed to wrap around the forearm. These straps are attached to the border of the support, SUP, on a permanent basis, although importantly, they may be attached to the support on a detachable, re-attachable basis as shown for the leg support. These straps are properly sized to be wrapped around the arm from the axillary area to the elbow-joint area. Importantly, this unit may have three straps for the arm part as well or more.

The straps for the forearm will be placed in the upper, mid- and lower forearm.

These straps may be attached to the support, SUP, by use of pieces of loop-fastener attachment means, ATM2, at their ends. Similar to the leg straps, this method allows the unit to be used for dressing, supporting and compressing the arm and forearms in a very practical, adjustable manner. In this model the straps are also made from one or two layers of LYCRA (TM) and the support means, SUP, is made from a non-stretchable, clear vinyl, or from a laminated body with an outer surface made from a layer of loop-fastener attachment means, ATM1, and an inner layer made from a soft lining that stands on the skin with a thin layer of foam in between. It may also be made from any other materials such as fabric or any other man-made materials. The support may have openings to allow sweat and air to move and also allows a gauze pad or a long, removeable layer of lining shown at LIN, in FIG. 6A or a pad to be placed under it to prevent irritation, place pressure, and allow the application of medication, etc. This unit may allow electrical leads to be held in place as well in order to allow a programmed stimulation of the arm muscles and tissues for various reasons such as the prevention of muscle weakness or prevention of phlebitis.

Importantly, the cuts, CUT, on each side of the support function as hinges and allow the lower segment of the support to rotate in different directions (compared to the upper part) without being disconnected from the upper segment. The advantage of this unit is that it allows the pressure in every special part of the arm and forearms to be adjusted and can be removed and applied easily. When a lining is used, it may be attached to the support, SUP, of the unit on a detachable, re-attachable basis. This allows the lining to be washed or exchanged.

The lower part of this figure shows a piece that allows this unit to be extended to the hand area and be attached to an automatic height elevator shown at FIG. 34. This part shows a support for hand, SUP, that stands on the rear of the hand, and will be attached to the lower extension of the support of the arm-elbow by the hook-fastener attachment means, ATM2, in the upper end of the hand support. The straps of this support will wrap around the palm and fingers and will attach to the rear surface of the body of the hand support. The hook in its lower end allows this support to be attached to the hook, HOOK, of the remote-controlled elevator from FIG. 34.

Please note that the straps shown in the upper part of the picture are not attached to each other and are separate.

Importantly, the straps of these units may be attached to the support unit independently by having both their ends attached to each side of the support on a detachable, re-attachable basis.

Importantly also, the straps may be made from a continuous layer of LYCRA, (TM), to allow a uniform coverage of the area. Although, their end pieces will be separate to allow easy placement. An example of this model is shown for the leg at FIG. 6C and is not repeated here to avoid a lengthy application.

FIG. 34 shows schematically an elevator unit that consists of a stand with a remote-controlled electrical motor, EM. This electrical motor moves an attached hook, HOOK, up and down by use of a remote controller, RMC. This unit allows the support, SUP, of the hand and forearm shown at FIG. 33, to be attached to the hook, HOOK, of this elevator to allow the user to elevate or lower the hand or a feet on a remote-controllable fashion. The elevation of a limb will reduce the stasis and allow swelling to decrease in cases such as post-op breast cancer surgery, or vascular problems of the arm and legs. The pole of this unit can be adjusted to allow the overall height of the unit to be controlled. At the time of use the patient adjusts the pole of the stand to match his/her bed or place of sitting, and places his/her support on his/her arm or leg, and then attaches them to the hook of the elevator. Then, with use of the controller the user will be able to choose a proper height on which the tip of the limb will stand. This will significantly and comfortably facilitate the control of swelling.

FIG. 35 shows the general view of a support unit similar to the unit shown at FIGS. 6 and 33, except this unit is modified for use in the thigh area. This unit also uses a support, SUP, that has a long, rather rectangular shape with cuts, CUT in the sides to stand on the hip joint and functions as a hinge. The upper part of the support, SUP, is for placement on the waist and its lower part will be placed outside of the lateral side of the SUP, to rotate in the different directions without being disconnected from the upper part.

The support, SUP, has a series of straps attached to it. The first strap functions as the belt and is marked at BELT. This will hold the support and prevent if from falling. Other straps, STR-1, STR2, and STR-3, are attached to the support unit on a permanent basis in one side. These straps will wrap around the thigh and attach to the body of the strap with use of their own properties and the presence of the hook fastener attachment means, ATM2, at their ends on a detachable, re-attachable basis (as shown for the leg support). These straps are properly-sized to wrap around the thigh from the groin area to the upper knee. Importantly, the support, SUP, may have an extension to cover the knee area with a strap going around the knee.

Importantly, the extension, shown at EXT, will allow the attachment of this unit to the support of the unit for the leg.

Importantly, the effective length of these straps may be modified by use of the methods and means explained in different parts of this application. Similar to the leg straps, this method allows the support and straps to be used for dressing and supporting the thigh in a very practical, adjustable manner. In this model the straps are also made from one or two layers of LYCRA (TM) and the support means, SUP, is made from non-stretchable, clear vinyl or a laminated body with an outer surface made from a layer of loop attachment means, ATM1. It may also be made from any other materials such as fabrics or any other proper manmade materials. The support may have openings to allow sweat and air to pass through and also allows gauze pad or a long, removeable layer of lining shown at, LIN, in FIG. 6A or pad to be placed under it to prevent irritation, place pressure, and allow application of medication, etc. This unit may allow electrical leads to be held in place as well, in order to allow a programmed stimulation of the thigh muscles and tissues for various reasons such as prevention of muscle weakness or prevention of phlebitis.

The advantage of this unit is that it allows pressure in every special part of the thigh to be adjusted easily and the unit itself can be removed and placed with ease. When a lining is used it may be attached to the support, SUP, of the unit on a detachable, re-attachable basis. This allows the lining to be washed and used, or exchanged as needed.

Please note that these straps are not attached to each other and are separate.

Importantly, the straps may be attached to the support unit independently by having both ends attached to each side of the support on a detachable, re-attachable basis.

Importantly, the straps may be made from a continuous layer of lycra, or an elastic material, to allow a uniform coverage of the area although their end pieces will be separate to allow easy placement. An example of this model is shown for the leg and will not be repeated to avoid a lengthy application.

Method of use.
1. The user will place the support, SUP, on the side of the hip so that the cut, CUT, will be at the hip joint.
2. The user will wrap the belt, BELT, around the waist and attach its free end to the outer surface of the support, SUP, and then extend and attach the free end of the belt to the outer surface of its own. This is possible due to the presence of the attachment means.
3. The user will wrap the stretchable straps, STR-1, STR-2 and STR-3, around the thigh and attach their free end to the hook fastener attachment means of the support marked at H-ATM2, and will continue to attach the free ends of the straps to the outer surface of their own if the strap was longer.
4. Further adjustments allows the unit to be in its proper condition.

FIG. 36 shows the general view of a support unit that is similar to the unit shown at FIG. 35, except that it is modified for use in the groin area to hold a pad over the wound area in the inguinal region. A sample of such a pad is shown at, PAD, which has a trapezoid-shape and can be used after cases such as a hernia surgery in this region. This unit has a support, SUP, that extends and moves down to cover the inguinal area. The body of this support is made from a non-stretchable layer, such as a laminated body, with an outer surface made from a layer of loop fastener attachment means, ATM1, an inner soft lining for contact skin with a thin layer of foam in between. It may also be made from any other manmade materials. The support, SUP, will be held in place securely by a non-stretchable strap, NS-STR, that is attached to the support, SUP, on one side in a permanent, or detachable, re-attachable basis, and allows the other end of the strap to wrap around the waist and function as a sturdy belt. This strap will hold the support, SUP, in a stable position. Please note that due to the extra length of the strap, NS-STR it is schematically shown with a cut in its length. A second, but stretchable, strap, S-STR, is attached to the body of the NS-STR, on a detachable, reattachable basis, in the posterior part of the NS-STR. This method allows the stretchable strap, S-STR, to move down the buttock area of the patient and pass the inner side of the groin, moving up and attaching to the horizontal hook fastener attachment means of the support marked at H-ATM2. This combination makes a secure unit for holding the support unit and compresses the pad, PAD, on the wound area in the groin.

Importantly, when the stretchable strap, S-STR, is made from LYCRA (TM) it will:
1. Expand in the back to function as a comfortable layer of fabric
2. Shrink and roll in the groin area to limit its presence and the pressure to the sides of the groin.
3. Expand like a wing and cover a wider area in the inguinal area, to hold the support means, SUP, in a stable condition. This combination will make a fine unit for this use.

Importantly, the stretchable strap, S-STR, attaches to the body of the NS-STR on a detachable, reattachable basis so that the position and location of such an attachment can be changed as needed.

Importantly, the straps may be attached to the support unit independently, by having both their ends attached to each side of the support on a detachable, re-attachable basis.

Method of use.
1. The user will place the combination of the pad, PAD and support, SUP on the inguinal wound site.
2. The user will wrap the non-stretchable strap, NS-STR around the waist and attach its free end to the outer surface of the support, SUP, due to the presence of the attachment means.
3. The user will move the stretchable, strap, S-STR, down from the buttock area and pass it from the inner side of the groin, moving it up and attaching it to the horizontal hook fastener attachment means of the support marked at H-ATM2.
4. Further adjustments allows the unit to be in its proper condition.

Optional Pieces.

The following pieces may be added to this unit for special intentions to beautify, solve a particular problem or to improve the performances, etc.
1. Use of adhesive tapes to allow the attachment of the free end of the strap to a particular area of the strap or any part of the strap. This allows the length of the strap to be adjusted and is useful in cases where the strap is longer than needed. To solve this problem,
   a. The end of the strap may be cut and a piece of adhesive tape can be utilized to attach the end of the strap to the outer surface of the support, or to the outer surface of the strap itself. These adhesive tapes can be provided to be available for use.
   b. the body of the strap my be folded and attached to itself by various means: stapling, sewing, applying heat, and other various attachment means.
   c. The use of buckle means will allow the alteration of the end of the strap and provide an end that attaches to the support, or to the strap itself. Many different designs of these buckles may be made with the present knowledge at hand. One prototype model is shown in this application at FIGS. 16-17A.
   d. The use of end pieces shown at FIGS. 18-18C and similar means that allow the alteration of the end of the strap to occur. Both eliminate the extra length of the strap and allow it to attach to the support, or to the outer surface of the strap itself. This can be done with more alteration at the end piece to make it have an adhesive or an attachment means, allowing it to be attached to the surface of the strap itself.

The use of D-Rings with these units.

A D-Ring may be attached to the side of the support in order to allow the strap to be fed through it, make a U-turn, and be attached to its own body on a detachable, re-attachable basis. This method may be the preferred model in some cases.

The use of a cover on the support unit.

A cover piece may be used to allow it to go over the line of the attachment of the strap to the body of the support at area ATM2-S. This allows the covering of the attachment line to make a better-looking unit. This cover flap may be separate or attached to the body of the support such as the model shown at FIG. 5A.

Importantly, the attachment means mentioned in this application can be any attachment means that can be used on a detachable, re-attachable basis, some of them as follows:
1. Hook and loop fastener attachment means.
2. Adhesives of various kinds and strengths that provide multiple choices, such as multiple removal and adhesions. The applicant has used certain adhesives that allow the adhesive tape to attach to the outer surface of the strap multiple times on a detachable, re-attachable basis.
3. Magnetic means that also allow multiple removal and attachments.
4. Any other models that may be made in the future.

Importantly, a magnetic piece may be used to attach the strap to the support, to allow the length of the strap to be adjusted. In the prototype model a piece of magnet will be placed in one side of the strap and the opposite piece or a piece of iron will be at the end of the strap. A flat piece of iron may be glued to the strap on each side to allow the end of the strap with a magnet piece to be attached to it.

Importantly, the control of the length of the straps may be achieved by various means, such as:
a. D. rings, placed in the length of the strap.
b. D. rings, placed in the connection spot between the end of the strap and the attachment means on the end.
c. D. rings, placed in the connection spot between the body of the support and the strap.
d. A buckle system is shown in the previous figures.

The support unit may consist of two layers to allow the attachment of the strap between these two layers on an adjustable and detachable, re-attachable basis. These two layers may be the use of the lining and the support. Particularly when the lining is made from an attachment means on its own. For example:
1. The inner surface of the support, SUP, may have attachment means made from hook fastener, ATM2.
2. The outer surface of the lining made from a loop fabric.
3. The strap to have a body made from a fabric that allows it to function as a loop fastener attachment means, ATM1, and has a piece of attachment means made from the hook fastener attachment means, ATM2.

This will allow the strap to be squeezed between the inner support and outer lining and to be adjustable to be removed back and forth.

Importantly, these units and supports may be used for compression of the area or use of balloons, or specially-shaped pieces to have an effect in the underlying area or various therapeutic or diagnostic means.

Importantly, please notice in the prototype units made by this applicant, the ATM1 attachment means are a loop-type of fastener and the ATM2 are a hook-type of fastener means that function as the hook-loop fasteners. However, any other means to function in these units may be used.

Medicated Pads.

The gauze pads may be medicated with various medications that will be covered by a protective layer and that allows the protective layers to be removed before application of the medicated pad onto the wound area. These are particularly useful in natural or manmade disasters, where the use of these units on emergency basis are essential.

Importantly, the support or the strap may have a clear pocket called an information pocket, (IP) which may also be attached to the body of the strap through attachment means.

Importantly, the clear pocket may be inside the wall of the strap and be part of the wall, and it may also be used to allow the wound site to be clearly visible. The information pocket allows certain information, such as time of the dressing application or other information about the person using the unit to be placed inside it.

Use of tabs with these units.

These units may have optional tabs on the surfaces of the supports or the straps in order to allow them to be held or to move the support or straps.

The tabs will allow the pulling of the strap so the user can adjust it or change the dressing underneath without disturbing the whole unit.

Please note that size, shape, thickness, color, materials and other important characteristics of these units and their components may vary.

The invention claimed is:

1. A wrap for encircling a portion of a living body, the wrap comprising:
A) a relatively non-stretchable support; and
B) a strap
   i) that has one end portion attached to the support and extends lengthwise to an opposite end portion,
   ii) that is relatively stretchable lengthwise from the one end portion for encircling, with stretching, the portion of the living body and attaching to an attachment means on the support to compressively wrap the encircled portion of the body, and
   iii) that comprises relatively stretchable material that directly attaches the strap to the attachment means on the support to keep the encircled portion of the living body compressively wrapped,
wherein the opposite end portion of the strap comprises stretchable material that is beyond a zone of the stretchable material that attaches directly to the attachment means, and the strap includes additional attachment means to which the stretchable material in the opposite end portion of the strap attaches.

2. A wrap as set forth in claim 1 wherein the entire strap comprises relatively stretchable material.

3. A wrap as set forth in claim 1 further including at least one additional strap, the at least one additional strap
   i) having a one end portion attached to the support and extending lengthwise to an opposite end portion,
   ii) being relatively stretchable lengthwise from the one end portion for encircling, with stretching, the portion of the living body and attaching back to the attachment mean on the support to compressively wrap the encircled portion of the body, and
   iii) that comprises relatively stretchable material that directly attaches to the attachment means to keep the encircled the portion of the living body compressively wrapped.

4. A wrap as set forth in claim 3 wherein one of the at least one additional straps is disposed laterally of another of the at least one additional straps and the two additional straps are disposed relative to the first-mentioned strap such that the one additional strap is disposed laterally to one lateral side of the first-mentioned strap and the another additional strap is disposed laterally to an opposite lateral side of the first-mentioned strap.

5. A wrap as set forth in claim 3 wherein the at least one additional strap and the first-mentioned strap are arranged on the support for wrapping around the portion of the living body in opposite circumferential senses when the wrap is being applied to the body.

6. A wrap as set forth in claim 1 in which the strap has an inner surface and an outer surface, and the additional attachment means comprises hook fastener material disposed on the outer surface of the strap.

7. A wrap as set forth in claim 1 in which the strap has an inner surface and an outer surface, and the additional attachment means comprises hook fastener material disposed on the inner surface of the strap.

8. A wrap as set forth in claim 1 in which the attachment means on the support comprises at least one zone of hook fastener material.

9. A wrap as set forth in claim 1 in which the additional attachment means comprises hook fastener material, and the relatively non-stretchable support comprises an outer surface of loop fastener material to which the hook fastener material of the additional attachment means can detachably and re-attachably attach.

10. A wrap as set forth in claim 1 including at least one piece of material applied to the relatively stretchable material of the strap to hold the relatively stretchable material of the strap to the shape of the respective piece of material at the location of each such piece of material.

11. A wrap as set forth in claim 10 in which the at least one piece of material applied to the relatively stretchable material of the strap extends across a width of the relative stretchable material of the strap.

12. A wrap for encircling a portion of a living body, the wrap comprising:
A) a support; and
B) a strap:
i) that has one end portion attached to the support; and
ii) that is long enough to encircle the portion of the living body and attach, with some stretching, to the support for keeping the encircled portion of the body wrapped; and
C) at least one piece for adhesively attaching the support to the living body to hold the support in place while the strap is being wrapped around the encircled portion of the living body, the at least one piece having a first zone detachably attached to an attachment means on the support and a second adhesive-containing zone disposed beyond the support.

13. A wrap as set forth in claim 12 wherein the first zone of the at least one piece comprises hook fastener material disposed on a surface that faces away from the support to provide for additional detachable and re-attachable attachment of the relatively stretchable material of the strap.

14. A piece for use with a support portion of a wrap that encircles a portion of a living body, the piece comprising:
a first zone on an underlying surface of the piece for adhesively attaching the piece to the living body to hold the support in place while the wrap is being wrapped around the encircled portion of the living body, a second zone on the underlying surface of the piece comprising attachment means for attaching the piece to the support, and a third zone on an overlying surface of the piece comprising hook fastener material.

15. A piece as set forth in claim 14 wherein the third zone overlies the second zone.

16. A piece as set forth in claim 14 including a strippable cover that covers adhesive on the first zone and is removed to expose the adhesive.

17. A piece as set forth in claim 14 wherein the attachment means of the second zone comprises loop fastener material for detachably attaching the piece to hook fastener material on the support.

18. A wrap for encircling a portion of a living body, the wrap comprising:
A) a relatively non-stretchable support; and
B) a strap
i) that has one end portion attached to the support and extends lengthwise to an opposite end portion,
ii) that is relatively stretchable lengthwise from the one end portion for encircling, with stretching, the portion of the living body and attaching to an attachment means on the support to compressively wrap the encircled portion of the body, and
iii) that comprises relatively stretchable material that directly attaches the strap to the attachment means on the support to keep the encircled portion of the living body compressively wrapped, and
in which the opposite end portion of the strap comprises an additional attachment means which is disposed beyond a zone of the stretchable material that attaches directly to the attachment means on the support for detachably and re-attachably attaching the opposite end portion of the strap to the strap.

19. A wrap as set forth in claim 18 in which the strap has an inner surface and an outer surface, and the additional attachment means comprises hook fastener material disposed on the outer surface of the strap.

20. A wrap as set forth in claim 18 in which the strap has an inner surface and an outer surface, and the additional attachment means comprises hook fastener material disposed on the inner surface of the strap.

21. A wrap as set forth in claim 18 in which the attachment means on the support comprises at least one zone of hook-type hook fastener material.

22. A wrap as set forth in claim 18 in which the additional attachment means comprises hook fastener material, and the relatively non-stretchable support comprises an outer surface of loop fastener material to which the hook fastener material of the additional attachment means can detachably and re-attachably attach.

23. A wrap as set forth in claim 18 including at least one piece of material applied to the relatively stretchable material of the strap to hold the relatively stretchable material of the strap to the shape of the respective piece of material at the location of each such piece of material.

24. A wrap as set forth in claim 23 in which the at least one piece of material applied to the relatively stretchable material of the strap extends across a width of the relative stretchable material of the strap.

25. A wrap as set forth in claim 18 in which the support comprises an information pocket into which a sheet of information can be inserted.

* * * * *